US012030949B2

(12) United States Patent
Blanchetot et al.

(10) Patent No.: US 12,030,949 B2
(45) Date of Patent: Jul. 9, 2024

(54) MULTISPECIFIC ANTIBODIES AGAINST IL-5 AND IL-4R

(71) Applicant: argenx BV, Ghent (BE)

(72) Inventors: Christophe Blanchetot, Ghent (BE); Marie Godar, Ghent (BE); Bart Lambrecht, Ghent (BE)

(73) Assignee: argenx BV, Ghent (BE)

( * ) Notice: Subject to any disclaimer, the term of this patent is extended or adjusted under 35 U.S.C. 154(b) by 518 days.

(21) Appl. No.: 16/966,237

(22) PCT Filed: Feb. 15, 2019

(86) PCT No.: PCT/EP2019/053890
§ 371 (c)(1),
(2) Date: Jul. 30, 2020

(87) PCT Pub. No.: WO2019/158728
PCT Pub. Date: Aug. 22, 2019

(65) Prior Publication Data
US 2020/0399382 A1 Dec. 24, 2020

(30) Foreign Application Priority Data

Feb. 15, 2018 (GB) .................................. 1802487

(51) Int. Cl.
*C07K 16/18* (2006.01)
*C07K 16/24* (2006.01)
*C07K 16/28* (2006.01)

(52) U.S. Cl.
CPC ........ *C07K 16/2866* (2013.01); *C07K 16/244* (2013.01); *C07K 2317/22* (2013.01);
(Continued)

(58) Field of Classification Search
CPC ............ C07K 16/2866; C07K 2317/31; C07K 2317/565; C07K 2317/76
See application file for complete search history.

(56) References Cited

U.S. PATENT DOCUMENTS

| 5,821,333 A | 10/1998 | Carter et al. |
| 5,892,019 A | 4/1999 | Schlom et al. |

(Continued)

FOREIGN PATENT DOCUMENTS

| EP | 2275443 A1 | 1/2011 |
| EP | 3064510 A1 | 9/2016 |

(Continued)

OTHER PUBLICATIONS

Goel et al. Plasticity within the antigen-combining site may manifest as molecular mimicry in the humoral immune response. J. Immunol. 2004; 173:7358-7367.*

(Continued)

*Primary Examiner* — Dong Jiang
(74) *Attorney, Agent, or Firm* — Dechert LLP; Andrew T. Wilkins; Kayla L. Metzger

(57) ABSTRACT

The present invention relates to combination therapies and to their use in the treatment of chronic airway disease, particularly use in the treatment of asthma. The combination therapies comprise (i) an antagonist of IL-5:IL-5R and (ii) an antagonist of IL-4:IL-4R and/or an antagonist of IL-13:IL-13R. The present invention also provides bispecific antibodies comprising an antigen binding domain that binds to IL-4Rα and an antigen binding domain that binds to IL-5. The bispecific antibodies may be used for the treatment of chronic airway disease, particularly asthma.

20 Claims, 26 Drawing Sheets

Specification includes a Sequence Listing.

(52) U.S. Cl.
CPC ...... C07K 2317/24 (2013.01); C07K 2317/31 (2013.01); C07K 2317/565 (2013.01); C07K 2317/622 (2013.01); C07K 2317/76 (2013.01)

(56) References Cited

U.S. PATENT DOCUMENTS

| | | |
|---|---|---|
| 6,670,453 B2 | 12/2003 | Frenken et al. |
| 8,216,805 B2 | 7/2012 | Carter et al. |
| 8,524,231 B2 | 9/2013 | Dreier et al. |
| 8,629,246 B2 | 1/2014 | Humphreys et al. |
| 8,703,131 B2 | 4/2014 | Beirnaert et al. |
| 9,212,230 B2 | 12/2015 | Schuurman et al. |
| 9,499,634 B2 | 11/2016 | Dixit et al. |
| 9,834,615 B2 | 12/2017 | Fischer et al. |
| 2004/0253638 A1 | 12/2004 | Casterman et al. |
| 2006/0063921 A1 | 3/2006 | Moulder et al. |
| 2009/0252729 A1 | 10/2009 | Farrington et al. |
| 2010/0254989 A1 | 10/2010 | Bossenmaier et al. |
| 2010/0331527 A1 | 12/2010 | Davis et al. |
| 2011/0081345 A1 | 4/2011 | Moore et al. |
| 2011/0165621 A1 | 7/2011 | Dreier et al. |
| 2011/0293613 A1 | 12/2011 | Brinkmann et al. |
| 2012/0184716 A1 | 7/2012 | Fischer et al. |
| 2013/0178605 A1 | 7/2013 | Blein et al. |
| 2014/0079689 A1 | 3/2014 | Elliott et al. |
| 2014/0154254 A1 | 6/2014 | Kannan et al. |
| 2014/0302037 A1 | 10/2014 | Borges et al. |
| 2014/0363426 A1 | 12/2014 | Moore et al. |
| 2015/0252119 A1 | 9/2015 | Frey et al. |
| 2015/0307628 A1 | 10/2015 | Kim et al. |
| 2016/0017057 A1 | 1/2016 | Dave et al. |
| 2016/0115241 A1 | 4/2016 | Yan et al. |
| 2016/0251440 A1 | 9/2016 | Roonbrouck et al. |
| 2016/0272706 A1* | 9/2016 | Carmen ............. C07K 16/2866 |
| 2016/0280795 A1 | 9/2016 | Zhong |
| 2016/0319036 A1 | 11/2016 | Breunker et al. |
| 2017/0066843 A1 | 3/2017 | Ulitin et al. |
| 2017/0320967 A1 | 11/2017 | Yang et al. |

FOREIGN PATENT DOCUMENTS

| | | |
|---|---|---|
| WO | 2005007699 A2 | 1/2005 |
| WO | 2005123126 A2 | 12/2005 |
| WO | WO 2010/001251 A2 | 1/2010 |
| WO | WO 2010/035012 A1 | 4/2010 |
| WO | 2011137395 A1 | 11/2011 |
| WO | WO 2013/064701 A2 | 5/2013 |
| WO | WO 2013/136186 A2 | 9/2013 |
| WO | WO 2014/022540 A1 | 2/2014 |
| WO | WO 2014/124326 A1 | 8/2014 |
| WO | 2014205365 A1 | 12/2014 |
| WO | WO 2015/033223 A2 | 3/2015 |
| WO | WO 2016/086186 A2 | 6/2016 |
| WO | WO 2016/086189 A2 | 6/2016 |
| WO | 2016113217 A1 | 7/2016 |
| WO | WO 2016/118742 A1 | 7/2016 |
| WO | WO 2017/218707 A2 | 12/2017 |
| WO | WO 2018/014260 A1 | 1/2018 |
| WO | WO 2018/014855 A1 | 1/2018 |
| WO | WO 2018/206748 A1 | 11/2018 |
| WO | 2019158728 A1 | 8/2019 |

OTHER PUBLICATIONS

Rudikoff et al. Single amino acid substitution altering antigen-binding specificity. Proc. Natl. Acad. Sci. USA, 1982, 79:1979-1983.*

Basilico et al. (May 27, 2014) "Four individually druggable MET hotspots mediate HGF-driven tumor progression," J. Clin. Invest. 124:3172-3186.

Borrock, et al., (2012) "Revisiting the role of glycosylation in the structure of human IgG Fc," ACS Chem. Biol., 7:1596-1602.

Carter, et al., (2001) "Bispecific human IgG by design," Journal of Immunological Methods, 248:7-15.

Chan et al. (2010) "Therapeutic antibodies for autoimmunity and inflammation," Nat. Rev. Immunol. 10:301-316.

Chothia et al. (1987) "Canonical structures for the hypervariable regions of immunoglobulins," J. Mol. Biol. 196:901-917.59.

Chothia et al. (1992) "Structural repertoire of the human VH segments," J. Mol. Biol. 227:799-817.

De Haard (1999) "A large non-immunized human Fab fragment phage library that permits rapid isolation and kinetic analysis of high affinity antibodies," J. Biol. Chem. 274(26):18218-18230.

Deckers et al., "Epicutaneous sensitization to house dust mite allergen requires interferon regulatory factor 4-dependent dermal dendritic cells", Journal of Allergy and Clinical Immunology, 2017, 140(5): 1364-1377.

Dullaers et al., "House dust mite-driven asthma and allergen-specific T cells depend on B cells when the amount of inhaled allergen is limiting", Journal of Allergy and Clinical Immunology, 2017, 140(1): 76-88.

Gauthier et al., "Evolving Concepts of Asthma", American Journal of Respiratory and Critical Care Medicine, 2015, 192(6): 660-668.

Godar et al., "Dual anti-idiotypic purification of a novel, native-format biparatopic anti-MET antibody with improved in vitro and in vivo efficacy", Scientific Reports, Aug. 2016, 6(1):31621.

Godar et al., "Personalized medicine with biologics for severe type 2 asthma: current status and future prospects", mAbs, 2018, 10(1): 1-12.

Gunasekaran, et al., (2010) "Enhancing antibody Fc heterodimer formation through electrostatic steering effects," The Journal of Biological Chemistry, 285(25):19637-19646.

Hamers-Casterman, et al., (1993) "Naturally occurring antibodies devoid of light chains," Nature, 363:446-448.

Hinton, et al., (2006) "An engineered human IgG1 antibody with longer serum half-life," The Journal of Immunology, 176:346-356.

Holliger et al. (2005) "Engineered antibody fragments and the rise of single domains," Nature Biotechnol. 23:1126-1136.

International Search Report and Written Opinion for PCT International Patent Application No. PCT/EP2018/086755, dated Mar. 3, 2019.

Kabat et al., "Unusual distributions of amino acids in complementarity-determining (hypervariable) segments of heavy and light chains of immunoglobulins and their possible roles in specificity of antibody-combining sites", J. Biol. Chem., 1977, 252(19): 6609-6616.

Klein, et al., (2012) "Progress in overcoming the chain association issue in bispecific heterodimeric IgG antibodies," mAbs, 4(6):653-663.

Kontermann, "Dual Targeting Strategies with Bispecific Antibodies", mAbs, 2012, 4(2): 182-197.

Labrijn, et al., (2013) "Efficient generation of stable bispecific IgG1 by controlled Fab-arm exchange," PNAS, 110(13):5145-5150.

Lambrecht et al., "The immunology of asthma", Nat. Immunol., Jan. 2015, 16(1): 45-56.

Lewis, et al., (2014) "Generation bispecific IgG antibodies by structure-based design of an orthogonal Fab interface," Nature Biotechnology, 32(2):191-198.

Lindhofer, et al., (1995) "Preferential species-restricted heavy/light chain pairing in rat/mouse quadromas," The Journal of Immunology, 155:219-225.

Maccallum et al. (1996) "Antibody-antigen interactions: contact analysis and binding site topography," J. Mol. Biol. 262:732-745.

Mccormick et al., "Commentary: IL-4 and IL-13 Receptors and Signaling", Cytokine, 2015, 75(1): 38-50.

Morea (2000) et al. "Antibody modeling: implications for engineering and design," Methods. 20(3):267-279.

Muda, et al., (2011) "Therapeutic assessment of SEED: a new engineered antibody platform designed to generate mon-and bispecific antibodies," Protein Engineering, Design and Selection, 24(5):447-454.

Porsbjerg et al., "Co-morbidities in severe asthma: Clinical impact and management", Respirology, May 2017, 22(4): 651-661.

Presta et al. (2012) "Molecular engineering and design of therapeutic antibodies," Current Opinion in Immunology, 20:460-470.

Ray et al., "Emerging molecular phenotypes of asthma", Am J Physiol—Lung Cellular and Molecular Physiology, Jan. 15, 2015, 308(2): 130-140.

(56) References Cited

OTHER PUBLICATIONS

Ridgway, et al., (1996) "'Knobs-into-holes' engineering of antibody Ch3 domains for heavy chain heterodimerization," Protein Engineering, 9(7):617-621.
Roux et al. (1998) "Comparisons of the ability of human IgG3 hinge mutants, IgM, IgE, and IgA2, to form small immune complexes: a role for flexibility and geometry," J. Immunol. 161:4083-4090.
Schuijs et al., "Farm dust and endotoxin protect against allergy through A20 induction in lung epithelial cells", Science, 2015, 349:1 106-10.
Sheridan, "Drugmakers cling to dual IL-13/IL-4 blockbuster hopes", Nat. Biotechnol., Jan. 2018, 36(11): 3-5.
Spiess, et al., (2013) "Bispecific antibodies with natural architecture produced by co-culture of bacteria expressing two distinct half-antibodies," Nature Biotechnology, 31(8):753-758.
Tatusova et al., "BLAST 2 Sequences, a new tool for comparing protein and nucleotide sequences", FEMS Microbiol Lett., Jan. 17, 1999, 174(2): 247-250.
Tramontano et al. (1990) "Framework residue 71 is a major determinant of the position and conformation of the second hypervariable region in the VH domains of immunoglobulins," J. Mol. Biol. 215:175-182.
UniProtKB—P05112 (IL4_HUMAN), "Interleukin-4", Aug. 13, 1987, Retrieved from: <http://www.uniprot.org/uniprot/P05112>.
UniProtKB—P05113 (IL5_HUMAN), "Interleukin-5", Aug. 13, 1987, Retrieved from: <http://www.uniprot.org/uniprot/P05113>.
UniProtKB—P24394 (IL4RA_HUMAN), "Interleukin-4 receptor subunit alpha", Mar. 1, 1992, Retrieved from: <http://www.uniprot.org/uniprot/P24394>.
UniProtKB—P35225 (IL13_HUMAN), "Interleukin-13", Feb. 1, 1994, Retrieved from: <http://www.uniprot.org/uniprot/P35225>.
UniProtKB—Q01344 (IL5RA_HUMAN), "Interleukin-5 receptor subunit alpha", Jul. 1, 1993, Retrieved from: <http://www.uniprot.org/uniprot/Q01344>.
Vaccaro, et al., (2005) "Engineering the Fc region of immunoglobulin G to modulate in vivo antibody levels," Nature Biotechnology, 23(10): 1283-1288.
Wang et al. (Jan. 2007) "Antibody structure, instability, and formulation," Journal of Pharmaceutical Sciences. 96: 1-26.
Wenzel, "Asthma phenotypes: the evolution from clinical to molecular approaches", Nature Medicine, May 4, 2012, 18(5): 716-725.
Wranik, et al., "LUZ-Y, a novel platform for the mammalian cell production of full-length IgG-bispecific antibodies," The Journal of Biological Chemistry, 287(52): 43331-43339.
Yeung, et al., (2009) "Enigeering human IgG1 affinity to human neonatal Fc receptor: Impact of affinity improvement on pharmacokinetics in primates," The Journal of Immunology, 182: 7663-7671.
Zalevsky et al. (2010) "Enhanced antibody half-life improves in vivo activity," Nat. Biotechnol., 28(2): 157-159.
Nagase, "Potency of Molecular-Targeting Agents in the Treatment of Allergic Diseases," Internal Medicine. 2016;118(6):1121-1128, English translation is considered.
Walsh et al., "Biologics targeting IL-5, IL-4 or IL-13 for the treatment of asthma—an update," Expert Rev Clin Immunol. 13(2): 143-149, doi: 10.1080/1744666X.2016.1216316. Epub Aug. 2, 2016.
Hansbro et al., "Th2 cytokine antagonists: potential treatments for severe asthma", Expert Opin Investig Drugs. 2013;22(1):49-69.
Godar et al., "A bispecific antibody strategy to target multiple type 2 cytokines in asthma", J Allergy Clin Immunol.2018;142(4):1185-1193.
International Search Report and Written Opinion received for PCT/EP2019/053890, mailed on Jul. 19, 2019.
International Preliminary Report On Patentability received for PCT/EP2019/053890, mailed on Aug. 27, 2020.

* cited by examiner

Fig. 1
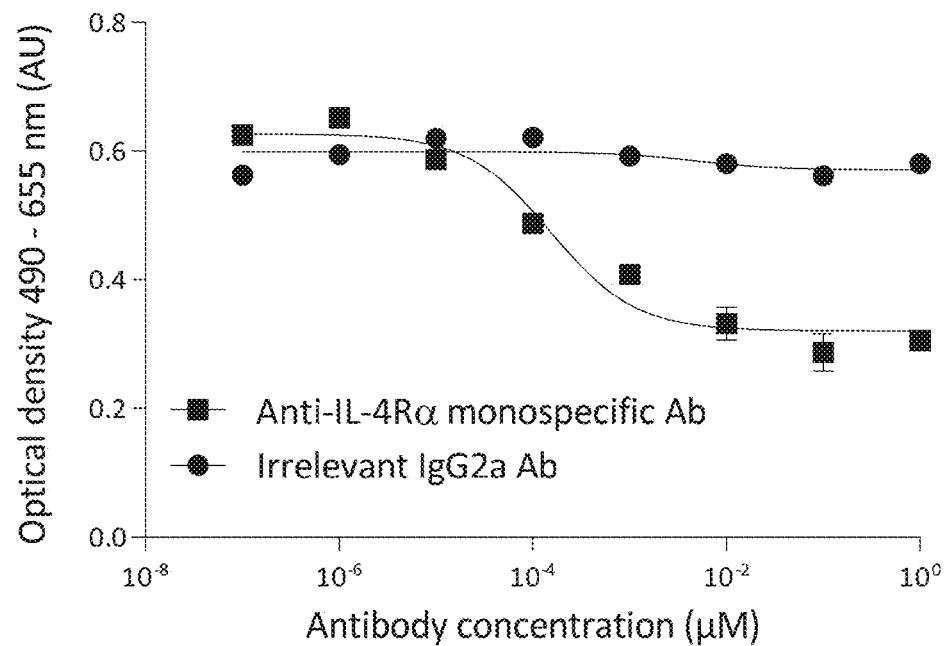
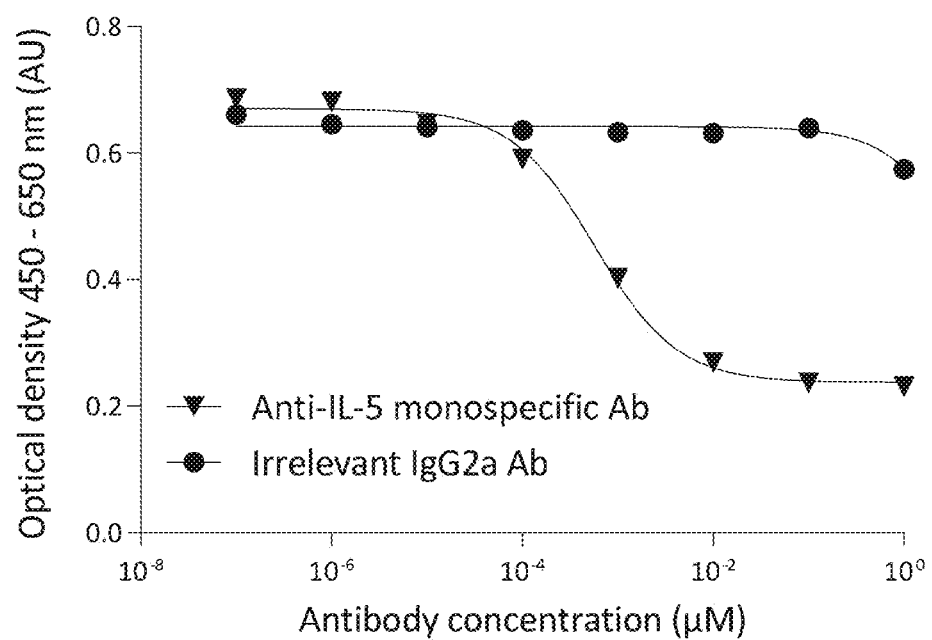

Fig. 2
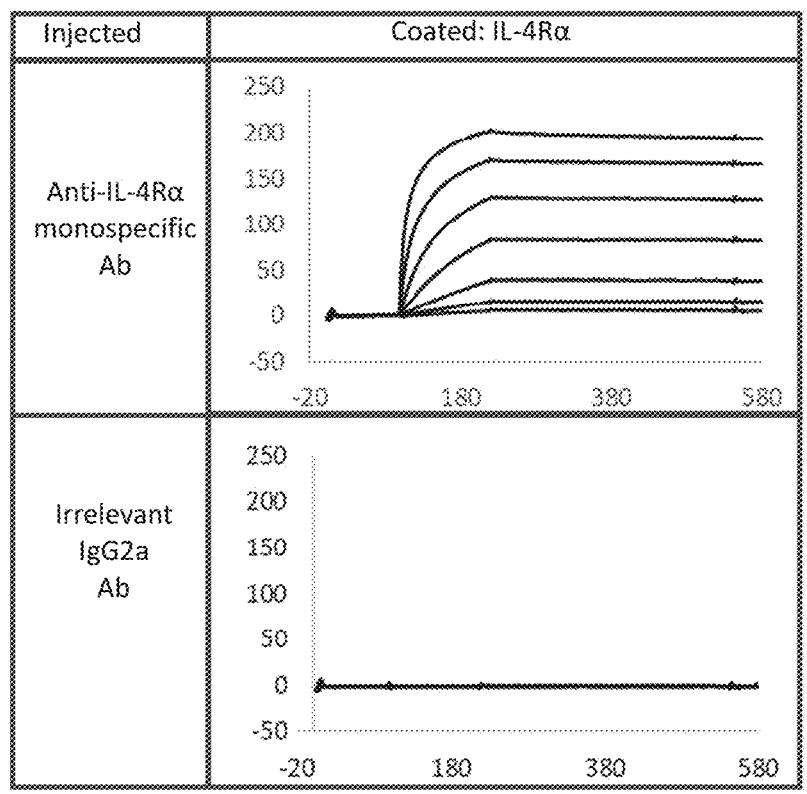
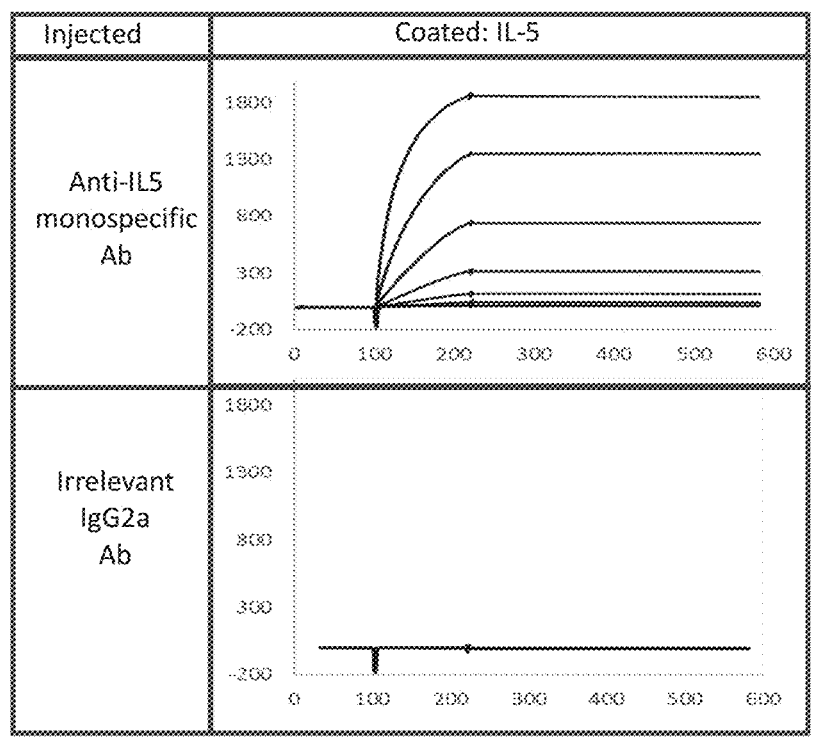

Fig. 4
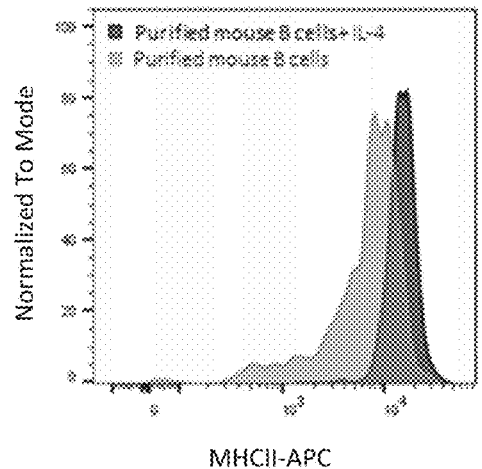
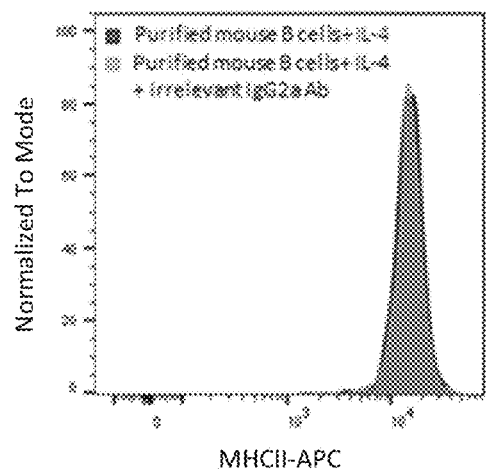
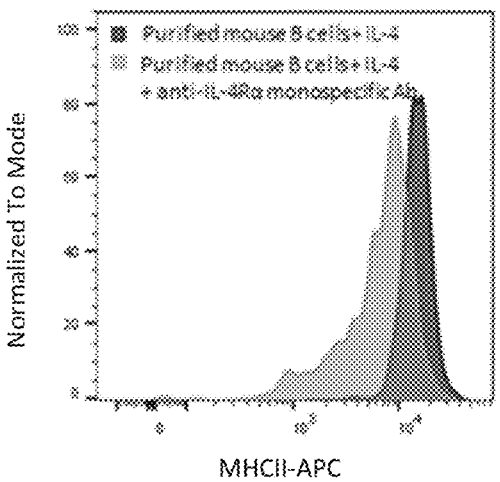

Fig. 8
☐ HDM/PBS/Irrelevant IgG2a Ab
■ HDM/HDM/Irrelevant IgG2a Ab
▩ HDM/HDM/Anti-IL-4Rα monospecific Ab
▒ HDM/HDM/Anti-IL-5 monospecific Ab
≡ HDM/HDM/Anti-IL-4Rα/IL-5 monospecific Abs
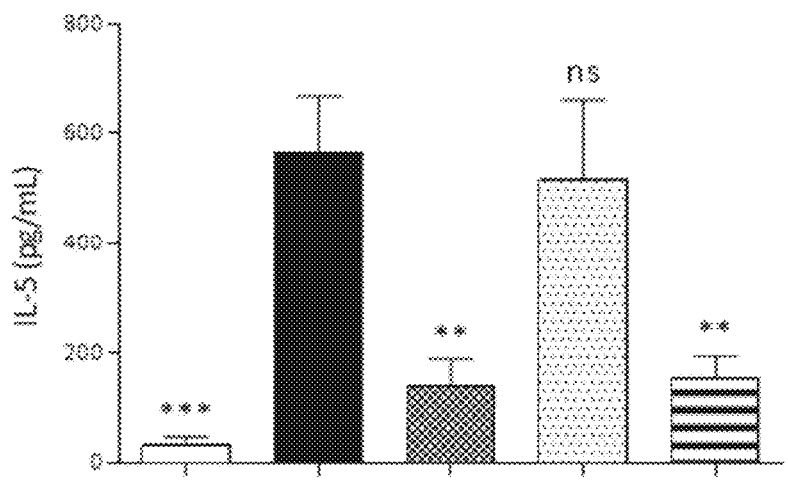
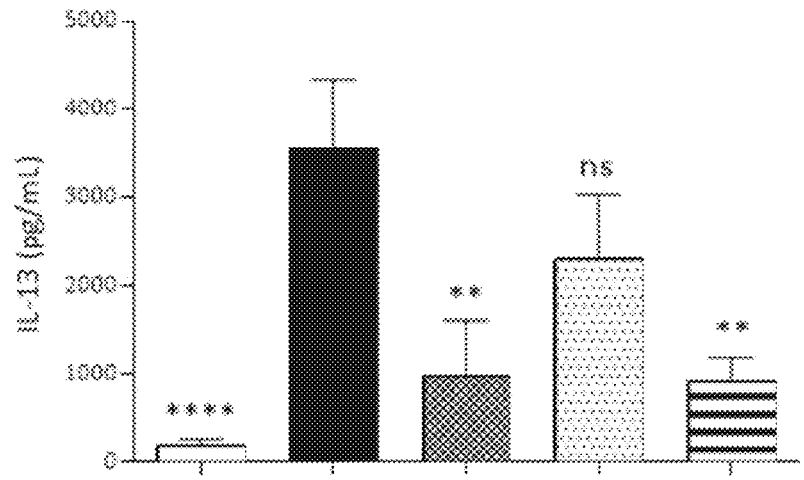

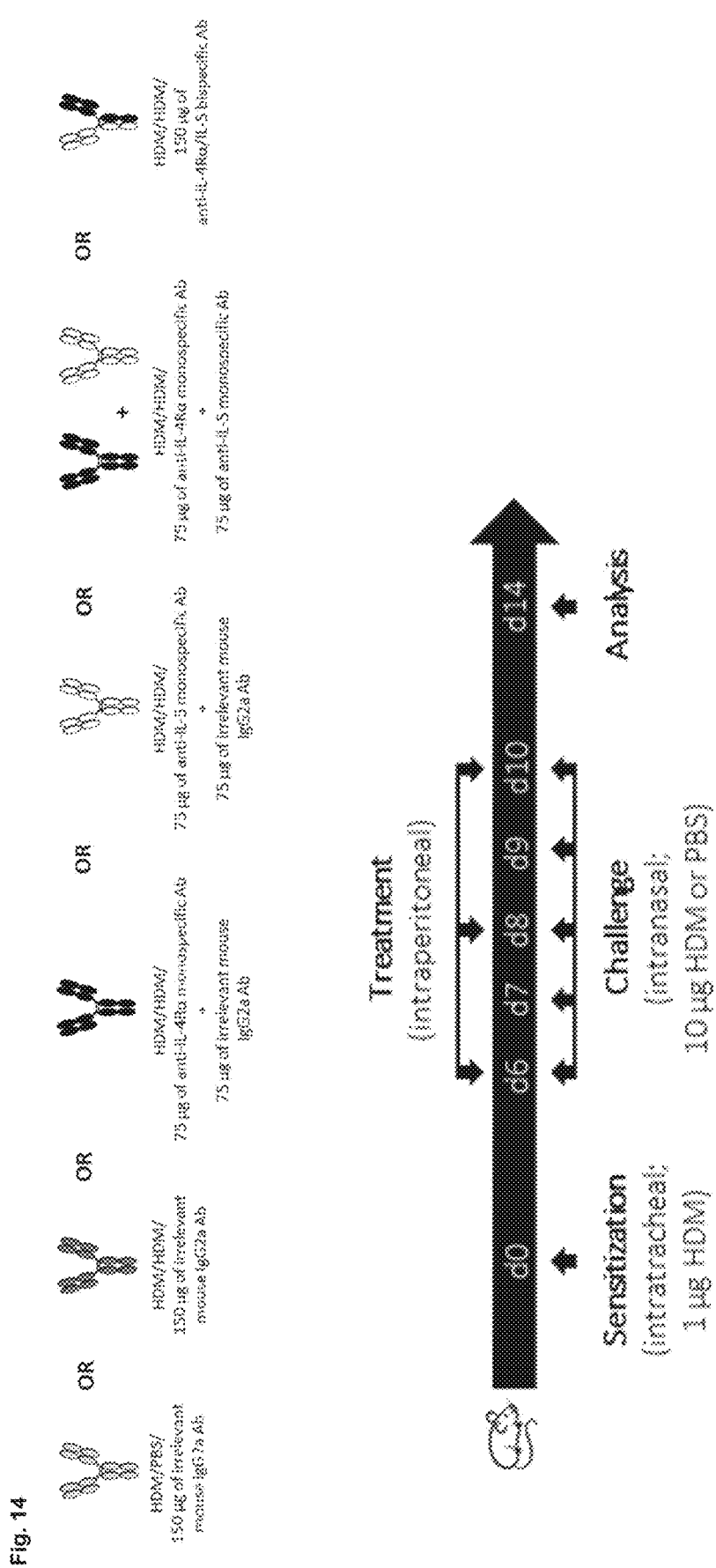

Fig. 16
- ☐ HDM/PBS/Irrelevant IgG2a Ab
- ■ HDM/HDM/Irrelevant IgG2a Ab
- ▨ HDM/HDM/Anti-IL-4Rα monospecific Ab
- ▧ HDM/HDM/Anti-IL-5 monospecific Ab
- ▬ HDM/HDM/Anti-IL-4Rα/IL-5 monospecific Abs
- ▥ HDM/HDM/Anti-IL-4Rα/IL-5 bispecific Ab
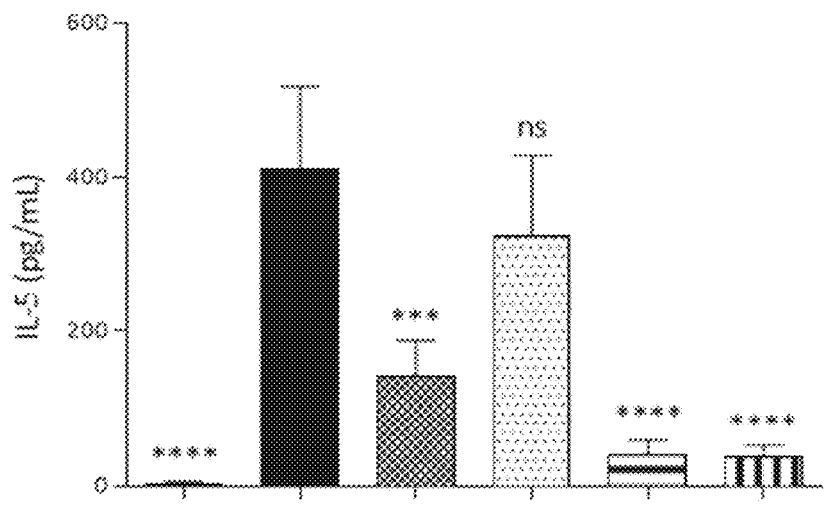
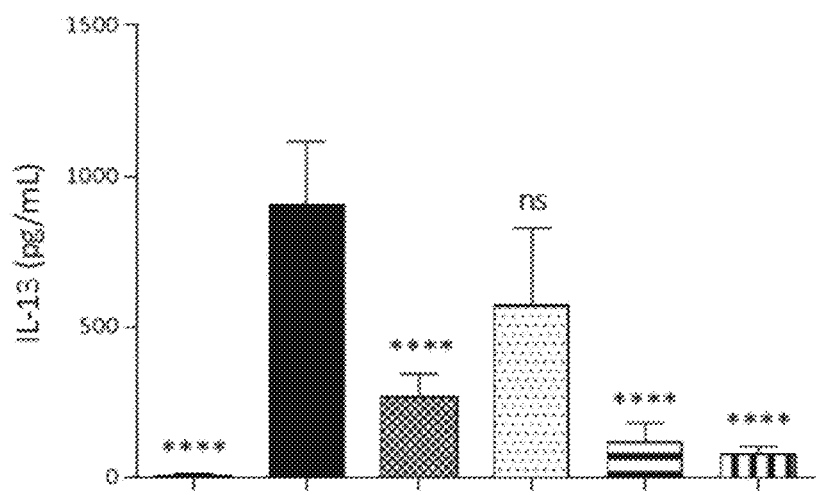

Fig. 22
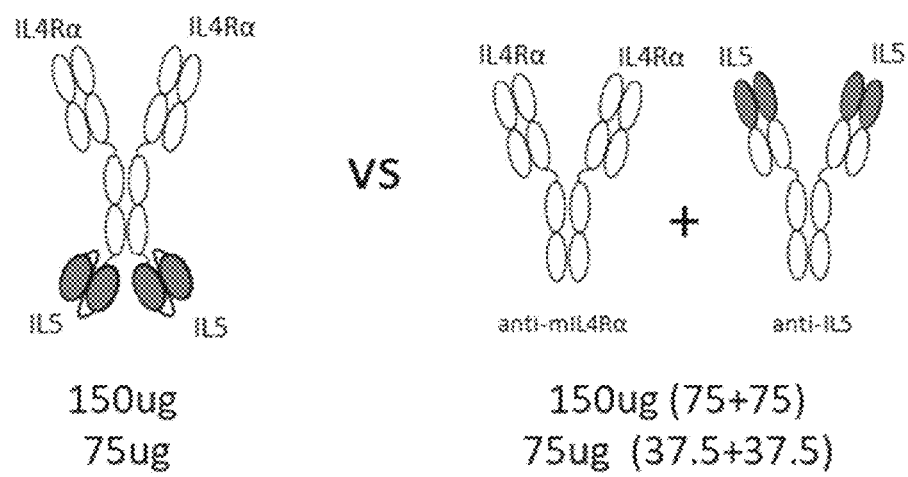
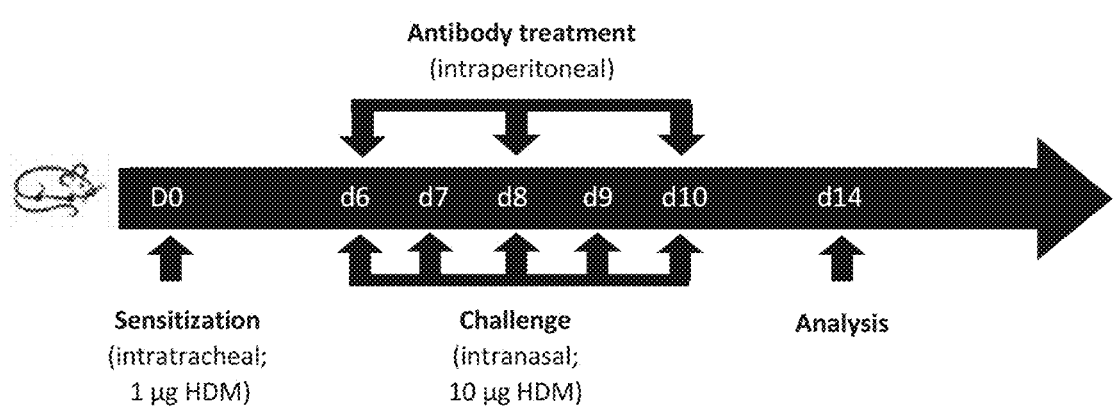

Fig. 23
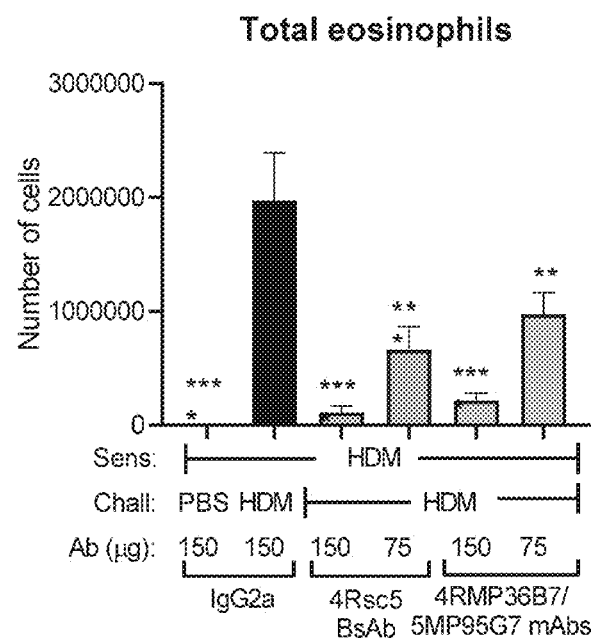
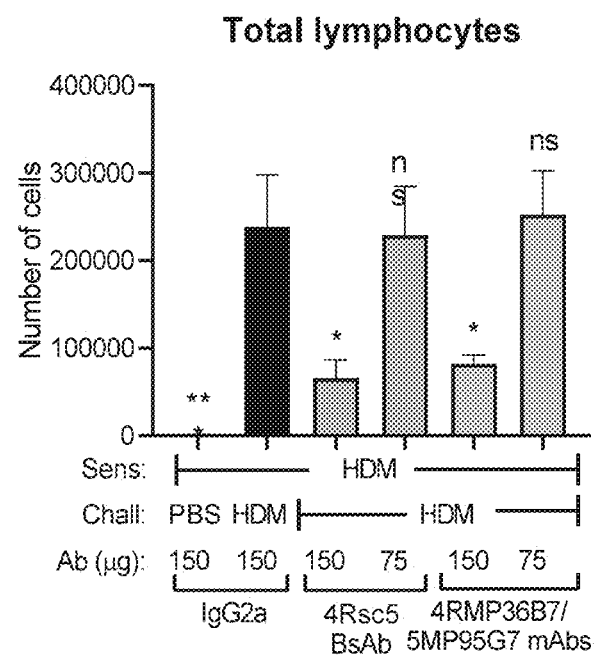

Fig. 24
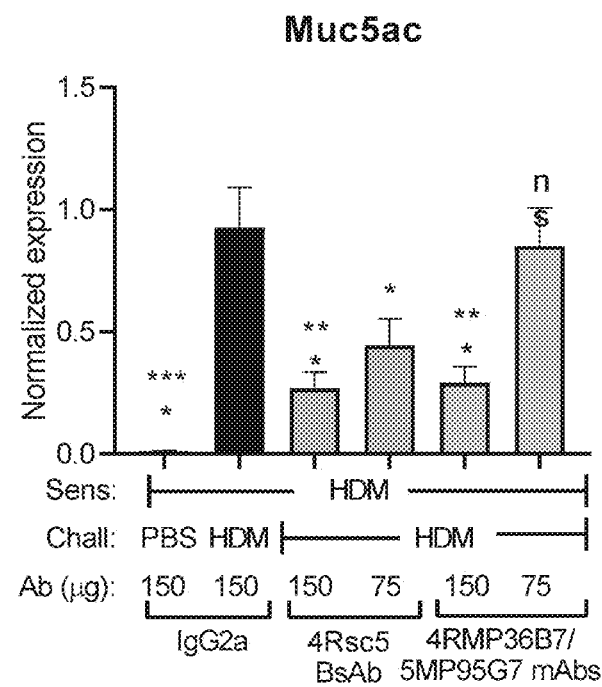
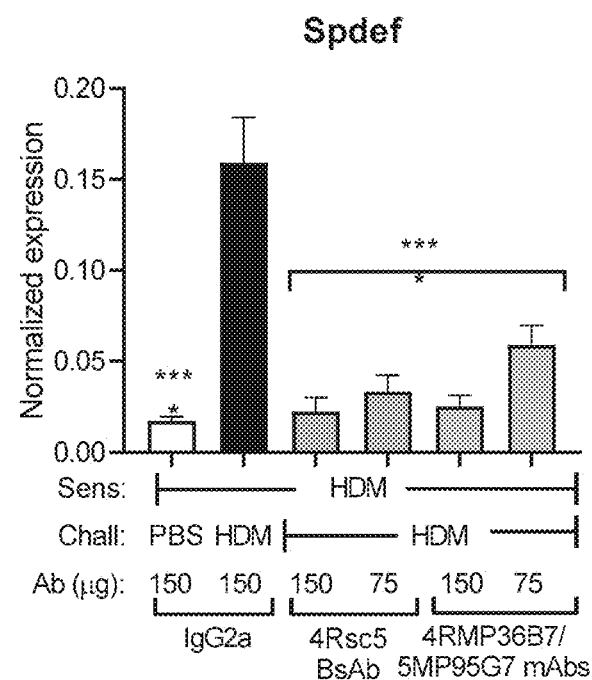

MULTISPECIFIC ANTIBODIES AGAINST IL-5 AND IL-4R

RELATED APPLICATIONS

This application is a 35 U.S.C. § 371 filing of International Patent Application No. PCT/EP2019/053890, filed Feb. 15, 2019, which claims priority to Great Britain Patent Application No. 1802487.7, filed Feb. 15, 2018, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Jul. 30, 2020, is named 609853_AGX5-039US_ST25.txt and is 52,524 bytes in size.

FIELD OF THE INVENTION

The present invention relates to combination therapies and to their use in the treatment of chronic airway disease, particularly use in the treatment of asthma. The combination therapies comprise (i) an antagonist of IL-5:IL-5R and (ii) an antagonist of IL-4:IL-4R and/or an antagonist of IL-13:IL-13R. The antagonists of the combinations may be antibody molecules and preferably, the combination therapies comprise an antibody molecule that binds to IL-4Rα and an antibody molecule that binds to IL-5. The combination therapies typically inhibit signalling via the type 2 cytokines IL-4, IL-13 and IL-5. The present invention also provides bispecific antibodies comprising an antigen binding domain that binds to IL-4Rα and an antigen binding domain that binds to IL-5. The bispecific antibodies may be used for the treatment of chronic airway disease, particularly asthma.

BACKGROUND TO THE INVENTION

Chronic airway diseases (or chronic respiratory diseases) are chronic diseases of the airways and other structures of the lung. Some of the most common forms of chronic airway disease are asthma, and chronic obstructive pulmonary disease, which includes chronic bronchitis and emphysema.

Asthma is a chronic inflammatory disease of the conducting airways that leads to symptoms of coughing, wheezing and chest tightness. It is a disease that affects up to 300 million people worldwide. The airway obstruction that occurs in asthma patients runs a variable course, with symptom-free periods interrupted by periods of exacerbations, often caused by environmental allergens and viral infection. A typical feature is bronchial hyperresponsiveness (BHR), which is the tendency of the airways to constrict in response to stimuli such as cold air and exercise.

Asthmatic patients also exhibit signs of airway remodelling whereby the airway walls thicken and the number of mucus-producing goblet cells in the epithelium or submucosal glands increases, a phenomenon termed goblet cell metaplasia (GCM). Goblet cells produce mucins, which control the viscoelasticity and hydration of the mucus covering the ciliary escalator. In asthmatics, the sputum is often so dry that it can lead to mucus impaction and severe airway obstruction. Currently few therapeutic options exist to reduce GCM and improve mucus clearance.

Historically, treatment approaches for asthma involved the use of non-specific agents such as inhaled corticosteroids and β2-agonists, with varying degrees of success. However, it is now understood that 'asthma' is a heterogeneous disorder that describes multiple phenotypes each presenting with different clinical, physiological and molecular characteristics (Wenzel S E (2015) *Nature Medicine;* 18(5): 716-725; Ray et al. (2015) *Am J Physiol—Lung Cellular and Molecular Physiology;* 308: 130-140).

There have been attempts to group clinical subsets of asthma with the recognition that each may be driven by distinct pathogenic molecular mechanisms, and therefore may have different aetiologies and different responses to therapy (Gauthier et al. (2015) *American Journal of Respiratory and Critical Care Medicine;* 192(6): 660-668). Examples of subsets identified include: early-onset or late-onset asthma, depending on the age the symptoms present themselves; eosinophilic, neutrophilic, or non-inflammatory asthma, depending on the presence and type of inflammation observed; exercise-induced asthma; obesity-related asthma; atopic asthma, which is characterised by an allergic sensitization to inhaled allergens such as house dust mites (HDMs) and an increase in allergen-specific IgE in serum; mild or moderate asthma, which may also be described as corticosteroid responsive; severe asthma; and type 2 cytokine-associated asthma, representing individuals that share a type 2 inflammatory pattern. Importantly, many phenotypes overlap due to a lack of clear demarcation between these groupings, and patients may exhibit clinical or pathologic features of multiple groups, making it difficult to predict individual responsiveness to treatment.

There is a growing understanding of these mechanistically distinct groups, sometimes termed 'endotypes', and relevant cellular or molecular biomarkers are beginning to be identified. In bronchial biopsies or lung-resection samples, asthma is often characterized by accumulation of eosinophils, mast cells and CD4+ T lymphocytes, which produce the type 2 cytokines IL-4 and/or IL-5 in the epithelium and lamina propria. However, this type 2 inflammatory signature is detectable in only 50% of individuals with asthma, particularly those with early onset disease, an atopic predisposition and high blood eosinophil counts. In contrast, in some individuals with asthma, particularly those who respond poorly to steroids, airway infiltrates are composed primarily of neutrophils. These neutrophils are probably recruited to the airways by IL-17-producing cells such as T-helper type 17 lymphocytes or γδT cells (Lambrecht and Hammad (2015) *Nat. Immunol.* 16(1): 45-56).

Drugs specifically targeting molecular pathways implicated in chronic airway disease are currently being developed. For example, a number of antibody therapies have been developed for allergic disease (Sheridan C (2018) *Nature Biotechnology;* 36: 3-5; Godar et al. (2017) *mAbs: Taylor & Francis;* 1-12). These include dupilumab which binds to IL-4Rα, omalizumab which targets IgE, mepolizumab and reslizumab which target IL-5, and tralokinumab which binds IL-13. However, a need exists for improved therapies in this area.

SUMMARY OF THE INVENTION

The present invention is based upon the targeting of multiple type 2 cytokine signalling pathways. Type 2 cytokines were originally so-called because they are released by T helper type 2 cells ($T_H2$ cells). In chronic airway diseases such as asthma, type 2 cytokines are released not only by $T_H2$ cells but also by cells such as basophils, mast cells and eosinophils. Type 2 cytokines play a key role in the pathogenesis of chronic airway disease, particularly asthma. It has surprisingly been found that targeting multiple type II cytokines, particularly IL-5, IL-4 and IL-13, leads to an unexpected synergistic effect in alleviating conditions and symptoms underlying chronic airway disease. The combination therapies of the present invention are thus particularly suitable for the treatment of chronic airway disease.

In a first aspect, the present invention provides a combination comprising: (i) an antagonist of IL-5:IL-5R; and (ii) an antagonist of IL-4:IL-4R and/or an antagonist of IL-13:IL-13R. Since the IL-4 receptor complex and the IL-13 receptor complex share a common subunit, IL-4Rα, an antagonist of IL-4Rα can serve as an antagonist of both the IL-4:IL-4R and IL-13:IL-13R signalling pathways. It follows that in preferred embodiments, the combinations of the present invention comprise an antagonist of IL-5:IL-5R and an antagonist of IL-4Rα. The antagonist of IL-5:IL-5R is preferably an antagonist of IL-5. The combinations may inhibit signalling via IL-5, IL-4 and IL-13.

The antagonists of the combinations may be antibody molecules. Thus, in certain embodiments, the antagonist of IL-5:IL-5R is an antibody molecule and/or the antagonist of IL-4:IL-4R is an antibody molecule and/or the antagonist of IL-13:IL-13R is an antibody molecule. In preferred embodiments, the combinations comprise an antagonist of IL-5:IL-5R that is an antibody molecule that binds to IL-5, preferably human IL-5, and an antagonist of IL-4Rα that is an antibody molecule that binds to IL-4Rα, preferably human IL-4Rα.

In certain embodiments, the antibody molecules of the combinations are independently selected from the group consisting of: an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies or any antigen-binding molecule formed by combination, assembly or conjugation of such antigen binding fragments. In preferred embodiments, the combinations comprise an antibody molecule that binds to IL-4Rα and an antibody molecule that binds to IL-5, wherein the antibody molecules are independently selected from the group consisting of: an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies or any antigen-binding molecule formed by combination, assembly or conjugation of such antigen binding fragments. The antibody molecules of the combinations may be VHH antibodies. In preferred embodiments, the antibody molecules of the combinations are IgG antibodies.

In certain embodiments, the antibody molecules of the combinations, for example the antibody molecule that binds to IL-4Rα and/or the antibody molecule that binds to IL-5, is a humanized or germlined variant of a non-human antibody or an antigen-binding fragment thereof, for example a camelid-derived antibody or an antigen-binding fragment thereof. In certain embodiments, the antibody molecules of the combinations, for example the antibody molecule that binds to IL-4Rα and/or the antibody molecule that binds to IL-5, comprise the CH1 domain, hinge region, CH2 domain and/or CH3 domain of a human IgG. Alternatively, the antibody molecules may exhibit high homology to a human IgG, preferably IgG1.

In certain embodiments, the antibody molecules of the combination, for example the antibody molecule that binds to IL-4Rα and/or the antibody molecule that binds to IL-5, comprise an Fc domain derived from a human IgG, preferably IgG1. The Fc domain may be unmodified or may be modified by one or more amino acid substitutions, for example to increase the binding affinity for FcRn (the neonatal Fc receptor). In preferred embodiments, the antibody molecules may comprise an Fc domain, preferably an Fc domain derived from a human IgG comprising the amino acid substitutions: H433K and N434F; or M252Y, S254T, T256E, H433K and N434F. The numbering of the Fc domain is in accordance with the EU numbering scheme.

In certain embodiments, the antibody molecules of the combinations, for example the antibody molecule that binds to IL-4Rα and/or the antibody molecule that binds to IL-5, exhibit pH-dependent antigen binding activity, in particular exhibit lower antigen-binding activity at acidic pH than at neutral pH. The ratio of antigen-binding activity at acidic pH and at neutral pH as measured by the dissociation constant ratio: KD (at acidic pH)/KD (at neutral pH), may be at least 2.

Regarding the formulation of the combinations, the IL-5:IL-5R and IL-4:IL-4R and/or IL-13:IL-13R antagonists may be co-formulated or provided separately. For embodiments wherein the antagonists are co-formulated, the antagonists may be formulated according to a 1:1 ratio, or may be formulated according to a non-equimolar ratio. For example, for a combination comprising an antagonist of IL-5:IL-5R, preferably an antagonist of IL-5, and an antagonist of IL-4Rα, the antagonists may be formulated according to a ratio of, for example: 1:2 or 2:1.

For embodiments wherein the combination comprises an antagonist of IL-4Rα and an antagonist of IL-5 and the antagonists are antibody molecules, the combination may comprise the antibody molecules combined in a multispecific antibody, for example a bispecific antibody.

In certain embodiments, the combination may comprise one or more additional therapeutic agents.

In a second aspect, the present invention provides a bispecific antibody comprising an antigen binding region that binds to IL-4Rα and an antigen binding region that binds to IL-5. In preferred embodiments, the antigen binding region that binds to IL-4Rα and/or the antigen binding region that binds to IL-5 is a humanised or germlined variant of a non-human antibody or antigen-binding fragment thereof, preferably a camelid antibody or antigen-binding fragment thereof. In certain embodiments, the antigen binding region that binds to IL-4Rα comprises a first variable heavy chain domain (VH) and variable light chain domain (VL) pairing and the antigen binding region that binds to IL-5 comprises a second variable heavy chain domain (VH) and variable light chain domain (VL) pairing. The bispecific antibody may be an IgG antibody having a first VH-VL pairing that binds to IL-4Rα and a second VH-VL pairing that binds to IL-5. In certain embodiments, the bispecific antibody is an IgG antibody having at least one scFv fragment linked thereto.

The bispecific antibodies of the present invention may exhibit pH-dependent antigen binding. For example, the antigen binding region that binds to IL-4Rα and/or the antigen binding region that binds to IL-5 may exhibit lower antigen-binding activity at acidic pH than at neutral pH. In certain embodiments, the ratio of antigen-binding activity at acidic pH and at neutral pH is at least 2 as measured by KD (at acidic pH)/KD (at neutral pH).

Combinations and bispecific antibodies targeting multiple type 2 cytokine signalling pathways have been found to be particularly useful for the treatment of chronic airway disease, particularly asthma. Therefore, a further aspect of the invention provides a combination in accordance with the first aspect of the invention or a bispecific antibody in accordance with the second aspect of the invention for use in the treatment of chronic airway disease in a human subject. Further provided is a method for treating chronic airway disease in a human subject, said method comprising administering to the subject an effective amount of a combination in accordance with the first aspect of the invention or a bispecific antibody in accordance with the second aspect of the invention.

In certain embodiments, the chronic airway disease is selected from: asthma; chronic rhinosinusitis (CRS); immunoglobulin G4-related disease (IgG4-RD); chronic obstructive pulmonary disease (COPD); chronic bronchitis; emphysema; chronic angioedema; diseases characterised by goblet cell metaplasia including Barrett's oesophagus; active eosinophilic esophagitis; nasal polyposis; chronic sinusitis; Churg Strauss Syndrome; allergic bronchopulmonary aspergillosis (ABPA); hypereosinophilic syndrome, bullous pemphigoid and cystic fibrosis.

The chronic airway disease to be treated in accordance with the present methods may be characterised by increased mucus production or increased bronchial hyperresponsiveness. In preferred embodiments, the chronic airway disease to be treated is asthma, optionally severe asthma, severe refractory asthma, Type II High asthma, atopic or allergic asthma.

The methods described herein may serve to treat chronic airway disease, preferably asthma, by decreasing goblet cell metaplasia (or GCM). Alternatively or in addition, the methods may serve to treat chronic airway disease, preferably asthma, by decreasing bronchial hyperresponsiveness (BHR). The methods may comprise additional steps, for example further administering to the patient one or more additional therapeutic agents to treat the chronic airway disease.

BRIEF DESCRIPTION OF THE DRAWINGS

FIG. 1 shows the neutralizing activity of both IL-4Rα and IL-5 monospecific Abs as assessed in an in vitro cellular assay of IL-4 induced proliferation of HT-2 cells, and IL-5 induced proliferation of TF-1 cells. IL-4Rα (square) and IL-5 (triangle) monospecific Abs potently inhibited mouse IL-4 and IL-5-induced HT-2 and TF-1 cell proliferation, respectively. Results are expressed as mean of triplicates±SEM of two independent experiments.

FIG. 2 is a representative surface plasmon resonance (SPR) sensorgram of the interaction between the mAbs (IL-4Rα Ab, IL-5 Ab, or irrelevant IgG2a Ab) at varying concentrations (0-20 µg/mL) and the immobilized target (IL-4Rα or IL-5).

FIG. 4 shows MHC class II antigens of purified B cells, before and after IL-4Rα mAb treatment, as analysed by FACS. IL-4Rα mAb potently inhibited IL-4 induced-MHC class II antigens of purified B cells.

FIG. 5A is a diagrammatic representation of the experimental setup using the house dust mite (HDM) mouse model. IL-4Rα and IL-5 antibody treatments were delivered by injection to HDM-treated C57BL/6J mice during both the sensitization and challenge phases. FIG. 5B shows bronchealveolar lavage (BAL) differential cell counts of mice that received IL-4Rα monospecific Ab, IL-5 monospecific Ab, a combination of the IL-4α/IL-5 monospecific Abs, or an irrelevant IgG2a Ab, as analysed by FACS. Eosinophil cell counts were increased by allergen challenge in IgG2a treated HDM-sensitized mice. A significant reduction in eosinophil cell counts was observed after treatment with IL-4Rα monospecific Abs, IL-5 monospecific Abs, and after treatment with the combination of the IL-4α/IL-5 monospecific Abs, as compared to treatment with a control IgG2a Ab. P values reflect the one-way ANOVA test, ns: not significant, *P≤0.05, P≤0.01, *P≤0.001, ****P≤0.0001 versus a control IgG≤2 Ab.

FIG. 8 shows production of IL-5 and IL-13 cytokines by mesenteric lymph node (MLN) cells re-stimulated with HDMs for three days ex vivo, as determined by ELISA. The in vitro production of effector cytokines IL-5 and IL-13 in allergen-re-stimulated cultures of MLN cells was boosted by allergen challenge in IgG2a treated HDM-sensitized mice. However, this response was significantly decreased after treatment with IL-4Rα monospecific Ab and a combination of both monotherapies. P values reflect the one-way ANOVA test, ns: not significant, P≤0.01, *P≤0.001 versus a control IgG2a Ab.

FIG. 10A shows MucSAC confocal staining in mouse lungs after treatment with IL-4Rα monospecific Ab, IL-5 monospecific Ab, combined IL-4Rα/IL-5 monospecific Abs, or an irrelevant IgG2a Ab. FIG. 10B shows lung mRNA expression levels of MucSac and Agr2 determined by qRT-PCR. The mRNA expression levels of these two genes were induced by HDM challenge in mice compared to PBS challenge. The IL-4Rα and IL-5 antibodies alone did not significantly reverse this increase in MucSac or Agr2 mRNA levels. However, the combination of both monospecific IL-4Rα mAb and an IL-5 mAb, significantly reduced the HDM-mediated increase in MucSac or Agr2 mRNA levels. P values reflect the one-way ANOVA test, ns: not significant, P≤0.01, **P≤0.0001, versus an irrelevant IgG2 Ab.

FIG. 13A. SPR signals were measured after sequential injection of IL-4Rα monospecific Ab or IL-4Rα/IL-5 bispecific Ab, followed by a $2^{nd}$ injection of IL-4Rα-Fc or IL-5, on coated IL-4Rα-Fc. One arm of the bispecific bound to coated IL-4Rα, and the other arm bound to injected IL-5. FIG. 13B SPR signals were measured after sequential injection of IL-5 monospecific Ab or IL-4Rα/IL-5 bispecific Ab, followed by a $2^{nd}$ injection of IL-4Rα-Fc or IL-5, on coated IL-5. One arm of the bispecific bound to coated IL-5, and the other arm bound to injected IL-4Rα.

FIG. 14 is a diagrammatic representation of an experimental setup wherein antibody treatments were injected in HDM-treated C57BL/6J mice only during the challenge phase. To compare equimolar inhibition of targets, and to eliminate differences in the total amount of Ab, the following doses of antibody were administered to each mouse: 75 μg of each monospecific Ab combined with 75 μg of an irrelevant IgG2a Ab; 75 μg of each monospecific Abs injected in combination; or 150 μg of the IL-4Rα/IL-5 bispecific Ab.

FIG. 16 shows production of IL-5 and IL-13 cytokines by mesenteric lymph node (MLN) cells re-stimulated with HDMs for three days ex vivo, as determined by ELISA. P values reflect the one-way ANOVA test, ns: not significant, *P≤0.001, **P≤0.0001 versus an irrelevant IgG2 Ab.

FIG. 22 is a diagrammatic representation of an experimental setup using a house dust mite (HDM) mouse model as an in vivo murine model of asthma. IL-4Rα and IL-5 antibody treatments were delivered by injection to HDM-treated C57BL/6J mice only during the challenge phase.

FIG. 23 shows BAL differential cell counts of HDM-treated mice that received combined IL-4Rα/IL-5 monospecific Abs, IL-4Rα/IL-5 bispecific Ab (Bs 4Rsc5), or an irrelevant IgG2a Ab, as analysed by FACS. HDM challenge in sensitized mice increased the number of eosinophils and Lymphocytes in the BAL fluid. This increase in cell number was significantly decreased after the injections in mice receiving the combination of both monospecific IL-4Rα and IL-5 Abs, and in mice receiving the IL-4Rα/IL-5 bispecific Abs. P values reflect the one-way ANOVA test, ns: not significant, *P≤0.001, **P≤0.0001 versus an irrelevant IgG2 Ab.

DETAILED DESCRIPTION

A. Definitions

Figure 3:
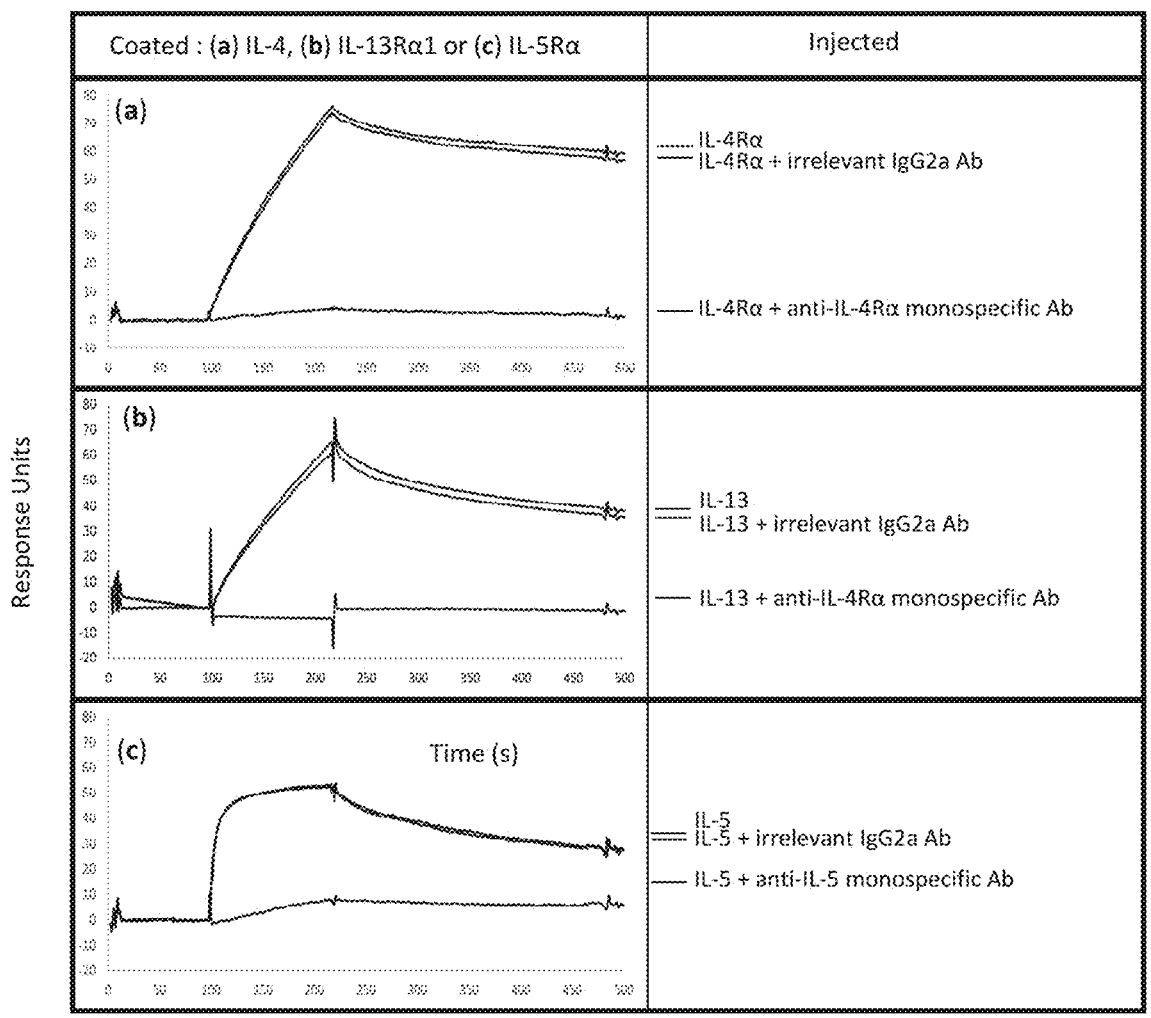
FIG. 3 is a representative SPR sensorgram of the interactions between a mixture composed of a mAb (IL-4Rα Ab, IL-5 Ab or irrelevant IgG2a Ab) and its target (IL-4Rα or IL-5), and the immobilized proteins (IL-4, IL-13Rα or IL-5Rα).

Unless defined otherwise, all technical and scientific terms used herein have the same meaning as is commonly understood by one skilled in the art in the technical field of the invention.

"Combination therapy"—As used herein, the term "combination therapy" refers to a treatment in which a subject, for example a human subject, is given two or more therapeutic agents. The "combinations" of the present invention are for use as "combination therapies". The two or more therapeutic agents are typically administered so as to treat a single disease, herein a chronic airway disease. The combinations or combination therapies of the present invention combine antagonists targeting multiple type 2 cytokine signalling pathways. In particular, the combination therapies described herein target the cytokine:cytokine receptors: IL-5:IL-5R; IL-4:IL-4R and the IL-13:IL-13R. These cytokine—cytokine receptors are described in more detail herein. In preferred embodiments, the antagonists are antibody molecules that bind specifically to their respective cytokine or cytokine receptor targets. As described elsewhere herein, the antagonists included in the combination therapies may be co-formulated or may be provided separately, for example as separate compositions, for administration to a subject or patient in need thereof. For embodiments wherein the combination comprises an antibody molecule that binds to IL-4Rα and an antibody molecule that binds to IL-5, the antibody molecules of the combination may be comprised within a single antibody, for example a multispecific antibody format such as a bispecific antibody.

"Antagonist"—As used herein, the term "antagonist" means any agent or molecule capable of inhibiting the function of its target cytokine or cytokine receptor. As used herein, an antagonist of IL-5:IL-5R means any agent or molecule capable of inhibiting the signalling initiated by IL-5 binding to its cognate receptor complex, "IL-5R". As used herein, an antagonist of IL-4:IL-4R means any agent or molecule capable of inhibiting the signalling initiated by IL-4 binding to its cognate type I receptor complex, "IL-4R". As used herein, an antagonist of IL-13:IL-13R means any agent or molecule capable of inhibiting the signalling initiated by IL-13 binding to its cognate receptor complex, "IL-13R". As explained elsewhere herein, the receptor complexes to which the type 2 cytokines IL-5; IL-4 and IL-13 bind typically consist of two receptor sub-units. An antagonist of IL-5:IL-5R, for example, may prevent association between IL-5 and its receptor complex or prevent association between the two subunits of the IL-5R complex (IL-5Rα and βc), such that signalling mediated by IL-5 is inhibited or blocked. Similarly, an antagonist of IL-4:IL-4R or an antagonist of IL-13:IL-13R may prevent association between the cytokine (IL-4 or IL-13) and its receptor complex or prevent association between the two subunits of the IL-4R or IL-13R complex, such that signalling mediated by IL-4 or IL-13 is inhibited or blocked. As explained elsewhere herein, the IL-4R and IL-13R complexes share a common receptor subunit, IL-4Rα. Furthermore, the cytokine IL-4 can signal not only via its own type I receptor complex "IL-4R", but also via the IL-13R complex. It follows that an antagonist of IL-4Rα can disrupt both the IL-4R and IL-13R complexes so as to inhibit signalling via both IL-4 and IL-13. Furthermore, in some cases, an antagonist of the IL-13R complex may inhibit signalling via IL-4.

IL-5:IL-5R, IL-4:IL-4R and IL-13:IL-13R antagonists for use in the combinations of the present invention may take the form of any suitable agent or molecule. In certain embodiments, the antagonist may inhibit the function of its target by down-regulating the expression of the target, for example the expression of IL-4Rα or IL-5. In alternative embodiments, the antagonist may inhibit the function of its target by binding directly to the cytokine or a receptor subunit. As explained herein, an antagonist of IL-5:IL-5R may bind to the cytokine IL-5 (referred to as an antagonist of IL-5) or to one of the IL-5R subunits (referred to as an antagonist of IL-5Rα or an antagonist of βc). Similarly, an antagonist of IL-4:IL-4R may bind to the cytokine IL-4 (referred to as an antagonist of IL-4) or to one of the type I IL-4R subunits (referred to as an antagonist of IL-4Rα or an antagonist of γc).

In preferred embodiments, the antagonist is specific for its target. For example, an antagonist of IL-4Rα (or IL-4Rα antagonist) will preferentially inhibit the function of IL-4Rα as compared with other molecular targets. An IL-5 antagonist will preferentially inhibit the function of IL-5 as compared with other molecular targets. The antagonists will typically achieve the required level of specificity by interacting directly with their target, for example by selectively binding to IL-4Rα or IL-5 mRNA or protein. Suitable agents or molecules that may serve as antagonists include but are not limited to inhibitory RNA species, for example siRNAs or shRNAs, small molecule inhibitors, biological antagonists. In preferred embodiments, the antagonists of the combination are antibody molecules. "Antibody molecule"—As used herein, the term "antibody molecule" is intended to encompass full-length antibodies and antigen binding fragments thereof, including variants such as modified antibodies, humanized antibodies, germlined antibodies and antigen binding fragments thereof. The term "antibody" typically refers to a heterotetrameric immunoglobulin polypeptide having a combination of two heavy and two light chains wherein the polypeptide has significant specific immunoreactive activity to an antigen of interest (for example IL-4Rα or IL-5). For antibodies of the IgG class, the antibodies comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region. The light chains of an antibody are classified as either kappa or lambda (κ,λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. The term "antibody molecule" as used herein encompasses full-length antibodies or antigen binding fragments thereof from any class or subclass of antibody.

The term "antibody molecule" as used herein is also intended to encompass "Heavy-chain only antibodies" or "VHH antibodies". The term "heavy-chain only antibody" or "VHH antibody" refers to a type of antibody produced only by species of the Camelidae family, which includes camels, llama, alpaca. Heavy chain-only antibodies are composed of two heavy chains and are devoid of light chains. Each heavy chain has a variable domain at the N-terminus, and these variable domains are referred to as "VHH" domains in order to distinguish them from the variable domains of the heavy chains of the conventional heterotetrameric antibodies i.e. the VH domains, described above.

With respect to antigen binding fragments encompassed within the generic term "antibody molecule", these fragments are parts or portions of a full-length antibody or antibody chain comprising fewer amino acid residues than an intact or complete antibody whilst retaining antigen binding activity. The term "antibody molecule" as used herein is intended to encompass antigen binding fragments selected from: an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies or any antigen-binding molecule formed by combination, assembly or conjugation of such antigen binding fragments. The term "antibody molecule" as used herein is further intended to encompass antibody fragments selected from the group consisting of: unibodies; domain antibodies; and nanobodies. Fragments can be obtained, for example, via chemical or enzymatic treatment of an intact or complete antibody or antibody chain or by recombinant means.

"Variable region" or "variable domain"—The terms "variable region" and "variable domain" are used herein interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(A), L2(A) and L3(A) and may be defined as comprising residues 24-33 (L1(A), consisting of 9, 10 or 11 amino acid residues), 49-53 (L2(A), consisting of 3 residues) and 90-96 (L3(A), consisting of 5 residues) in the VL domain (Morea et al., Methods 20:267-279 (2000)). The first, second and third hypervariable loops of the VKappa light chain domain are referred to herein as L1(K), L2(K) and L3(K) and may be defined as comprising residues 25-33 (L1(K), consisting of 6, 7, 8, 11, 12 or 13 residues), 49-53 (L2(K), consisting of 3 residues) and 90-97 (L3(K), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., *Methods* 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Constant region"—As used herein, the term "constant region" refers to the portion of the antibody molecule outside of the variable domains or variable regions. Immunoglobulin light chains have a single domain "constant region", typically referred to as the "CL or CL1 domain". This domain lies C terminal to the VL domain. Immunoglobulin heavy chains differ in their constant region depending on the class of immunoglobulin (γ, μ, α, δ, ε). Heavy chains γ, α and δ have a constant region consisting of three immunoglobulin domains (referred to as CH1, CH2 and CH3) with a flexible hinge region separating the CH1 and CH2 domains. Heavy chains μ and ε have a constant region consisting of four domains (CH1-CH4). The constant domains of the heavy chain are positioned C terminal to the VH domain.

The numbering of the amino acids in the heavy and light immunoglobulin chains run from the N-terminus at the forked ends of the Y configuration to the C-terminus at the bottom of each chain. Different numbering schemes are used to define the constant domains of the immunoglobulin heavy and light chains. In accordance with the EU numbering scheme, the heavy chain constant domains of an IgG molecule are identified as follows: CH1—amino acid residues 118-215; CH2—amino acid residues 231-340; CH3—amino acid residues 341-446. In accordance with the Kabat numbering scheme, the heavy chain constant domains of an IgG molecule are identified as follows: CH1—amino acid residues 114-223; CH2—amino acid residues 244-360; CH3—amino acid residues 361-477. The "Fc domain" or "Fc region" typically defines the portion of the constant region of a heavy chain including the CH2 and CH3 domains. The Fc region may also include some residues from the hinge region. The "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux K. H. et al. J. Immunol. 161:4083-90 1998). Antibodies of the invention comprising a "fully human" hinge region may contain one of the hinge region sequences shown in Table 2 below.

TABLE 2

| Human hinge sequences | | | |
|---|---|---|---|
| IgG | Upper hinge | Middle hinge | Lower hinge |
| IgG1 | EPKSCDKTHT (SEQ ID NO: 80) | CPPCP (SEQ ID NO: 81) | APELLGGP (SEQ ID NO: 82) |
| IgG3 | ELKTPLGDTTHT (SEQ ID NO: 83) | CPRCP (EPKSCDTPPPCPRCP)$_3$ (SEQ ID NO: 84) | APELLGGP (SEQ ID NO: 82) |
| IgG4 | ESKYGPP (SEQ ID NO: 85) | CPSCP (SEQ ID NO: 86) | APEFLGGP (SEQ ID NO: 87) |
| IgG2 | ERK (SEQ ID NO: 88) | CCVECPPPCP (SEQ ID NO: 89) | APPVAGP (SEQ ID NO: 90) |

"Specificity" and "Multispecific antibodies"—The antibody molecules for use in the combination therapies described herein bind to particular target antigens. It is preferred that the antibody molecules "specifically bind" to their target antigen, wherein the term "specifically bind" refers to the ability of any antibody molecule to preferentially immunoreact with a given target e.g. IL-4Rα and IL-5. The antibody molecules of the present combinations and methods may be monospecific and contain one or more binding sites which specifically bind a particular target. The antibody molecules of the present combinations and methods may be incorporated into "multispecific antibody" formats, for example bispecific antibodies, wherein the multispecific antibody binds to two or more target antigens. For example, in one embodiment, the combination of the present invention comprises a bispecific antibody comprising a first antibody molecule specifically binding to IL-4Rα and a second antibody molecule specifically binding to IL-5. In order to achieve multiple specificities, "multispecific antibodies" are typically engineered to include different combinations or pairings of heavy and light chain polypeptides with different VH-VL pairs. Multispecific, notably bispecific antibodies, may be engineered so as to adopt the overall conformation of a native antibody, for example a Y-shaped antibody having Fab arms of different specificities conjugated to an Fc region. Alternatively multispecific antibodies, for example bispecific antibodies, may be engineered so as to adopt a non-native conformation, for example wherein the variable domains or variable domain pairs having different specificities are positioned at opposite ends of the Fc region.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. scFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

"Humanising substitutions"—As used herein, the term "humanising substitutions" refers to amino acid substitutions in which the amino acid residue present at a particular position in the VH or VL domain of an antibody is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of the antibodies, defined herein.

"Humanised variants"—As used herein the term "humanised variant" or "humanised antibody" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Germlined variants"—The term "germlined variant" or "germlined antibody" is used herein to refer specifically to "humanised variants" in which the "humanising substitutions" result in replacement of one or more amino acid residues present at (a) particular position(s) in the VH or VL domain of an antibody with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

"Affinity variants"—As used herein, the term "affinity variant" refers to a variant antibody which exhibits one or more changes in amino acid sequence compared to a reference antibody, wherein the affinity variant exhibits an altered affinity for the target antigen in comparison to the reference antibody. For example, affinity variants will exhibit a changed affinity for a target, for example IL-4Rα or IL-5, as compared to the reference IL-4Rα or IL-5 antibody. Preferably the affinity variant will exhibit improved affinity for the target antigen, as compared to the reference antibody. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"IL-5:IL-5R"—As used herein, the term "IL-5" refers to the interleukin-5 cytokine and the term "IL-5R" refers to the receptor complex to which the interleukin 5 cytokine binds. The term "IL-5:IL-5R" is used herein to indicate the IL-5 cytokine/cytokine receptor signalling complex. Cytokine IL-5 is also known as B-cell differentiation factor I, eosinophil differentiation factor, and T-cell replacing factor (TRF). The human homolog of IL-5 is 134 amino acids in length (http://www.uniprot.org/uniprot/P05113). The term "IL-5" as used herein is intended to encompass any splice variants of the protein. Monomeric IL-5 has no activity, and a homodimer is required for function. One IL-5 homodimer engages one IL-5 receptor (IL-5R). The receptor for IL-5 consists of two subunits. The first subunit is the "IL-5 receptor subunit alpha" or "IL-5Rα", which is also known as IL-SR-alpha, IL-SRA, CDw125 and CD antigen: CD125; this subunit forms the ligand binding part of the receptor complex. The human homolog of IL-5Rα is 420 amino acids in length (http://www.uniprot.org/uniprot/Q01344). The second subunit of the IL-5R complex is the non-ligand binding common signal transducing beta subunit or beta chain (βc). IL-5 is secreted by a restricted number of mesenchymal cell types. Cells known to express IL-5 include eosinophils, NK cells, TC2 CD8+ T cells, mast cells, CD45+CD4+ T cells, gamma delta T cells and IL-1 beta activated endothelial cells. IL-5 is known to regulate expression of genes involved in proliferation, cell survival and maturation and effector functions of B cells and eosinophils.

"IL-4:IL-4R"—As used herein the term "IL-4" refers to the interleukin-4 cytokine and the term "IL-4R" refers to the type I receptor complex to which the interleukin 4 cytokine binds. The term "IL-4:IL-4R" is used to indicate the IL-4 cytokine/type I cytokine receptor signalling complex. Cytokine IL-4 is also known as B-cell stimulatory factor 1 (BSF-1), Binetrakin and Lymphocyte stimulatory factor 1. The human homolog of IL-4 is 153 amino acids in length (http://www.uniprot.org/uniprot/P05112). The term "IL-4" as used herein is intended to encompass any splice variants of the protein. The type I receptor for IL-4 consists of two subunits. The first subunit is the "IL-4Rα", also known as the interleukin-4 receptor subunit alpha, interleukin-4 binding subunit, and CD124. IL-4Rα is a widely expressed 140 kDa transmembrane glycoprotein in the class I cytokine receptor family. The human homolog of IL-4Rα is 825 amino acids in length (http://www.uniprot.org/uniprot/P24394). The term "IL-4Rα" as used herein is intended to encompass any splice variants of the protein. In the type I IL-4 receptor complex, IL-4Rα associates with a second subunit, the common gamma chain (γc), and the γc subunit increases the affinity of IL-4Rα for IL-4 to effect downstream signalling via IL-4. The IL-4 receptor complex is present, for example, in B-cells, T-cells, monocytes, eosinophils, and fibroblasts and the IL-4Rα couples to the JAK1/2/3-STAT6 pathway. The IL-4 response is involved in promoting Th2 differentiation, and regulating IgE production and chemokine and mucus production at sites of allergic inflammation.

"IL-13:IL-13R"—As used herein the term "IL-13" refers to the interleukin-13 cytokine and the term "IL-13R" refers to the receptor complex to which the interleukin 13 cytokine binds. The IL-13 receptor also serves as the type II receptor for IL-4. The term "IL-13:IL-13R" is used to indicate the IL-13 cytokine/cytokine receptor signalling complex. The human homolog of IL-13 is 146 amino acids in length (http://www.uniprot.org/uniprot/P35225). The term "IL-13" as used herein is intended to encompass any splice variants of the protein. The receptor for IL-13 consists of two subunits. The first subunit is the "IL-4Rα", also known as the interleukin-4 receptor subunit alpha, interleukin-4 binding subunit, and CD124. As noted above, this subunit is common to both the IL-4 and IL-13 receptors. In the IL-13 receptor complex, IL-4Rα associates with a second subunit, Interleukin-13 receptor subunit alpha 1 or "IL-13R alpha 1" or "IL-13Rα1" or "IL-13RA1". This second subunit serves as the ligand binding subunit for IL-13. The IL-13R complex consisting of the IL-4Rα and IL-13Rα1 subunits is responsive to IL-13 (via binding to IL-13Rα1) and IL-4 (via binding to IL-4Rα), and cytokine binding to this receptor complex initiates signalling via the JAK1/2/3-STAT6 pathway. Similar to the IL-4:IL-4R complex, signalling via the IL-13R complex consisting of the IL-4Rα and IL-13Rα1 subunits is involved in regulating IgE production and chemokine and mucus production at sites of allergic inflammation. Additional information relating to the IL-4 and IL-13 cytokine-receptor signalling pathways can be found, for example, in McCormick and Heller (2015) Cytokine 75(1): 38-50, the contents of which are incorporated herein in their entirety.

"Chronic airway disease"—As used herein, the term "chronic airway disease" may be used interchangeably with 'chronic respiratory disease (CRD)' and is intended to mean any disease of the airways and other structures of the lung. Some of the most common forms of chronic airway disease are chronic obstructive pulmonary disease (COPD), asthma, occupational lung diseases and pulmonary hypertension. In addition to tobacco smoke, other risk factors include air pollution, occupational chemicals and dusts, and frequent lower respiratory infections during childhood. Other chronic airway diseases may include but are not limited to: chronic rhinosinusitis (CRS), immunoglobulin G4-related disease (IgG4-RD), chronic bronchitis, emphysema, chronic angioedema, goblet cell metaplasia specific diseases such as Barrett's oesophagus, active eosinophilic esophagitis, nasal polyposis, chronic sinusitis, Churg Strauss Syndrome, allergic bronchopulmonary aspergillosis (ABPA), hypereosinophilic syndrome, bullous pemphigoid, and cystic fibrosis.

"Asthma"—As used herein, "asthma" is intended to mean any disease or condition relating to inflammation of the air passages in the lungs. Typically the inflammation affects the sensitivity of the nerve endings in the airways so that they become easily irritated. During an asthma attack, the lining of the passages swell causing the airways to narrow and reducing the flow of air in and out of the lungs. Asthma is a heterogeneous disorder that describes multiple phenotypes each presenting with different clinical, physiological and molecular characteristics. Exemplary asthma subtypes may include severe asthma, severe refractory asthma, mild or moderate asthma, obesity-related asthma, exercise-induced asthma, aspirin-induced asthma, atopic or allergic asthma, eosinophilic asthma, neutrophilic asthma, paucigranulocytic or non-inflammatory asthma, early onset asthma, late-onset asthma, type II high asthma, type II low asthma, and type I/Th17 asthma.

B. Combination Therapy to Inhibit Type 2 Cytokine Signalling

The present invention relates to combinations or combination therapies and their use in the treatment of chronic airway disease, particularly in the treatment of asthma. The combinations of the present invention comprise antagonists targeting type 2 cytokines and/or their respective receptors. The cytokines and cytokine receptors targeted by the combinations of the present invention include IL-5 and its receptor IL-5R; IL-4 and its type I receptor IL-4R; and IL-13 and its receptor IL-13R.

In a first aspect, the present invention provides a combination comprising: (i) an antagonist of IL-5:IL-5R; and (ii) an antagonist of IL-4:IL-4R and/or an antagonist of IL-13:IL-13R. In one embodiment, the combination comprises an antagonist of IL-5:IL-5R and an antagonist of IL-4:IL-4R. In a further embodiment, the combination comprises an antagonist of IL-5:IL-5R and an antagonist of IL-13:IL-13R. In a yet further embodiment, the combination comprises an antagonist of IL-5:IL-5R, an antagonist of IL-4:IL-4R and an antagonist of IL-13:IL-13R. In certain embodiments, the combinations inhibit signalling via IL-5 and IL-4. In certain embodiments, the combinations inhibit signalling via IL-5 and IL-13. In preferred embodiments, the combinations inhibit signalling via IL-5, IL-4 and IL-13.

Without wishing to be bound by theory, the combinations of the present invention are thought to be particularly effective in the treatment of chronic airway disease, particularly asthma, by virtue of the combined effect in blocking type 2 cytokine activity. IL-4, IL-13 and IL-5 are type 2 cytokines and the combinations of the invention can inhibit signalling via all three of these cytokines. The "type 2 immune response" refers to immune responses that are mainly regulated by subpopulations of CD4+ T cells known as T helper ($T_H2$) cells. However, airway type 2 immune responses may also be mediated by eosinophils, mast cells, basophils, $T_H2$ cells, group 2 innate lymphoid cells (ILC2s) and IgE-producing B cells.

IL-4, IL-13 and IL-5 are responsible for IgE production by B cells, eosinophil activation and recruitment, and mucus production. Type 2 cytokines drive a cascade of downstream events, including activation of airway epithelial cells, chemo-attraction of effector cells (mast cells, eosinophils, and basophils), and remodelling of the epithelium and sub-epithelial matrix. In chronic airway diseases, for example asthma, aberrant signalling via IL-4, IL-13 and IL-5 can result in airway eosinophilia, airway remodelling, and bronchial hyperresponsiveness (see Lambrecht and Hammad (2015) ibid). The relevant remodelling changes may include smooth muscle cell changes (hyperplasia and hypertrophy), mucus cell changes (goblet cell metaplasia), and vascular remodelling. Together, these inflammatory and pathologic changes in the airway predispose an individual to exaggerated responses to inhaled exacerbants.

The present inventors have shown that by blocking signalling via IL-4, IL-13 and IL-5, a surprising synergistic effect is observed. This effect is seen relative to treatment with an IL-4Rα monotherapy that blocks only IL-4 and IL-13, or an IL-5 monotherapy that blocks only IL-5. The data provided herein show that combination therapies of the present invention, comprising antagonists targeting the IL-5:IL-5R signalling axis and antagonists targeting the IL-4:IL-4R and/or IL-13:IL-13R signalling axis produce a synergistic effect. This effect is seen at the level of decreased mucin production (indicative of goblet cell metaplasia) and at the level of decreased bronchial hyperresponsiveness in an in vivo model of chronic airway disease. Importantly, combination therapies in accordance with the present invention, comprising antagonists targeting type 2 cytokines, have been shown to completely prevent bronchial hyperresponsiveness in an in vivo model.

The combinations of the invention comprise antagonists targeting (i) IL-5:IL-5R; and (ii) IL-4:IL-4R and/or IL-13:IL-13R. As described herein, the term "antagonist" is used in a broad sense to mean any agent or molecule capable of inhibiting the function of its target. For example, an IL-5:IL-5R antagonist will inhibit the function of the IL-5 cytokine-IL-5 receptor complex such that signalling via IL-5 is inhibited. Similarly, an IL-4:IL-4R antagonist will inhibit the function of the IL-4 cytokine-IL-4 receptor complex such that signalling via IL-4 is inhibited. Likewise, an IL-13:IL-13R antagonist will inhibit the function of the IL-13 cytokine-IL-13 receptor complex such that signalling via IL-13 is inhibited.

Antagonists of the type 2 cytokine-receptor pairings described herein, namely antagonists of IL-5:IL-5R, IL-4:IL-4R and IL-13:IL-13R, will typically target or interact with one component of the cytokine-receptor complex. For example, an antagonist of IL-5:IL-5R may interact with IL-5 so as to inhibit signalling via the IL-5:IL-5R signalling pathway. Alternatively, the antagonist of IL-5:IL-5R may interact with receptor subunit IL-5Rα so as to inhibit signalling via the IL-5:IL-5R signalling pathway. In preferred embodiments, the antagonist of IL-5:IL-5R is an antagonist of IL-5. Similarly, the antagonist of IL-4:IL-4R and the antagonist of IL-13:IL-13R may interact with the cytokines, IL-4 and IL-13, respectively, or may interact with the receptor subunits so as to inhibit IL-4 and/or IL-13 signalling, respectively.

It is particularly preferred for the combinations of the invention to comprise an antagonist of the receptor subunit IL-4Rα. More preferably, the combinations comprise an antagonist of IL-5 and an antagonist of IL-4Rα. The reason why it is preferable to target IL-4Rα is because this receptor subunit forms part of the type I receptor complex for IL-4 (together with γc) and also part of the IL-13 receptor complex (together with IL-13Rα1). It follows that an antagonist of IL-4Rα can simultaneously act as an antagonist of IL-4:IL-4R and IL-13:IL-13R thereby inhibiting signalling via both IL-4 and IL-13. In particular, a combination comprising an antagonist of IL-5:IL-5R, preferably an antagonist of IL-5, and an antagonist of IL-4Rα can inhibit signalling via IL-5, IL-4 and IL-13. The antagonists of the combinations described herein preferably bind to their respective human targets.

In preferred embodiments, the antagonists of IL-5:IL-5R, IL-4:IL-4R and/or IL-13:IL-13R are antibody molecules. More preferably, the combinations comprise an antibody molecule that binds to IL-5 and an antibody molecule that binds to IL-4Rα.

In certain embodiments, the combinations comprise, as an IL-5:IL-5R antagonist, an antibody molecule that binds to IL-5. Alternatively, the combinations may comprise, as an IL-5:IL-5R antagonist, an antibody molecule that binds to IL-5Rα. IL-5 and IL-5R antibody molecules that may be incorporated into the combinations described herein include any suitable IL-5 and IL-5Rα antibodies known to those skilled in the art. Exemplary antibodies include mepolizumab (Nucala®) and reslizumab (Cinquair®), which bind to IL-5 and benralizumab (Fasenra®), which binds to IL-5R·

In certain embodiments, the combinations comprise, as an IL-4:IL-4R antagonist, an antibody molecule that binds to IL-4. In certain embodiments, the combinations comprise, as an IL-13:IL-13R antagonist, an antibody molecule that binds to IL-13. In preferred embodiments, the combinations comprise an antibody molecule that binds to IL-4Rα. As noted above, this antagonist serves as an antagonist of both IL-4:IL-4R and IL-13:IL-13R since the IL-4Rα subunit is common to both the IL-4 and IL-13 receptor complexes. Antibody molecules targeting the IL-4 and IL-13 signalling pathways that may be incorporated into the combinations described herein include any suitable IL-4, IL-13, IL-4Rα and IL-13Rα1 antibodies known to those skilled in the art. Such antibodies include dupilumab (Dupixent®), which is a fully humanized mAb to the IL-4Rα receptor. See also: Sheridan C. (2018) Nat. Biotechnol. 36(1): 3-5.

The antibody molecules of the present combinations, for example, the antibody molecules that bind IL-4Rα and the antibody molecules that bind IL-5, may be selected from any suitable antibody molecules displaying immunoreactivity for their respective targets. As noted above, the term "antibody molecule" is used herein to mean full-length antibodies in addition to antigen binding fragments thereof.

The antibodies of the combinations described herein are intended for human therapeutic use and therefore, will typically be of the IgA, IgD, IgE, IgG, IgM type, often of the IgG type, in which case they can belong to any of the four sub-classes IgG1, IgG2a and b, IgG3 or IgG4. In preferred embodiments, the antibody molecules of the combinations are IgG antibodies, optionally IgG1 antibodies. The antibodies may be monoclonal, polyclonal, multispecific (e.g. bispecific antibodies) antibodies, provided that they exhibit the appropriate immunological specificity for their target. Monoclonal antibodies are preferred since they are highly specific, being directed against a single antigenic site.

The antigen binding fragments of the combinations described herein will typically comprise a portion of a full-length antibody, generally the antigen binding or variable domain thereof. Examples of antibody fragments include Fab, Fab', F(ab')2, bi-specific Fab's, and Fv fragments, linear antibodies, single-chain antibody molecules, a single chain variable fragment (scFv) and multispecific antibodies formed from antibody fragments (see Holliger and Hudson (2005) *Nature Biotechnol.* 23:1126-36, incorporated herein by reference).

The antibody molecules of the combinations described herein may exhibit high human homology. Such antibody molecules having high human homology may include antibodies comprising VH and VL domains of native non-human antibodies which exhibit sufficiently high % sequence identity to human germline sequences. In certain embodiments, the antibody molecules are humanised or germlined variants of non-human antibodies. In certain embodiments, the antibody molecules of the combinations described herein may be camelid-derived. Camelid-derived antibodies may be heavy-chain only antibodies i.e. VHH antibodies or may be conventional heterotetrameric antibodies. In preferred embodiments, the antibody molecules of the combinations are derived from camelid heterotetrameric antibodies.

For example, the antibody molecules may be selected from immune libraries obtained by a method comprising the step of immunizing a camelid with the target of interest. The camelid may be immunized with the target protein or polypeptide fragment thereof, or with an mRNA molecule or cDNA molecule expressing the protein or a polypeptide fragment thereof. Methods for producing antibodies in camelid species and selecting antibodies against preferred targets from camelid immune libraries are described in, for example, International patent application no. WO2010/001251, incorporated herein by reference.

In certain embodiments, the antibody molecules may be camelid-derived in that they comprise at least one hypervariable (HV) loop or complementarity determining region obtained from a VH domain or a VL domain of a species in the family Camelidae. In particular, the antibody molecule may comprise VH and/or VL domains, or CDRs thereof, obtained by active immunisation of outbred camelids, e.g. llamas, with for example IL-4Rα and IL-5.

The term "obtained from" in this context implies a structural relationship, in the sense that the HVs or CDRs of the antibody molecule embody an amino acid sequence (or minor variants thereof) which was originally encoded by a Camelidae immunoglobulin gene. However, this does not necessarily imply a particular relationship in terms of the production process used to prepare the antibody molecule.

Camelid-derived antibody molecules may be derived from any camelid species, including inter alia, llama, dromedary, alpaca, vicuna, guanaco or camel.

Antibody molecules comprising camelid-derived VH and VL domains, or CDRs thereof, are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

In certain embodiments, the entire VH domain and/or the entire VL domain may be obtained from a species in the family Camelidae. The camelid-derived VH domain and/or the camelid-derived VL domain may then be subject to protein engineering, in which one or more amino acid substitutions, insertions or deletions are introduced into the camelid amino acid sequence. These engineered changes preferably include amino acid substitutions relative to the camelid sequence. Such changes include "humanisation" or "germlining" wherein one or more amino acid residues in a camelid-encoded VH or VL domain are replaced with equivalent residues from a homologous human-encoded VH or VL domain.

Isolated camelid VH and VL domains obtained by active immunisation of a camelid (e.g. llama) with, for example, IL-4Rα or IL-5, can be used as a basis for engineering antibody molecules for use in the combinations described herein. Starting from intact camelid VH and VL domains, it is possible to engineer one or more amino acid substitutions, insertions or deletions which depart from the starting camelid sequence. In certain embodiments, such substitutions, insertions or deletions may be present in the framework regions of the VH domain and/or the VL domain.

In other embodiments, there are provided "chimeric" antibody molecules comprising camelid-derived VH and VL domains (or engineered variants thereof) and one or more constant domains from a non-camelid antibody, for example human-encoded constant domains (or engineered variants thereof). In such embodiments it is preferred that both the VH domain and the VL domain are obtained from the same species of camelid, for example both VH and VL may be from *Lama glama* or both VH and VL may be from *Lama pacos* (prior to introduction of engineered amino acid sequence variation). In such embodiments both the VH and the VL domain may be derived from a single animal, particularly a single animal which has been actively immunised with the antigen of interest.

As an alternative to engineering changes in the primary amino acid sequence of Camelidae VH and/or VL domains, individual camelid-derived hypervariable loops or CDRs, or combinations thereof, can be isolated from camelid VH/VL domains and transferred to an alternative (i.e. non-Camelidae) framework, e.g. a human VH/VL framework, by CDR grafting.

In non-limiting embodiments, the antibody molecules of the combinations may comprise CH1 domains and/or CL domains (from the heavy chain and light chain, respectively), the amino acid sequence of which is fully or substantially human. For antibody molecules intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. The CH1 domain, hinge region, CH2 domain, CH3 domain and/or CL domain (and/or CH4 domain if present) may be derived from a human antibody, preferably a human IgG antibody, more preferably a human IgG1 antibody of subtype IgG1, IgG2, IgG3 or IgG4.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

Modification of the Fc Region

The antibody molecules of the combinations may have one or more amino acid substitutions, insertions or deletions within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites).

The antibody molecules of the combinations may be modified within the Fc region to increase binding affinity for the neonatal receptor FcRn. The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). By "increased binding affinity" is meant increased binding affinity to FcRn relative to the unmodified Fc region. Typically the unmodified Fc region will possess the wild-type amino acid sequence of human IgG1, IgG2, IgG3 or IgG4. In such embodiments, the increased FcRn binding affinity of the antibody molecule having the modified Fc region will be measured relative to the binding affinity of wild-type IgG1, IgG2, IgG3 or IgG4 for FcRn.

In preferred embodiments, one or more amino acid residues within the Fc region may be substituted with a different amino acid so as to increase binding to FcRn. Several Fc substitutions have been reported that increase FcRn binding and thereby improve antibody pharmacokinetics. Such substitutions are reported in, for example, Zalevsky et al. (2010) *Nat. Biotechnol.* 28(2):157-9; Hinton et al. (2006) *J Immunol.* 176:346-356; Yeung et al. (2009) *J Immunol.* 182:7663-7671; Presta L G. (2008) *Curr. Op. Immunol.* 20:460-470; and Vaccaro et al. (2005) *Nat. Biotechnol.* 23(10):1283-88, the contents of which are incorporated herein in their entirety.

In preferred embodiments, one or more of the antibody molecules of the combinations described herein comprises a modified human IgG Fc domain comprising or consisting of the amino acid substitutions H433K and N434F, wherein the Fc domain numbering is in accordance with EU numbering. In a further preferred embodiment, one or more of the antibody molecules of the combinations described herein comprises a modified human IgG Fc domain comprising or consisting of the amino acid substitutions M252Y, S254T, T256E, H433K and N434F, wherein the Fc domain numbering is in accordance with EU numbering.

In certain embodiments, the antibody molecules, for example the IL-4Rα and/or IL-5 antibody molecules, of the combinations comprise a modified human IgG Fc domain consisting of up to 2, up to 3, up to 4, up to 5, up to 6, up to 7, up to 8, up to 9, up to 10, up to 12, up to 15, up to 20 substitutions relative to the corresponding wild-type IgG sequence.

The antibody molecules may also be modified so as to form immunoconjugates comprising an antibody conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter (2010) *Nature Reviews: Immunology* 10:301-316, incorporated herein by reference.

In particular embodiments, the Fc region may be engineered such that there is no effector function. In certain embodiments, the antibody molecules of the invention may have an Fc region derived from naturally-occurring IgG isotypes having reduced effector function, for example IgG4. Fc regions derived from IgG4 may be further modified to increase therapeutic utility, for example by the introduction of modifications that minimise the exchange of arms between IgG4 molecules in vivo. Fc regions derived from IgG4 may be modified to include the S228P substitution.

In certain embodiments, the antibody molecules of the combinations are modified with respect to glycosylation. For example, an aglycoslated antibody can be made (i.e., the antibody lacks glycosylation). Glycosylation can be altered to, for example, increase the affinity of the antibody for the target antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

pH-Dependent Antibodies

The antibody molecules of the combinations may exhibit pH-dependent antigen binding.

Antibodies that have bound antigen are taken up into cells and trafficked to the endosomal-lysosomal degradation pathway. Antibodies that are able to dissociate from their antigen in the early endosome can be recycled back to the cell surface. Antibodies that bind with high affinity to their antigen in the endosomal compartments are typically trafficked to the lysosomes for degradation. It has been shown previously that if an antibody molecule has pH-dependent antigen binding activity, such that it has a lower binding affinity for its antigen at early endosomal pH as compared with plasma pH, the antibody will recycle to the cell surface more efficiently. This can extend the antibody plasma half-life and allow the same antibody to bind to multiple antigens. For this reason, it is advantageous for the antibody molecules, for example the IL-4Rα and/or IL-5 antibody molecules, of the combinations described herein to exhibit pH-dependent antigen binding.

Methods of engineering pH-dependent antigen binding activity in antibody molecules are described in, for example, EP2275443, which is incorporated herein by reference. Methods of engineering pH-dependent antigen binding in antibody molecules are also described in WO2018/206748, which is incorporated herein by reference. The antibody molecules described herein may be modified in accordance with the methods described in EP2275443 or WO2018/206748 such that they exhibit pH-dependent antigen binding.

For the pH-dependent antibody molecules of the combinations described herein, the antigen-binding activity is lower at endosomal pH as compared to the antigen-binding activity at plasma pH. The endosomal pH is typically acidic pH whereas the plasma pH is typically neutral pH. Accordingly, the antibody molecules of the combinations, for example the IL-4Rα and/or IL-5 antibody molecules described herein, may exhibit pH-dependent antigen binding such that their antigen-binding activity is lower at acidic pH as compared to the antigen-binding activity at neutral pH. Endosomal pH or "acidic pH" may be pH of from about pH 4.0 to about pH 6.5, preferably from about pH 5.5 to about pH 6.5, preferably from about pH 5.5 to about pH 6.0, preferably pH 5.5, pH 5.6, pH 5.7 or pH 5.8. Plasma pH or "neutral pH" may be pH of from about pH 6.9 to about pH 8.0, preferably from about pH 7.0 to about pH 8.0, preferably from about pH 7.0 to about pH 7.4, preferably pH 7.0 or pH 7.4.

In certain embodiments, the antibody molecules, for example the IL-4Rα antibody molecule and/or the IL-5 antibody molecule, exhibit pH-dependent binding such that the antigen-binding activity at pH 5.8 is lower as compared with the antigen-binding activity at pH 7.4. The pH-dependent antibody molecules, for example the IL-4Rα antibody molecule and/or IL-5 antibody molecule, may be characterised in that the dissociation constant (KD) for the antibody-antigen interaction at acidic pH or pH 5.8 is higher than the dissociation constant (KD) for the antibody-antigen interaction at neutral pH or at pH 7.4. In certain embodiments, the antibody molecules, for example the IL-4Rα antibody molecule and/or the IL-5 antibody molecule, exhibit pH-dependent binding such that the ratio of KD for the antigen at pH 5.8 and KD for the antigen at pH 7.4 (KD (pH5.8)/KD (pH7.4)) is 2 or more, 4 or more, 6 or more, 8 or more, 10 or more, 12 or more.

The pH-dependent antigen-binding activity of an antibody molecule may be engineered by modifying an antibody molecule so as to impair the antigen-binding ability at acidic pH and/or increase the antigen-binding ability at neutral pH. For example, the antibody molecule may be modified by substituting at least one amino acid of the antibody molecule with histidine, or by inserting at least one histidine into the antibody molecule. Such histidine mutation (substitution or insertion) sites are not particularly limited, and any site is acceptable as long as the antigen-binding activity at endosomal pH (for example pH 5.8) is lower than that at plasma pH (for example pH 7.4) as compared to before the mutation or insertion.

In certain embodiments, the antibody molecules, for example the IL-4Rα antibody molecule and/or the IL-5 antibody molecule, may be engineered so as to exhibit pH-dependent antigen binding by the introduction of one or more substitutions into the variable domains. In preferred embodiments, the antibody molecules, for example the IL-4Rα antibody molecule and/or the IL-5 antibody molecule, may be engineered so as to exhibit pH-dependent antigen binding by introducing one or more substitutions into the CDRs of the antibody molecule. The substitutions may introduce one or more His residues into one or more sites of the variable domains, preferably the heavy chain and/or light chain CDRs so as to confer pH-dependent antigen binding. Non-histidine substitutions may also be incorporated into variable domains, particularly the CDRs, of the pH-dependent antibodies described herein. The antibody molecules, for example the IL-4Rα antibody molecule and/or the IL-5 antibody molecule, may be engineered in accordance with the methods described in WO2018/206748.

In preferred embodiments, the exemplary IL-4Rα and IL-5 antibodies described herein having the CDR, VH and/or VL domain sequences recited above are engineered such that they exhibit pH-dependent antigen binding. For example, the CDR sequences of the exemplary IL-4Rα and/or IL-5 antibody molecules recited herein may be modified by the introduction of one or more Histidine substitutions so as to produce antibody molecules exhibiting pH-dependent antigen binding.

In particularly preferred embodiments, the pH-dependent antibodies, for example the IL-4Rα and/or IL-5 antibody molecules, of the combinations described herein comprise an Fc domain with increased binding affinity for the neonatal receptor FcRn. Substitutions that may increase the binding affinity of the Fc domain for FcRn are described elsewhere herein and any such substitutions may be incorporated into the pH-dependent antibody molecules of the present combinations.

In particularly preferred embodiments, the combinations comprise a pH-dependent IL-4Rα antibody molecule and a pH-dependent IL-5 antibody molecule wherein one or both of the antibody molecules comprises a modified human IgG Fc domain comprising or consisting of the amino acid substitutions H433K and N434F, wherein the Fc domain numbering is in accordance with EU numbering. In a further preferred embodiment, the combinations comprise a pH-dependent IL-4Rα antibody molecule and a pH-dependent IL-5 antibody molecule wherein one or both of the antibody molecules comprises a modified human IgG Fc domain comprising or consisting of the amino acid substitutions M252Y, S254T, T256E, H433K and N434F, wherein the Fc domain numbering is in accordance with EU numbering.

Exemplary IL-4Rα Antibodies and IL-5 Antibodies

As noted above, in preferred embodiments, the combinations comprise an antibody molecule that binds to IL-5 and an antibody molecule that binds to IL-4Rα. In such embodiments, the combination can inhibit signalling via all three type 2 cytokines: IL-5, IL-4 and IL-13.

Antibody molecules that bind to human IL-4Rα and that may be incorporated into the combinations described herein include antibody molecules comprising a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) selected from the following:

(i) HCDR3 comprising or consisting of SEQ ID NO: 3;
   HCDR2 comprising or consisting of SEQ ID NO: 2;
   HCDR1 comprising or consisting of SEQ ID NO: 1;
   LCDR3 comprising or consisting of SEQ ID NO: 12;
   LCDR2 comprising or consisting of SEQ ID NO: 11;
   LCDR1 comprising or consisting of SEQ ID NO:10;
(ii) HCDR3 comprising or consisting of SEQ ID NO: 6;
   HCDR2 comprising or consisting of SEQ ID NO: 5;
   HCDR1 comprising or consisting of SEQ ID NO: 4;
   LCDR3 comprising or consisting of SEQ ID NO: 15;
   LCDR2 comprising or consisting of SEQ ID NO: 14;
   LCDR1 comprising or consisting of SEQ ID NO: 13;
(iii) HCDR3 comprising or consisting of SEQ ID NO: 9;
   HCDR2 comprising or consisting of SEQ ID NO: 8;
   HCDR1 comprising or consisting of SEQ ID NO: 7;
   LCDR3 comprising or consisting of SEQ ID NO: 18;
   LCDR2 comprising or consisting of SEQ ID NO: 17;
   LCDR1 comprising or consisting of SEQ ID NO:16;
(iv) HCDR3 comprising or consisting of SEQ ID NO: 91;
   HCDR2 comprising or consisting of SEQ ID NO: 8;
   HCDR1 comprising or consisting of SEQ ID NO: 7;
   LCDR3 comprising or consisting of SEQ ID NO: 18;
   LCDR2 comprising or consisting of SEQ ID NO: 17;
   LCDR1 comprising or consisting of SEQ ID NO:16;
(v) HCDR3 comprising or consisting of SEQ ID NO: 92;
   HCDR2 comprising or consisting of SEQ ID NO: 8;
   HCDR1 comprising or consisting of SEQ ID NO: 7;
   LCDR3 comprising or consisting of SEQ ID NO: 97;
   LCDR2 comprising or consisting of SEQ ID NO: 17;
   LCDR1 comprising or consisting of SEQ ID NO:16;
(vi) HCDR3 comprising or consisting of SEQ ID NO: 93;
   HCDR2 comprising or consisting of SEQ ID NO: 8;

HCDR1 comprising or consisting of SEQ ID NO: 7;
LCDR3 comprising or consisting of SEQ ID NO: 98;
LCDR2 comprising or consisting of SEQ ID NO: 96;
LCDR1 comprising or consisting of SEQ ID NO:16;
(vii) HCDR3 comprising or consisting of SEQ ID NO: 94;
HCDR2 comprising or consisting of SEQ ID NO: 8;
HCDR1 comprising or consisting of SEQ ID NO: 7;
LCDR3 comprising or consisting of SEQ ID NO: 98;
LCDR2 comprising or consisting of SEQ ID NO: 17;
LCDR1 comprising or consisting of SEQ ID NO:16; and
(viii) HCDR3 comprising or consisting of SEQ ID NO: 95;
HCDR2 comprising or consisting of SEQ ID NO: 8;
HCDR1 comprising or consisting of SEQ ID NO: 7;
LCDR3 comprising or consisting of SEQ ID NO: 98;
LCDR2 comprising or consisting of SEQ ID NO: 17;
LCDR1 comprising or consisting of SEQ ID NO:16.

Antibody molecules that bind to IL-4Rα and that may be incorporated into the combinations described herein also include antibody molecules comprising a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) selected from the following:
(i) HCDR3 comprising or consisting of SEQ ID NO: 27;
HCDR2 comprising or consisting of SEQ ID NO: 26;
HCDR1 comprising or consisting of SEQ ID NO: 25;
LCDR3 comprising or consisting of SEQ ID NO: 36;
LCDR2 comprising or consisting of SEQ ID NO: 35;
LCDR1 comprising or consisting of SEQ ID NO: 34;
(ii) HCDR3 comprising or consisting of SEQ ID NO: 30;
HCDR2 comprising or consisting of SEQ ID NO: 29;
HCDR1 comprising or consisting of SEQ ID NO: 28;
LCDR3 comprising or consisting of SEQ ID NO: 39;
LCDR2 comprising or consisting of SEQ ID NO: 38;
LCDR1 comprising or consisting of SEQ ID NO: 37; and
(iii) HCDR3 comprising or consisting of SEQ ID NO: 33;
HCDR2 comprising or consisting of SEQ ID NO: 32;
HCDR1 comprising or consisting of SEQ ID NO: 31;
LCDR3 comprising or consisting of SEQ ID NO: 42;
LCDR2 comprising or consisting of SEQ ID NO: 41;
LCDR1 comprising or consisting of SEQ ID NO:40.

In certain embodiments, the antibody molecules that bind to human IL-4Rα are selected from antibody molecules comprising or consisting of a variable heavy chain domain (VH) and a variable light chain domain (VL) selected from the following:
(i) a VH domain comprising or consisting of the amino acid sequence of SEQ ID NO: 19 or an amino acid sequence having at least 70%, at least 80%, at least 90%, at least 95%, at least 98%, at least 99% identity thereto and a VL domain comprising or consisting of the amino acid sequence of SEQ ID NO: 20 or an amino acid sequence having at least 70%, at least 80%, at least 90%, at least 95%, at least 98%, at least 99% identity thereto;
(ii) a VH domain comprising or consisting of the amino acid sequence of SEQ ID NO: 21 or an amino acid sequence having at least 70%, at least 80%, at least 90%, at least 95%, at least 98%, at least 99% identity thereto and a VL domain comprising or consisting of the amino acid sequence of SEQ ID NO: 22 or an amino acid sequence having at least 70%, at least 80%, at least 90%, at least 95%, at least 98%, at least 99% identity thereto;
(iii) a VH domain comprising or consisting of the amino acid sequence of SEQ ID NO: 23 or an amino acid sequence having at least 70%, at least 80%, at least 90%, at least 95%, at least 98%, at least 99% identity thereto and a VL domain comprising or consisting of the amino acid sequence of SEQ ID NO: 24 or an amino acid sequence having at least 70%, at least 80%, at least 90%, at least 95%, at least 98%, at least 99% identity thereto;
(iv) a VH domain comprising or consisting of the amino acid sequence of SEQ ID NO: 99 or an amino acid sequence having at least 70%, at least 80%, at least 90%, at least 95%, at least 98%, at least 99% identity thereto and a VL domain comprising or consisting of the amino acid sequence of SEQ ID NO: 100 or an amino acid sequence having at least 70%, at least 80%, at least 90%, at least 95%, at least 98%, at least 99% identity thereto;
(v) a VH domain comprising or consisting of the amino acid sequence of SEQ ID NO: 101 or an amino acid sequence having at least 70%, at least 80%, at least 90%, at least 95%, at least 98%, at least 99% identity thereto and a VL domain comprising or consisting of the amino acid sequence of SEQ ID NO: 102 or an amino acid sequence having at least 70%, at least 80%, at least 90%, at least 95%, at least 98%, at least 99% identity thereto;
(vi) a VH domain comprising or consisting of the amino acid sequence of SEQ ID NO: 103 or an amino acid sequence having at least 70%, at least 80%, at least 90%, at least 95%, at least 98%, at least 99% identity thereto and a VL domain comprising or consisting of the amino acid sequence of SEQ ID NO: 104 or an amino acid sequence having at least 70%, at least 80%, at least 90%, at least 95%, at least 98%, at least 99% identity thereto;
(vii) a VH domain comprising or consisting of the amino acid sequence of SEQ ID NO: 105 or an amino acid sequence having at least 70%, at least 80%, at least 90%, at least 95%, at least 98%, at least 99% identity thereto and a VL domain comprising or consisting of the amino acid sequence of SEQ ID NO: 106 or an amino acid sequence having at least 70%, at least 80%, at least 90%, at least 95%, at least 98%, at least 99% identity thereto; and
(viii) a VH domain comprising or consisting of the amino acid sequence of SEQ ID NO: 107 or an amino acid sequence having at least 70%, at least 80%, at least 90%, at least 95%, at least 98%, at least 99% identity thereto and a VL domain comprising or consisting of the amino acid sequence of SEQ ID NO: 108 or an amino acid sequence having at least 70%, at least 80%, at least 90%, at least 95%, at least 98%, at least 99% identity thereto.

In certain embodiments, the antibody molecules that bind to IL-4Rα are selected from antibody molecules comprising or consisting of a variable heavy chain domain (VH) and a variable light chain domain (VL) selected from the following:
(i) a VH domain comprising or consisting of the amino acid sequence of SEQ ID NO: 43 or an amino acid sequence having at least 70%, at least 80%, at least 90%, at least 95%, at least 98%, at least 99% thereto and a VL domain comprising or consisting of the amino acid sequence of SEQ ID NO: 44 or an amino acid sequence having at least 70%, at least 80%, at least 90%, at least 95%, at least 98%, at least 99% identity thereto;
(ii)) a VH domain comprising or consisting of the amino acid sequence of SEQ ID NO: 45 or an amino acid sequence having at least 70%, at least 80%, at least 90%, at least 95%, at least 98%, at least 99% thereto and a VL domain comprising or consisting of the amino acid sequence of SEQ ID NO: 46 or an amino acid sequence having at least 70%, at least 80%, at least 90%, at least 95%, at least 98%, at least 99% identity thereto; and (iii)) a VH domain comprising or consisting of the amino acid sequence of SEQ ID NO: 47 or an amino acid sequence having at least 70%, at least 80%, at least 90%, at least 95%, at least 98%, at least 99% thereto and a VL domain comprising or consisting of the amino acid sequence of SEQ ID NO: 48 or an amino acid sequence having at least 70%, at least 80%, at least 90%, at least 95%, at least 98%, at least 99% identity thereto.

Antibody molecules that bind to human IL-5 and that may be incorporated into the combinations described herein include antibody molecules comprising a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) selected from the following:

(i) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 54;
LCDR2 comprising or consisting of SEQ ID NO: 53;
LCDR1 comprising or consisting of SEQ ID NO: 52;

(ii) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 57;
LCDR2 comprising or consisting of SEQ ID NO: 56;
LCDR1 comprising or consisting of SEQ ID NO: 55;

(ii) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 59;
LCDR2 comprising or consisting of SEQ ID NO: 56;
LCDR1 comprising or consisting of SEQ ID NO: 58;

(iv) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 61;
LCDR2 comprising or consisting of SEQ ID NO: 60;
LCDR1 comprising or consisting of SEQ ID NO: 58; and (v) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 62;
LCDR2 comprising or consisting of SEQ ID NO: 56;
LCDR1 comprising or consisting of SEQ ID NO: 58;

Antibody molecules that bind to IL-5 and that may be incorporated into the combinations described herein include antibody molecules comprising a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) selected from the following:

(i) HCDR3 comprising or consisting of SEQ ID NO: 72;
HCDR2 comprising or consisting of SEQ ID NO: 71;
HCDR1 comprising or consisting of SEQ ID NO: 70;
LCDR3 comprising or consisting of SEQ ID NO: 74;
LCDR2 comprising or consisting of SEQ ID NO: 38;
LCDR1 comprising or consisting of SEQ ID NO: 73; and (ii) HCDR3 comprising or consisting of SEQ ID NO: 72;
HCDR2 comprising or consisting of SEQ ID NO: 71;
HCDR1 comprising or consisting of SEQ ID NO: 70;
LCDR3 comprising or consisting of SEQ ID NO: 75;
LCDR2 comprising or consisting of SEQ ID NO: 38;
LCDR1 comprising or consisting of SEQ ID NO: 73.

In certain embodiments, the antibody molecules that bind to human IL-5 are selected from antibody molecules comprising or consisting of a variable heavy chain domain (VH) and a variable light chain domain (VL) selected from the following:

(i) a VH domain comprising or consisting of the amino acid sequence of SEQ ID NO: 63 or an amino acid sequence having at least 70%, at least 80%, at least 90%, at least 95%, at least 98%, at least 99% identity thereto and a VL domain comprising or consisting of the amino acid sequence of SEQ ID NO: 64 or an amino acid sequence having at least 70%, at least 80%, at least 90%, at least 95%, at least 98%, at least 99% identity thereto;

(ii) a VH domain comprising or consisting of the amino acid sequence of SEQ ID NO: 63 or an amino acid sequence having at least 70%, at least 80%, at least 90%, at least 95%, at least 98%, at least 99% identity thereto and a VL domain comprising or consisting of the amino acid sequence of SEQ ID NO: 65 or an amino acid sequence having at least 70%, at least 80%, at least 90%, at least 95%, at least 98%, at least 99% identity thereto;

(iii) a VH domain comprising or consisting of the amino acid sequence of SEQ ID NO: 63 or an amino acid sequence having at least 70%, at least 80%, at least 90%, at least 95%, at least 98%, at least 99% identity thereto and a VL domain comprising or consisting of the amino acid sequence of SEQ ID NO: 66 or an amino acid sequence having at least 70%, at least 80%, at least 90%, at least 95%, at least 98%, at least 99% identity thereto;

(iv) a VH domain comprising or consisting of the amino acid sequence of SEQ ID NO: 63 or an amino acid sequence having at least 70%, at least 80%, at least 90%, at least 95%, at least 98%, at least 99% identity thereto and a VL domain comprising or consisting of the amino acid sequence of SEQ ID NO: 67 or an amino acid sequence having at least 70%, at least 80%, at least 90%, at least 95%, at least 98%, at least 99% identity thereto;

(v) a VH domain comprising or consisting of the amino acid sequence of SEQ ID NO: 63 or an amino acid sequence having at least 70%, at least 80%, at least 90%, at least 95%, at least 98%, at least 99% identity thereto and a VL domain comprising or consisting of the amino acid sequence of SEQ ID NO: 68 or an amino acid sequence having at least 70%, at least 80%, at least 90%, at least 95%, at least 98%, at least 99% identity thereto; and (vi) a VH domain comprising or consisting of the amino acid sequence of SEQ ID NO: 63 or an amino acid sequence having at least 70%, at least 80%, at least 90%, at least 95%, at least 98%, at least 99% identity thereto and a VL domain comprising or consisting of the amino acid sequence of SEQ ID NO: 69 or an amino acid sequence having at least 70%, at least 80%, at least 90%, at least 95%, at least 98%, at least 99% identity thereto;

In certain embodiments, the antibody molecules that bind to IL-5 are selected from antibody molecules comprising or consisting of a variable heavy chain domain (VH) and a variable light chain domain (VL) selected from the following:

(i) a VH domain comprising or consisting of the amino acid sequence of SEQ ID NO: 76 or an amino acid sequence having at least 70%, at least 80%, at least 90%, at least 95%, at least 98%, at least 99% identity thereto and a VL domain comprising or consisting of the amino acid sequence of SEQ ID NO: 77 or an amino acid sequence having at least 70%, at least 80%, at least 90%, at least 95%, at least 98%, at least 99% identity thereto;

(ii) a VH domain comprising or consisting of the amino acid sequence of SEQ ID NO: 76 or an amino acid sequence having at least 70%, at least 80%, at least 90%, at least 95%, at least 98%, at least 99% identity thereto and a VL domain comprising or consisting of the amino acid sequence of SEQ ID NO: 78 or an amino acid sequence having at least 70%, at least 80%, at least 90%, at least 95%, at least 98%, at least 99% identity thereto; and (iii) a VH domain comprising or consisting of the amino acid sequence of SEQ ID NO: 76 or an amino acid sequence having at least 70%, at least 80%, at least 90%, at least 95%, at least 98%, at least 99% identity thereto and a VL domain comprising or consisting of the amino acid sequence of SEQ ID NO: 79 or an amino acid sequence having at least 70%, at least 80%, at least 90%, at least 95%, at least 98%, at least 99% identity thereto.

In preferred embodiments, the combinations comprise an antibody molecule having CDR, VH and/or VL sequences that bind to human IL-4Rα and an antibody molecule having CDR, VH and/or VL sequences that bind to human IL-5.

Where particular antibody molecules are identified as comprising a combination of a VH domain or heavy chain, defined by reference to a specific amino acid sequence, and a VL domain or a light chain, also defined by reference to a specific amino acid sequence, then for each specific VH/VL or heavy chain/light chain combination listed (unless otherwise stated) this definition may be taken to include antibody molecules formed by combination of a VH domain/heavy chain having at least 70%, at least 80%, at least 90%, at least 95%, at least 98% or at least 99% sequence identity to the stated VH/heavy chain amino acid sequence and a VL domain/light chain having at least 70%, at least 80%, at least 90%, at least 95%, at least 98% or at least 99% sequence identity to the stated VL/light chain amino acid sequence.

In each case the domains/chains defined by % sequence identity to the stated domain/chain amino acid sequences may retain identical CDR sequences to those present in the stated VH/VL domain or heavy/light chain amino acid sequences, whilst exhibiting amino acid sequence variation within the framework regions or other regions outside the CDR regions.

In certain embodiments, the IL-4Rα and/or IL-5 antibody molecules defined as having the CDR sequences recited above or defined as having a particular percentage identity to the specific VH/VL domain amino acid sequences recited above are humanised, germlined or affinity variants of the antibodies or antigen binding fragments thereof from which the CDR, VH and/or VL sequences derive.

In a preferred embodiment, the exemplary IL-4Rα and IL-5 antibody molecules having the CDR sequences recited above exhibit high human homology, for example are humanised or germlined variants of the of the antibodies or antigen binding fragments thereof from which the CDR sequences derive.

In non-limiting embodiments, the exemplary IL-4Rα and IL-5 antibody molecules having the CDR, VH and/or VL sequences described herein may comprise CH1 domains and/or CL domains (from the heavy chain and light chain, respectively), the amino acid sequence of which is fully or substantially human. For antibody molecules intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required. Any of the exemplary Fc region modifications described herein may be incorporated into the IL-4Rα and/or IL-5 antibodies having the CDR and/or VH/VL domain sequences recited above. In preferred embodiments, the IL-4Rα and/or IL-5 antibodies having the CDR and/or VH/VL domain sequences recited above comprise a modified human IgG Fc domain comprising or consisting of the amino acid substitutions H433K and N434F, wherein the Fc domain numbering is in accordance with EU numbering. In preferred embodiments, the IL-4Rα and/or IL-5 antibodies having the CDR and/or VH/VL domain sequences recited above comprise a modified human IgG Fc domain comprising or consisting of the amino acid substitutions M252Y, S254T, T256E, H433K and N434F.

In non-limiting embodiments, the exemplary IL-4Rα and IL-5 antibody molecules having the CDR, VH and/or VL sequences described herein may be modified as described above such that they exhibit pH-dependent antigen binding. For example, the exemplary IL-4Rα and IL-5 antibody molecules having the CDR, VH and/or VL sequences described herein may be modified to possess pH-dependent binding such that the antigen-binding activity at pH 5.8 is lower as compared with the antigen-binding activity at pH 7.4. The methods described above for engineering antibodies so as to impart pH-dependent antigen binding may be applied to any of the exemplary IL-4Rα and IL-5 antibody molecules having the CDR, VH and/or VL sequences described herein. For example, the variable domains and/or CDR regions may be modified by Histidine substitutions or insertions so as to confer pH-dependent binding.

Unless otherwise stated in the present application, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, dividing this number of identical positions by the total number of positions in the comparison window and multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

C. Formulation of the Combination

The different antagonists or antibody molecules of the combinations may be combined or formulated in any manner allowing the combination therapy to be administered to a subject or patient in need thereof, preferably a human subject or patient. The combination may be formulated for single dose administration or for multiple dose administration.

In certain embodiments, the antagonists or antibody molecules of the combination are separate molecules that are co-formulated i.e. formulated as a single pharmaceutical composition. For embodiments wherein the antagonists or antibody molecules are co-formulated, the combination or composition is suitable for simultaneous administration of the two components. The composition may be formulated for single dose administration or multiple dose administration. For embodiments in which the antagonists or antibody molecules are co-formulated, the antagonists or antibody molecules may be formulated in equivalent amounts, for example according to a 1:1 ratio for a combination comprising first and second antagonists or antibody molecules targeting different cytokines or receptors. Alternatively, the antagonists or antibody molecules may be formulated such that the ratio of the different antagonists or antibody molecules is not 1:1. For example, for embodiments wherein the combination comprises or consists of first and second antagonists or antibody molecules binding to different targets, the ratio of first and second antagonists or antibody molecules may be 2:1, optionally 3:1, optionally 4:1. Alternatively, the antagonists or antibody molecules may be formulated according to a ratio of 1:2, optionally 1:3, optionally 1:4.

In certain embodiments, the antagonists or antibody molecules of the combination are formulated separately, for example as individual compositions. For embodiments wherein the antagonists or antibody molecules are formulated separately, the possibility exists for simultaneous or separate administration of the different components or compositions. If the antagonists or antibody molecules or the separate compositions containing them are administered separately, there may be sequential administration of the antagonists/antibody molecules or compositions in either order. For example, an antibody molecule that binds to IL-4Rα may be administered first followed by an antibody molecule that binds to IL-5 or vice versa. The interval between administration of the antagonists/antibody molecules or compositions may be any suitable time interval. The administration of the different compositions may be carried out once (for a single dose administration) or repeatedly (for a multiple dose administration).

In certain embodiments wherein the antagonists are antibody molecules, the antibody molecules of the combination may be combined as a multispecific antibody, for example a bispecific antibody. For example, if the combination comprises a Fab fragment that binds IL-4Rα and a Fab fragment that binds to IL-5, the two Fab fragments may be incorporated into a single bispecific antibody molecule having the two Fab regions conjugated to an IgG Fc portion.

Bispecific or multispecific antibodies in accordance with the present invention may be configured according to any suitable bispecific/multispecific antibody format. For example, the antibody molecules of the combination may be incorporated into a bispecific or multispecific antibody format such that the antibody binds to the different targets in "trans", for example the situation where each Fab arm of the Y-shaped antibody has a different binding specificity. In alternative embodiments, the antibody molecules may be incorporated into a bispecific or multispecific antibody format such that the targets are bound in the "cis" position. For example, the Fab regions or variable domains capable of binding antigen may be positioned at opposite ends of an IgG Fc portion.

The bispecific or multispecific antibodies may have a native IgG structure with two Y-shaped Fab arms having binding specificity for the first target, and one or more additional antigen-binding domains positioned at the C terminus of the Fc domain having binding specificity for the second target. For example, in one embodiment, a bispecific antibody in accordance with the present invention is configured such that the two classical antigen-binding domains of the Fab regions present on the native IgG structure bind to IL-4Rα, and one or more VHH domains positioned at the C terminus of the Fc domain binds to IL-5. The reverse configuration is also possible wherein the two classical antigen-binding domains of the Fab regions present on the native IgG structure bind to IL-5, and one or more VHH domains present at the C terminus of the Fc domain bind to IL-4Rα.

Alternatively, the bispecific or multispecific antibodies may have a native IgG structure with two Y-shaped Fab arms having binding specificity for the first target and one or more scFv fragments having binding specificity for the second target positioned at the C-terminus of the Fc domain. For example, in one embodiment, a bispecific antibody in accordance with the present invention is configured such that the two classical antigen-binding domains of the Fab regions present on the native IgG structure bind to IL-4Rα, and one or more scFv domains positioned at the C terminus of the Fc domain bind to IL-5. The reverse configuration is also possible wherein the two classical antigen-binding domains of the Fab regions present on the native IgG structure bind to IL-5, and one or more scFv domains present at the C terminus of the Fc domain bind to IL-4Rα. In such embodiments, the bispecific antibody may consist of two scFv domains present at the C terminus of the IgG Fc domain.

The bispecific or multispecific antibodies may be asymmetric IgG antibodies, such that one Fab region is replaced by a different antigen-binding domain, for example a VHH domain. For example, in another embodiment, a bispecific antibody in accordance with the present invention may be configured similar to a native IgG structure comprising a Fab region on one complete arm of the antibody that binds to IL-4Rα and a VHH domain that binds to IL-5 replacing the second Fab region. The reverse configuration is also possible wherein a Fab region on one complete arm of the antibody binds to IL-5 and a VHH domain that binds to IL-4Rα replaces the second Fab region.

For embodiments wherein the antagonists are antibody molecules and the antibody molecules are co-formulated and/or for embodiments wherein the antibody molecules are provided as separate compositions and/or when the antibody molecules are provided in a multispecific antibody format, the antibody molecules may be formulated using any suitable pharmaceutical carriers or excipients. Techniques for formulating antibodies for human therapeutic use are well known in the art and are reviewed, for example, in Wang et al. (2007) *Journal of Pharmaceutical Sciences*, 96:1-26, the contents of which are incorporated herein in their entirety. For embodiments wherein the antibody molecules are formulated separately, the pharmaceutical carriers or excipients may be different for the different compositions or the same.

Pharmaceutically acceptable excipients that may be used to formulate the compositions include, but are not limited to: ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In certain embodiments, the compositions are formulated for administration to a subject via any suitable route of administration including but not limited to intramuscular, intravenous, intradermal, intraperitoneal injection, subcutaneous, epidural, nasal, oral, rectal, topical, inhalational, buccal (e.g., sublingual), and transdermal administration. For embodiments wherein the antagonists or antibody molecules are formulated separately, each composition may be formulated for administration via a different route.

In certain embodiments, the compositions comprise one or more additional therapeutic agents. Additional therapeutic agents may be agents suitable for preventing or treating a chronic airway disease. The one or more additional agents may be formulated for administration via the same route or via a different route as compared with the antagonists or antibody molecules of the combination.

D. Bispecific IL-4Rα and IL-5 Antibodies

As discussed above, the antibody molecules of the combinations described herein may be provided in a multispecific antibody format, for example, a bispecific antibody format. In preferred embodiments, the combination comprises an antibody molecule that binds to IL-5 and an antibody molecule that binds to IL-4Rα provided in a bispecific antibody format.

Therefore, in accordance with a further aspect of the present invention, provided herein is a bispecific antibody comprising an antigen-binding region that binds to IL-4Rα and an antigen-binding region that binds to IL-5. Such a bispecific antibody is termed herein a "IL-4Rα/IL-5 bispecific" antibody. All the embodiments described above in respect of the separate IL-4Rα and IL-5 antibody molecules apply equally to this further aspect of the invention. In particular, the "antigen-binding regions" of the bispecific antibodies described herein may take the form of any of the antibody or antigen-binding fragments described elsewhere herein, including VHH antibodies.

Bispecific antibodies of the present invention may be configured according to any suitable bispecific/multispecific antibody format, as described elsewhere herein. For example, the bispecific antibody may be configured such that the targets are bound in either the "trans" position i.e. at the same end of the molecule or in the "cis" position i.e. at opposite ends of the molecule.

In certain embodiments, the bispecific antibodies possess a native IgG structure wherein the antigen-binding regions are comprised within the two Fab arms. The first Fab arm may exhibit binding specificity for IL-4Rα and the second Fab arm may exhibit binding specificity for IL-5. In alternative embodiments, the bispecific antibodies possess a native IgG structure and additionally comprise one or more additional antigen-binding regions positioned at the C terminus of the Fc region. In such embodiments, the two Fab arms of the native IgG may bind to the same target, for example IL-4Rα, and the one or more additional antigen-binding regions positioned at the C terminus of the Fc region may bind to the second target, for example IL-5. The one or more additional antigen-binding regions may take any suitable antigen-binding form including but not limited to a VHH domain or a scFv.

In one embodiment, the IL-4Rα/IL-5 bispecific antibody of the invention comprises a Fab region that binds to IL-4Rα and a VHH domain that binds to IL-5. In one embodiment, the IL-4Rα/IL-5 bispecific antibody of the invention comprises a Fab region that binds to IL-5 and a VHH domain that binds to IL-4Rα.

In one embodiment, the IL-4Rα/IL-5 bispecific antibody of the invention comprises a Fab region that binds to IL-4Rα and a scFv that binds to IL-5. In one embodiment, the IL-4Rα/IL-5 bispecific antibody of the invention comprises a Fab region that binds to IL-5 and a scFv that binds to IL-4Rα. In preferred embodiments, the IL-4Rα/IL-5 bispecific antibody of the invention comprises or consists of an IgG antibody that binds to IL-4Rα and one or more scFv that binds to IL-5. In such embodiments, the IL-4Rα/IL-5 bispecific antibody may comprises or consists of an IgG antibody that binds to IL-4Rα and two scFv fragments that binds to IL-5. The one or more scFv fragments binding to IL-5 are preferably positioned at the C-terminus of the Fc region of the IgG antibody i.e. at the opposite end of the Fc region from the two Fab arms that bind to IL-4Rα.

The bispecific antibody of the invention may be configured as an asymmetric IgG antibody wherein one Fab region (or Fab arm) is replaced by a different antigen-binding region or domain, for example a VHH domain. In one embodiment, the IL-4Rα/IL-5 bispecific antibody is configured similar to a native IgG structure comprising a Fab region on one complete arm of the antibody that binds to IL-4Rα and a VHH domain replacing the second Fab region that binds to IL-5. The reverse configuration is also possible wherein a Fab region on one complete arm of the antibody binds to IL-5, and a VHH domain replacing the second Fab region binds to IL-4Rα.

The IL-4Rα/IL-5 bispecific antibodies of the present invention i.e. configured according to any of the formats described herein, may comprise an antigen-binding region that binds to human IL-4R, wherein the antigen binding region comprises a variable heavy chain domain (VH) and a variable light chain domain (VL) wherein the VH and VL domains comprise the CDR sequences selected from the group consisting of:

(i) HCDR3 comprising or consisting of SEQ ID NO: 3;
   HCDR2 comprising or consisting of SEQ ID NO: 2;
   HCDR1 comprising or consisting of SEQ ID NO: 1;
   LCDR3 comprising or consisting of SEQ ID NO: 12;
   LCDR2 comprising or consisting of SEQ ID NO: 11;
   LCDR1 comprising or consisting of SEQ ID NO: 10;
(ii) HCDR3 comprising or consisting of SEQ ID NO: 6;
   HCDR2 comprising or consisting of SEQ ID NO: 5;
   HCDR1 comprising or consisting of SEQ ID NO: 4;
   LCDR3 comprising or consisting of SEQ ID NO: 15;
   LCDR2 comprising or consisting of SEQ ID NO: 14;
   LCDR1 comprising or consisting of SEQ ID NO: 13;
(iii) HCDR3 comprising or consisting of SEQ ID NO: 9;
   HCDR2 comprising or consisting of SEQ ID NO: 8;
   HCDR1 comprising or consisting of SEQ ID NO: 7;
   LCDR3 comprising or consisting of SEQ ID NO: 18;
   LCDR2 comprising or consisting of SEQ ID NO: 17;
   LCDR1 comprising or consisting of SEQ ID NO: 16;

(iv) HCDR3 comprising or consisting of SEQ ID NO: 91;
HCDR2 comprising or consisting of SEQ ID NO: 8;
HCDR1 comprising or consisting of SEQ ID NO: 7;
LCDR3 comprising or consisting of SEQ ID NO: 18;
LCDR2 comprising or consisting of SEQ ID NO: 17;
LCDR1 comprising or consisting of SEQ ID NO:16;
(v) HCDR3 comprising or consisting of SEQ ID NO: 92;
HCDR2 comprising or consisting of SEQ ID NO: 8;
HCDR1 comprising or consisting of SEQ ID NO: 7;
LCDR3 comprising or consisting of SEQ ID NO: 97;
LCDR2 comprising or consisting of SEQ ID NO: 17;
LCDR1 comprising or consisting of SEQ ID NO:16;
(vi) HCDR3 comprising or consisting of SEQ ID NO: 93;
HCDR2 comprising or consisting of SEQ ID NO: 8;
HCDR1 comprising or consisting of SEQ ID NO: 7;
LCDR3 comprising or consisting of SEQ ID NO: 98;
LCDR2 comprising or consisting of SEQ ID NO: 96;
LCDR1 comprising or consisting of SEQ ID NO:16;
(vii) HCDR3 comprising or consisting of SEQ ID NO: 94;
HCDR2 comprising or consisting of SEQ ID NO: 8;
HCDR1 comprising or consisting of SEQ ID NO: 7;
LCDR3 comprising or consisting of SEQ ID NO: 98;
LCDR2 comprising or consisting of SEQ ID NO: 17;
LCDR1 comprising or consisting of SEQ ID NO:16; and
(viii) HCDR3 comprising or consisting of SEQ ID NO: 95;
HCDR2 comprising or consisting of SEQ ID NO: 8;
HCDR1 comprising or consisting of SEQ ID NO: 7;
LCDR3 comprising or consisting of SEQ ID NO: 98;
LCDR2 comprising or consisting of SEQ ID NO: 17;
LCDR1 comprising or consisting of SEQ ID NO:16.

The IL-4Rα/IL-5 bispecific antibodies of the present invention may comprise an antigen-binding region that binds to IL-4R, wherein the antigen binding region comprises a variable heavy chain domain (VH) and a variable light chain domain (VL) wherein the VH and VL domains comprise the CDR sequences selected from the group consisting of:
(i) HCDR3 comprising or consisting of SEQ ID NO: 27;
HCDR2 comprising or consisting of SEQ ID NO: 26;
HCDR1 comprising or consisting of SEQ ID NO: 25;
LCDR3 comprising or consisting of SEQ ID NO: 36;
LCDR2 comprising or consisting of SEQ ID NO: 35;
LCDR1 comprising or consisting of SEQ ID NO: 34;
(ii) HCDR3 comprising or consisting of SEQ ID NO: 30;
HCDR2 comprising or consisting of SEQ ID NO: 29;
HCDR1 comprising or consisting of SEQ ID NO: 28;
LCDR3 comprising or consisting of SEQ ID NO: 39;
LCDR2 comprising or consisting of SEQ ID NO: 38;
LCDR1 comprising or consisting of SEQ ID NO: 37; and
(iii) HCDR3 comprising or consisting of SEQ ID NO: 33;
HCDR2 comprising or consisting of SEQ ID NO: 32;
HCDR1 comprising or consisting of SEQ ID NO: 31;
LCDR3 comprising or consisting of SEQ ID NO: 42;
LCDR2 comprising or consisting of SEQ ID NO: 41;
LCDR1 comprising or consisting of SEQ ID NO:40.

The antigen-binding region that binds to human IL-4Rα may comprise a variable heavy chain domain (VH) and a variable light chain domain (VL) selected from the group consisting of:
(i) a VH domain comprising the amino acid sequence of SEQ ID NO: 19 or an amino acid sequence having at least 70%, at least 80%, at least 90%, at least 95%, at least 98%, at least 99% identity thereto and a VL domain comprising the amino acid sequence of SEQ ID NO: 20 or an amino acid sequence having at least 70%, at least 80%, at least 90%, at least 95%, at least 98%, at least 99% identity thereto;
(ii) a VH domain comprising the amino acid sequence of SEQ ID NO: 21 or an amino acid sequence having at least 70%, at least 80%, at least 90%, at least 95%, at least 98%, at least 99% identity thereto and a VL domain comprising the amino acid sequence of SEQ ID NO: 22 or an amino acid sequence having at least 70%, at least 80%, at least 90%, at least 95%, at least 98%, at least 99% identity thereto;
(iii) a VH domain comprising the amino acid sequence of SEQ ID NO: 23 or an amino acid sequence having at least 70%, at least 80%, at least 90%, at least 95%, at least 98%, at least 99% identity thereto and a VL domain comprising the amino acid sequence of SEQ ID NO: 24 or an amino acid sequence having at least 70%, at least 80%, at least 90%, at least 95%, at least 98%, at least 99% identity thereto;
(iv) a VH domain comprising or consisting of the amino acid sequence of SEQ ID NO: 99 or an amino acid sequence having at least 70%, at least 80%, at least 90%, at least 95%, at least 98%, at least 99% identity thereto and a VL domain comprising or consisting of the amino acid sequence of SEQ ID NO: 100 or an amino acid sequence having at least 70%, at least 80%, at least 90%, at least 95%, at least 98%, at least 99% identity thereto;
(v) a VH domain comprising or consisting of the amino acid sequence of SEQ ID NO: 101 or an amino acid sequence having at least 70%, at least 80%, at least 90%, at least 95%, at least 98%, at least 99% identity thereto and a VL domain comprising or consisting of the amino acid sequence of SEQ ID NO: 102 or an amino acid sequence having at least 70%, at least 80%, at least 90%, at least 95%, at least 98%, at least 99% identity thereto;
(vi) a VH domain comprising or consisting of the amino acid sequence of SEQ ID NO: 103 or an amino acid sequence having at least 70%, at least 80%, at least 90%, at least 95%, at least 98%, at least 99% identity thereto and a VL domain comprising or consisting of the amino acid sequence of SEQ ID NO: 104 or an amino acid sequence having at least 70%, at least 80%, at least 90%, at least 95%, at least 98%, at least 99% identity thereto;
(vii) a VH domain comprising or consisting of the amino acid sequence of SEQ ID NO: 105 or an amino acid sequence having at least 70%, at least 80%, at least 90%, at least 95%, at least 98%, at least 99% identity thereto and a VL domain comprising or consisting of the amino acid sequence of SEQ ID NO: 106 or an amino acid sequence having at least 70%, at least 80%, at least 90%, at least 95%, at least 98%, at least 99% identity thereto; and
(viii) a VH domain comprising or consisting of the amino acid sequence of SEQ ID NO: 107 or an amino acid sequence having at least 70%, at least 80%, at least 90%, at least 95%, at least 98%, at least 99% identity thereto and a VL domain comprising or consisting of the amino acid sequence of SEQ ID NO: 108 or an amino acid sequence having at least 70%, at least 80%, at least 90%, at least 95%, at least 98%, at least 99% identity thereto.

The antigen-binding region that binds to IL-4Rα may comprise a variable heavy chain domain (VH) and a variable light chain domain (VL) selected from the group consisting of:
(i) a VH domain comprising the amino acid sequence of SEQ ID NO: 43 or an amino acid sequence having at least 70% identity thereto and a VL domain comprising the amino acid sequence of SEQ ID NO: 44 or an amino acid sequence having at least 70% identity thereto;

(ii) a VH domain comprising the amino acid sequence of SEQ ID NO: 45 or an amino acid sequence having at least 70% identity thereto and a VL domain comprising the amino acid sequence of SEQ ID NO: 46 or an amino acid sequence having at least 70% identity thereto; and (iii) a VH domain comprising the amino acid sequence of SEQ ID NO: 47 or an amino acid sequence having at least 70% identity thereto and a VL domain comprising the amino acid sequence of SEQ ID NO: 48 or an amino acid sequence having at least 70% identity thereto.

The IL-4Rα/IL-5 bispecific antibodies of the present invention may comprise an antigen-binding region that binds to human IL-5, wherein the antigen binding region comprises a variable heavy chain domain (VH) and a variable light chain domain (VL) wherein the VH and VL domains comprise the CDR sequences selected from the group consisting of:

(i) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 54;
LCDR2 comprising or consisting of SEQ ID NO: 53;
LCDR1 comprising or consisting of SEQ ID NO: 52;

(ii) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 57;
LCDR2 comprising or consisting of SEQ ID NO: 56;
LCDR1 comprising or consisting of SEQ ID NO: 55;

(ii) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 59;
LCDR2 comprising or consisting of SEQ ID NO: 56;
LCDR1 comprising or consisting of SEQ ID NO: 58;

(iv) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 61;
LCDR2 comprising or consisting of SEQ ID NO: 60;
LCDR1 comprising or consisting of SEQ ID NO: 58; and (v) HCDR3 comprising or consisting of SEQ ID NO: 51;
HCDR2 comprising or consisting of SEQ ID NO: 50;
HCDR1 comprising or consisting of SEQ ID NO: 49;
LCDR3 comprising or consisting of SEQ ID NO: 62;
LCDR2 comprising or consisting of SEQ ID NO: 56;
LCDR1 comprising or consisting of SEQ ID NO: 58.

The IL-4Rα/IL-5 bispecific antibodies of the present invention may comprise an antigen-binding region that binds to IL-5, wherein the antigen binding region comprises a variable heavy chain domain (VH) and a variable light chain domain (VL) wherein the VH and VL domains comprise the CDR sequences selected from the group consisting of:

(i) HCDR3 comprising or consisting of SEQ ID NO: 72;
HCDR2 comprising or consisting of SEQ ID NO: 71;
HCDR1 comprising or consisting of SEQ ID NO: 70;
LCDR3 comprising or consisting of SEQ ID NO: 74;
LCDR2 comprising or consisting of SEQ ID NO: 38;
LCDR1 comprising or consisting of SEQ ID NO: 73; and (ii) HCDR3 comprising or consisting of SEQ ID NO: 72;
HCDR2 comprising or consisting of SEQ ID NO: 71;
HCDR1 comprising or consisting of SEQ ID NO: 70;
LCDR3 comprising or consisting of SEQ ID NO: 75;
LCDR2 comprising or consisting of SEQ ID NO: 38;
LCDR1 comprising or consisting of SEQ ID NO: 73.

The antigen-binding region that binds to human IL-5 may comprise a variable heavy chain domain (VH) and a variable light chain domain (VL) selected from the group consisting of:

(i) a VH domain comprising the amino acid sequence of SEQ ID NO: 63 or an amino acid sequence having at least 70% identity thereto and a VL domain comprising the amino acid sequence of SEQ ID NO: 64 or an amino acid sequence having at least 70% identity thereto;

(ii) a VH domain comprising the amino acid sequence of SEQ ID NO: 63 or an amino acid sequence having at least 70% identity thereto and a VL domain comprising the amino acid sequence of SEQ ID NO: 65 or an amino acid sequence having at least 70% identity thereto;

(iii) a VH domain comprising the amino acid sequence of SEQ ID NO: 63 or an amino acid sequence having at least 70% identity thereto and a VL domain comprising the amino acid sequence of SEQ ID NO: 66 or an amino acid sequence having at least 70% identity thereto;

(iv) a VH domain comprising the amino acid sequence of SEQ ID NO: 63 or an amino acid sequence having at least 70% identity thereto and a VL domain comprising the amino acid sequence of SEQ ID NO: 67 or an amino acid sequence having at least 70% identity thereto;

(v) a VH domain comprising the amino acid sequence of SEQ ID NO: 63 or an amino acid sequence having at least 70% identity thereto and a VL domain comprising the amino acid sequence of SEQ ID NO: 68 or an amino acid sequence having at least 70% identity thereto; and (vi) a VH domain comprising the amino acid sequence of SEQ ID NO: 63 or an amino acid sequence having at least 70% identity thereto and a VL domain comprising the amino acid sequence of SEQ ID NO: 69 or an amino acid sequence having at least 70% identity thereto.

The antigen-binding region that binds to IL-5 may comprise a variable heavy chain domain (VH) and a variable light chain domain (VL) selected from the group consisting of:

(i) a VH domain comprising the amino acid sequence of SEQ ID NO: 76 or an amino acid sequence having at least 70% identity thereto and a VL domain comprising the amino acid sequence of SEQ ID NO: 77 or an amino acid sequence having at least 70% identity thereto;

(ii) a VH domain comprising the amino acid sequence of SEQ ID NO: 76 or an amino acid sequence having at least 70% identity thereto and a VL domain comprising the amino acid sequence of SEQ ID NO: 78 or an amino acid sequence having at least 70% identity thereto; and (iii) a VH domain comprising the amino acid sequence of SEQ ID NO: 76 or an amino acid sequence having at least 70% identity thereto and a VL domain comprising the amino acid sequence of SEQ ID NO: 79 or an amino acid sequence having at least 70% identity thereto.

In each case the domains/chains defined by % sequence identity to the stated domain/chain amino acid sequences may retain identical CDR sequences to those present in the stated VH/VL domain or heavy/light chain amino acid sequences, whilst exhibiting amino acid sequence variation within the framework regions or other regions outside the CDR regions.

In preferred embodiments, the IL-4Rα/IL-5 bispecific antibodies of the present invention may comprise an antigen binding region that binds to IL-4Rα and an antigen binding region that binds to IL-5, wherein the antigen binding region that binds to IL-4Rα comprises a first variable heavy chain domain (VH) and variable light chain domain (VL) pairing and the antigen binding region that binds to IL-5 comprises a second variable heavy chain domain (VH) and variable light chain domain (VL) pairing, wherein the first VH-VL domain pairing comprises the CDR sequences selected from:
(i) HCDR3 comprising or consisting of SEQ ID NO: 3;
   HCDR2 comprising or consisting of SEQ ID NO: 2;
   HCDR1 comprising or consisting of SEQ ID NO: 1;
   LCDR3 comprising or consisting of SEQ ID NO: 12;
   LCDR2 comprising or consisting of SEQ ID NO: 11;
   LCDR1 comprising or consisting of SEQ ID NO: 10;
(ii) HCDR3 comprising or consisting of SEQ ID NO: 6;
   HCDR2 comprising or consisting of SEQ ID NO: 5;
   HCDR1 comprising or consisting of SEQ ID NO: 4;
   LCDR3 comprising or consisting of SEQ ID NO: 15;
   LCDR2 comprising or consisting of SEQ ID NO: 14;
   LCDR1 comprising or consisting of SEQ ID NO: 13; and
(iii) HCDR3 comprising or consisting of SEQ ID NO: 9;
   HCDR2 comprising or consisting of SEQ ID NO: 8;
   HCDR1 comprising or consisting of SEQ ID NO: 7;
   LCDR3 comprising or consisting of SEQ ID NO: 18;
   LCDR2 comprising or consisting of SEQ ID NO: 17;
   LCDR1 comprising or consisting of SEQ ID NO: 16; and
wherein the second VH-VL domain pairing comprises the CDR sequences selected from:
(i) HCDR3 comprising or consisting of SEQ ID NO: 51;
   HCDR2 comprising or consisting of SEQ ID NO: 50;
   HCDR1 comprising or consisting of SEQ ID NO: 49;
   LCDR3 comprising or consisting of SEQ ID NO: 54;
   LCDR2 comprising or consisting of SEQ ID NO: 53;
   LCDR1 comprising or consisting of SEQ ID NO: 52;
(ii) HCDR3 comprising or consisting of SEQ ID NO: 51;
   HCDR2 comprising or consisting of SEQ ID NO: 50;
   HCDR1 comprising or consisting of SEQ ID NO: 49;
   LCDR3 comprising or consisting of SEQ ID NO: 57;
   LCDR2 comprising or consisting of SEQ ID NO: 56;
   LCDR1 comprising or consisting of SEQ ID NO: 55;
(ii) HCDR3 comprising or consisting of SEQ ID NO: 51;
   HCDR2 comprising or consisting of SEQ ID NO: 50;
   HCDR1 comprising or consisting of SEQ ID NO: 49;
   LCDR3 comprising or consisting of SEQ ID NO: 59;
   LCDR2 comprising or consisting of SEQ ID NO: 56;
   LCDR1 comprising or consisting of SEQ ID NO: 58;
(iv) HCDR3 comprising or consisting of SEQ ID NO: 51;
   HCDR2 comprising or consisting of SEQ ID NO: 50;
   HCDR1 comprising or consisting of SEQ ID NO: 49;
   LCDR3 comprising or consisting of SEQ ID NO: 61;
   LCDR2 comprising or consisting of SEQ ID NO: 60;
   LCDR1 comprising or consisting of SEQ ID NO: 58; and
(v) HCDR3 comprising or consisting of SEQ ID NO: 51;
   HCDR2 comprising or consisting of SEQ ID NO: 50;
   HCDR1 comprising or consisting of SEQ ID NO: 49;
   LCDR3 comprising or consisting of SEQ ID NO: 62;
   LCDR2 comprising or consisting of SEQ ID NO: 56;
   LCDR1 comprising or consisting of SEQ ID NO: 58.

In preferred embodiments, the IL-4Rα/IL-5 bispecific antibodies of the present invention may comprise an antigen binding region that binds to IL-4Rα and an antigen binding region that binds to IL-5, wherein the antigen binding region that binds to IL-4Rα comprises a first variable heavy chain domain (VH) and variable light chain domain (VL) pairing and the antigen binding region that binds to IL-5 comprises a second variable heavy chain domain (VH) and variable light chain domain (VL) pairing, wherein the first VH-VL domain pairing is selected from:
(i) a VH domain comprising the amino acid sequence of SEQ ID NO: 19 or an amino acid sequence having at least 70% identity thereto and a VL domain comprising the amino acid sequence of SEQ ID NO: 20 or an amino acid sequence having at least 70% identity thereto;
(ii) a VH domain comprising the amino acid sequence of SEQ ID NO: 21 or an amino acid sequence having at least 70% identity thereto and a VL domain comprising the amino acid sequence of SEQ ID NO: 22 or an amino acid sequence having at least 70% identity thereto; and
(iii) a VH domain comprising the amino acid sequence of SEQ ID NO: 23 or an amino acid sequence having at least 70% identity thereto and a VL domain comprising the amino acid sequence of SEQ ID NO: 24 or an amino acid sequence having at least 70% identity thereto, and wherein the second VH-VL domain pairing is selected from:
(i) a VH domain comprising the amino acid sequence of SEQ ID NO: 63 or an amino acid sequence having at least 70% identity thereto and a VL domain comprising the amino acid sequence of SEQ ID NO: 64 or an amino acid sequence having at least 70% identity thereto;
(ii) a VH domain comprising the amino acid sequence of SEQ ID NO: 63 or an amino acid sequence having at least 70% identity thereto and a VL domain comprising the amino acid sequence of SEQ ID NO: 65 or an amino acid sequence having at least 70% identity thereto;
(iii) a VH domain comprising the amino acid sequence of SEQ ID NO: 63 or an amino acid sequence having at least 70% identity thereto and a VL domain comprising the amino acid sequence of SEQ ID NO: 66 or an amino acid sequence having at least 70% identity thereto;
(iv) a VH domain comprising the amino acid sequence of SEQ ID NO: 63 or an amino acid sequence having at least 70% identity thereto and a VL domain comprising the amino acid sequence of SEQ ID NO: 67 or an amino acid sequence having at least 70% identity thereto;
(v) a VH domain comprising the amino acid sequence of SEQ ID NO: 63 or an amino acid sequence having at least 70% identity thereto and a VL domain comprising the amino acid sequence of SEQ ID NO: 68 or an amino acid sequence having at least 70% identity thereto; and
(vi) a VH domain comprising the amino acid sequence of SEQ ID NO: 63 or an amino acid sequence having at least 70% identity thereto and a VL domain comprising the amino acid sequence of SEQ ID NO: 69 or an amino acid sequence having at least 70% identity thereto.

In preferred embodiments, the antigen-binding regions of the bispecific antibodies described herein exhibit high human homology. For example, the antigen-binding regions may be humanised or germlined variants of the VH and/or VL domains from which the CDR sequences derive.

The bispecific antibodies of the present invention may also comprise one or more constant domains having amino acid sequences that are fully or substantially human. For example, the bispecific antibodies of the present invention may comprise an Fc domain derived from a human IgG antibody, for example a human IgG1, IgG2, IgG3 or IgG4.

Bispecific antibodies of the present invention having an Fc domain may be modified within the Fc region to enhance binding affinity for the neonatal receptor FcRn, as described elsewhere herein. For example, one or more amino acid residues within the Fc region may be substituted with different amino acid residues so as to increase binding to FcRn. Preferred amino acid substitutions in the Fc region are described elsewhere herein, and apply equally to bispecific antibodies of the present invention.

Bispecific antibodies of the present invention may be modified to possess pH-dependent antigen binding activity, as described elsewhere herein. In particular, the bispecific antibodies may be modified such that the IL-4Rα and/or IL-5 binding activity is lower at acidic pH as compared to the binding activity at neutral pH. The bispecific antibody may be modified by substituting at least one amino acid of the IL-4Rα antigen-binding region and/or the IL-5 antigen binding region of the antibody molecule with histidine, or by inserting at least one histidine into one or both of the antigen binding regions of the antibody molecule. Histidine substitutions and/or insertions are preferably introduced at one or more sites within the CDRs of the heavy chain variable domain and/or the light chain variable domain, as described herein.

E. Methods of Treatment

The combination therapies and bispecific antibodies as described herein are for use in methods of treating chronic airway disease in a human subject.

The present invention thus provides a combination comprising (i) an antagonist of IL-5:IL-5R; and (ii) an antagonist of IL-4:IL-4R and/or an antagonist of IL-13:IL-13R for use in the treatment of chronic airway disease in a human subject. The present invention also provides a bispecific antibody comprising an antigen-binding region that binds to IL-4Rα and an antigen-binding region that binds to IL-5 for use in the treatment of chronic airway disease in a human subject. The present invention provides an antagonist of IL-5:IL-5R IL-5 for use in the treatment of chronic airway disease in a human subject, wherein the antagonist is administered in combination with an antagonist of IL-4:IL-4R and/or an antagonist of IL-13:IL-13R. The present invention provides an antagonist of IL-4:IL-4R and/or an antagonist of IL-13:IL-13R for use in the treatment of chronic airway disease in a human subject, wherein the antagonist is administered in combination with an antagonist of IL-5:IL-5R. In preferred embodiments, the invention provides an antagonist of IL-5 for use in the treatment of chronic airway disease in a human subject, wherein the antagonist is administered in combination with an antagonist of IL-4Rα. In further preferred embodiments, the invention provides an antagonist of IL-4Rα for use in the treatment of chronic airway disease in a human subject, wherein the antagonist is administered in combination with an antagonist of IL-5. In further preferred embodiments, the antagonists for use in the methods are antibody molecules.

In a yet further aspect, the present invention provides a method for treating chronic airway disease in a human subject, said method comprising administering to the subject an effective amount of a combination in accordance with the first aspect of the invention, or a bispecific antibody in accordance with the second aspect of the invention. All embodiments described above in relation to the combinations of the first aspect of the invention and the bispecific antibodies of the second aspect of the invention are equally applicable to the methods described herein.

In certain embodiments, the methods described herein are for treating chronic airway diseases. As described elsewhere herein, chronic airway disease encompasses any disease of the airways and other structures of the lung. Non-limiting examples include asthma; chronic rhinosinusitis (CRS); immunoglobulin G4-related disease (IgG4-RD); chronic obstructive pulmonary disease (COPD); chronic bronchitis; emphysema; chronic angioedema; diseases characterised by goblet cell metaplasia including Barrett's oesophagus, active eosinophilic esophagitis, nasal polyposis, chronic sinusitis, Churg Strauss Syndrome, allergic bronchopulmonary aspergillosis (ABPA), hypereosinophilic syndrome; bullous pemphigoid and cystic fibrosis.

In certain embodiments, the methods described herein are for treating chronic airway diseases characterized by increased mucus production. One example of a disease characterised by increased mucus production is cystic fibrosis. In further embodiments, the methods described herein are for treating chronic airway disease characterized by bronchial hyperresponsiveness.

In preferred embodiments, the methods described herein are for treating asthma. Exemplary asthma subtypes include but are not limited to: severe asthma, severe refractory asthma, mild or moderate asthma, obesity-related asthma, exercise-induced asthma, aspirin-induced asthma, atopic or allergic asthma, eosinophilic asthma, neutrophilic asthma, paucigranulocytic or non-inflammatory asthma, early onset asthma, late-onset asthma, type II high asthma, type II low asthma, and type I/Th17 asthma.

In preferred embodiments, the methods described herein are for treating atopic or allergic asthma. Atopic or allergic asthma is the form of asthma defined clinically as the disease coinciding with allergic sensitization defined by the presence of serum IgE antibodies and/or a positive skin-prick test to the (lipo)proteins of common inhaled or ingested allergens such as house dust mite (HDM), animal dander, fungal spores, plant or tree pollen, or peanuts (Lambrecht and Hammad (2015) ibid). The vast majority of early-onset asthma cases are of the allergic or atopic type. As such, the methods of the present invention may also be for the treatment of early-onset asthma.

In further preferred embodiments, the methods described herein are for treating Type II high (or Type II Hi) asthma. Type II high asthma is characterised by the presence of a Type 2 cytokine molecular signature. Subjects having Type II high asthma typically express higher levels of IL-13 and IL-5, have greater numbers of eosinophils and mast cells and show more atopy and SBM (sub-epithelial basement membrane) thickening as compared to Type II low asthmatics (see Wenzel (2012) ibid and Gauthier et al. (2015) ibid). The combinations and bispecific antibodies of the present invention target multiple type 2 cytokine signalling pathways. It follows that the combinations and bispecific antibodies described here may be particularly effective for the treatment of human subjects having Type II high asthma.

In certain embodiments, the methods described herein are for treating severe asthma, or severe refractory asthma.

Almost all forms of asthma are associated with pathological goblet cell metaplasia or GCM. GCM is caused by the transdifferentiation of ciliated and Clara cells to goblet cells under the influence of IL-4 and/or IL-13 and ligands of the epidermal growth factor receptor. Accordingly, in certain embodiments, the methods described herein are for treating asthma by decreasing goblet cell metaplasia. In such embodiments, goblet cell metaplasia is decreased, as compared to the level of goblet cell metaplasia prior to the treatment.

Patients having chronic airway disease, including the majority of asthmatics, also suffer from bronchial hyperresponsiveness (BHR). BHR is defined as an increase in sensitivity to a wide variety of airway narrowing stimuli. Most patients with asthma and chronic obstructive pulmonary disease (COPD) exhibit such an enhanced sensitivity. In certain embodiments, the methods described herein are for treating chronic airway disease by decreasing bronchial hyperresponsiveness. In preferred embodiments, the methods described herein are for treating asthma by decreasing bronchial hyperresponsiveness. In such embodiments, bronchial hyperresponsiveness is decreased relative to the level of bronchial hyperresponsiveness prior to treatment. Bronchial hyperresponsiveness can be assessed with a bronchial challenge test. This most often uses products like methacholine or histamine. These chemicals trigger bronchospasm in normal individuals as well, but people with bronchial hyperresponsiveness have a lower threshold.

Patients having chronic airway disease, including the majority of asthmatics, also exhibit excessive mucus production. In certain embodiments, the methods described herein are for treating chronic airway disease by decreasing mucus production. In preferred embodiments, the methods described herein are for treating asthma by decreasing mucus production. In such embodiments, mucus production is decreased relative to the level of mucus production prior to treatment. Mucus production can be assessed by measuring the expression and/or activity of mucins, for example the expression and/or activity of muc5AC. In certain embodiments, the methods described herein are for treating chronic airway disease by decreasing the expression and/or activity of mucins relative to the expression and/or activity prior to treatment. In certain embodiments, the methods described herein are for treating asthma by decreasing the expression and/or activity of mucins relative to the expression and/or activity prior to treatment.

Chronic airway disease is also characterised by poor lung function. Forced expiratory volume (FEV) is a measure of lung function, and can be assessed using a spirometer. Forced expiratory volume (FEV) measures how much air a person can exhale during a forced breath. Forced vital capacity (FVC) is the total amount of air exhaled during the FEV test. The FEV1/FVC ratio, also called Tiffeneau-Pinelli index, is a calculated ratio that represents the proportion of a person's vital capacity that they are able to expire in the first second of forced expiration to the full vital capacity. A normal value for the FEV1/FVC ratio is approximately 70-80%. In certain embodiments, the methods described herein are for treating chronic airway disease by improving lung function. In preferred embodiments, the methods described herein are for treating asthma by improving lung function. In such embodiments, lung function is improved relative to the lung function prior to treatment. In certain embodiments, the methods described herein are for treating chronic airway disease by increasing the FEV1/FVC ratio relative to the FEV1/FVC ratio prior to treatment. In certain embodiments, the methods described herein are for treating asthma by increasing the FEV1/FVC ratio relative to the FEV1/FVC ratio prior to treatment.

The methods described herein may also be used to treat co-morbidities associated with chronic airway disease, for example co-morbidities associated with asthma. Severe asthma is associated with a number of co-morbidities including but not limited to: chronic rhinosinusitis; nasal polyposis; allergic rhinitis; dysfunctional breathing; vocal cord dysfunction; anxiety and depression; obesity; obstructive sleep apnoea syndrome (OSAS); gastroesophageal reflux disease (GERD); bronchiectasis; allergic bronchopulmonary aspergillosis (ABPA); and eosinophilic granulomatous with polyangiitis (EGPA) (see Porsbjerg and Menzies-Gow (2017) *Respirology* 22: 651-661). The methods described herein may be used to treat any of the above-listed asthma co-morbidities. The methods described herein may include administration of further therapeutic agents. In certain embodiments, the methods described herein comprise administering one or more additional therapeutic agents to treat chronic airway disease. The combination or bispecific antibody in accordance with the present invention may be administered separately, simultaneously, sequentially, or concurrently, to the additional therapeutic agent.

Patients or subjects treated in accordance with the methods described herein may already be receiving treatment, such as corticosteroid treatment. Patients or subjects treated in accordance with the methods described herein may be classified as 'corticosteroid responsive' or 'corticosteroid non-responsive'. The patient or subject may exhibit one or more symptoms associated with a chronic airway disease. In certain embodiments, the patient or subject may be an individual who is under medical care and/or actively seeking medical care for treatment of a chronic airway disease.

In certain embodiments, the patients or subjects treated in accordance with the methods described herein may be patients having disease characterised by high eosinophilia. In patients having high eosinophil levels, certain existing agents that target IL-4Rα, such as dupilumab, cannot be prescribed since the patient's circulating eosinophil levels would be unacceptably high. Without wishing to be bound by theory, it is thought that combined treatment with an IL-4Rα antagonist, for example an IL-4Rα antibody, and an IL-5 antagonist, for example an IL-5 antibody, will be suitable for patients having high eosinophil levels because IL-5 promotes eosinophil proliferation. Therefore, combined inhibition of IL-5 together with IL-4Rα, may prevent or reduce the increase in eosinophil levels seen with IL-4Rα antibody therapy.

INCORPORATION BY REFERENCE

Various publications are cited in the foregoing description and throughout the following examples, each of which is incorporated by reference herein in its entirety.

EXAMPLES

The invention will be further understood with reference to the following non-limiting examples.

Example 1: Generation of Neutralizing IL-4Rα and IL-5 Monoclonal Antibodies

A. Llama Immunization and Library Construction:

Two llamas, farmed outdoors according to the French animal welfare legislation, were immunized intramuscularly with recombinant mouse IL-4Rα-Fc in one shoulder and recombinant mouse IL-5 in the other shoulder (R&D Systems) and boosted weekly for six weeks. Briefly, they received 100 μg of IL-4Rα-Fc and 50 μg of IL-5, buffered in phosphate-buffered saline (PBS) and mixed with Incomplete Freund's Adjuvant (Sigma-Aldrich) for the first two weeks, and 50 μg of IL-4Rα-Fc and 25 μg of IL-5 for the remaining four weeks. Generation of Fab libraries was performed using the proprietary SIMPLE antibody platform as previously described (see WO2010/001251, the contents of which are incorporated herein in their entirety). Five days after the last immunization, 400 mL of blood containing peripheral blood lymphocytes was collected from the llamas, purified by centrifugation on a Ficoll-Paque gradient and used for extraction of total RNA. Total RNA was then converted into random primed cDNA using reverse transcriptase, and gene sequences encoding for VH-CH1 regions of llama IgG1 and VL-CL domains (kappa and lambda) were isolated and subcloned into a phagemid vector pCB3. The pCB3 vector allows expression of recombinant antibodies as Fab fragments fused to the phage pIII envelope protein.

In order to generate recombinant antibodies that bind to human IL-4Rα and human IL-5, parallel studies were performed. Llamas were immunized intramuscularly with recombinant human IL-4Rα-Fc and recombinant human IL-5, following the same protocol as described above.

B. Selection of Fabs Binding to IL-4Rα and IL-5:

The *E. coli* strain TG1 (Netherlands Culture Collection of Bacteria) was transformed using recombinant phagemids to generate Fab-expressing phage libraries (one lambda and one kappa library per immunized llama). Because the llamas were immunized with IL-4Rα coupled to a fragment crystallizable (Fc) part, a counter-selection against Fc binding antigen-binding fragment (Fab)-expressing phages was first performed with an irrelevant human Ab. The resulting Fab-expressing phages, having a diversity in the range of $10^8$-$10^9$, were then adsorbed on immobilized recombinant biotinylated IL-4Rα-Fc or IL-5, and eluted using trypsin as previously described (De Haard et al. (1999) *Journal of Biological Chemistry*, 274: 18218-30). Three rounds of selections were performed to enrich for phages expressing IL-4Rα or IL-5-specific Fabs. TG1 *E. coli* was finally infected with selected phages, and individual colonies were isolated. Secretions of Fabs into periplasm of *E. coli* strain TG1 were induced using isopropyl β-D-1-thiogalactopyranoside (Sigma-Aldrich) under low glucose concentrations (0.1% w/v) and the Fab-containing periplasmic fractions of bacteria were collected.

C. Fab Screening, Characterization and Production:

The binding of Fabs to their respective mouse or human targets and their ability to neutralize them was determined by surface plasmon resonance (SPR) using a Biacore 3000 apparatus (GE Healthcare). IL-4Rα-Fc and IL-5 were immobilized on a carboxymethyl dextran sensor chip (CM-5) using amine coupling in sodium acetate buffer (GE Healthcare). The Fab-containing periplasmic extracts were loaded with a flow rate of 30 μL/min. The Fab off-rates were measured over a 90s period.

D. Monospecific Ab Production, Purification and Characterization:

The cDNAs encoding the VH and VL (lambda or kappa) domains of potent neutralizing IL-4Rα- and IL-5-specific selected Fab fragments were engineered into two separate pUPE mammalian expression vectors comprising the cDNAs encoding the CH1, CH2 and CH3 domains of mouse IgG2a (or human IgG1), containing mutations that abrogate Ab effector functions mediated by the Fc receptor or the CL (lambda or kappa), respectively. Production (by transient transfection of mammalian cells) and purification (by protein A affinity chromatography) of the resulting best potent neutralizing anti-IL-4Rα and anti-IL-5 IgG2a (or IgG1) molecules was then performed as previously described (Basilico et al. (2014) *Journal of Clinical Investigation* 124: 3172).

The CDR, VH and VL sequences of the selected antibodies are shown in Tables 3-14 below.

TABLE 3

Heavy chain CDR sequences of Fabs binding to human IL-4Rα

| Fab clone | CDR1 | SEQ ID NO. | CDR2 | SEQ ID NO. | CDR3 | SEQ ID NO. |
|---|---|---|---|---|---|---|
| h4R5D1 | SYIMS | 1 | GISSGGGITAYADSVKG | 2 | GLLRVEGY | 3 |
| h4R3B2 | SYDMT | 4 | AINSGGGSTNYADSVKG | 5 | ALRTVVHDRRLFYIDS | 6 |
| h4R3D6 | SYSLT | 7 | TIKARGGTTLYADSVKD | 8 | PLYNNFAGDFGS | 9 |

TABLE 4

Light chain CDR sequences of Fabs binding to human IL-4Rα

| Fab clone | CDR1 | SEQ ID NO. | CDR2 | SEQ ID NO. | CDR3 | SEQ ID NO. |
|---|---|---|---|---|---|---|
| h4R5D1 | GLSSGSVTSSNYPG | 10 | ATASRHS | 11 | ALHKGTYV | 12 |
| h4R3B2 | GGNNIGSKSAQ | 13 | ADSRRPS | 14 | QVWDTSAW | 15 |
| h4R3D6 | QASQSISSYLA | 16 | GGSRLQT | 17 | LQDYSWPLT | 18 |

TABLE 5

VH and VL sequences of Fabs binding to human IL-4Rα

| Fab clone | VH | SEQ ID NO. | VL | SEQ ID NO. |
|---|---|---|---|---|
| h4R5D1 | QLQLVESGGGLVQPGGSLRLSCAASGFTFSSYIMSWVRQAPGKGLEWVSGISSGGGITAYADSVKGRFTISRDNAKNTLYLQMNSLKPDDTAVYYCVAGLLRVEGYWGQGTQVTVSS | 19 | QTVVTQEPSLSVSPGGTVTLTCGLSSGSVTSSNYPGWYQQTPGQAPRSLIYATASRHSGVPSRYSGSISGNKATLTITGAEPEDEADYYCALHKGTYVFGGGTKLTVL | 20 |
| h4R3B2 | QLQLVESGGGLVQPGGSLRLSCAASGFTFSSYDMTWVRQAPGKGLEWVSAIN | 21 | SYELTQSPSVSVALRQTAKITCGGNNIGSKSAQWYQQKPGQAPVLVIYADSRRPSGIPERFSG | 22 |

TABLE 5-continued

VH and VL sequences of Fabs binding to human IL-4Rα

| Fab clone | VH | SEQ ID NO. | VL | SEQ ID NO. |
|---|---|---|---|---|
|  | SGGGSTNYADSVKGRVTISRDNAKNTL YLQMNSLKPEDTAVYFCARALRTVVHD RRLFYIDSWGQGTQVTVSS |  | SNSGNTATLTVSGAQAEDEADYYCQVWDTSA VVFGGGTRLTVL |  |
| h4R3D6 | QVQLQESGGGLVQPGGSLRLSCAASG FTFSSYSLTWVRQAPGKGLEWVSTIKA RGGTTLYADSVKDRFTISRDNAKNTLYL LMNSLKPEDTAVYYCAKPLYNNFAGDF GSWGQGTTVTVSS | 23 | DIQMTQSPSSLSASLGDRVTITCQASQSISSYL AWYQQKPGQAPKLLIYGGSRLQTGVPSRFSG SGSGTSFTLTISGLETEDLATYYCLQDYSWPLT FGQGTKVELK | 24 |

TABLE 6

Heavy chain CDR sequences of Fabs binding to mouse IL-4Rα

| Fab clone | CDR1 | SEQ ID NO. | CDR2 | SEQ ID NO. | CDR3 | SEQ ID NO. |
|---|---|---|---|---|---|---|
| m4RMP36A1 | DYAMS | 25 | IISWNGEITHYAESMKG | 26 | NHYTLTWGYDY | 27 |
| m4RMP36B7 | SYYMA | 28 | HIHAGGSLTQYADSVKG | 29 | IYGDATSYDY | 30 |
| m4RMP36E12 | SYAMN | 31 | AISGGGSTRYADSVKG | 32 | SGFYSDYERRYRYLEV | 33 |

TABLE 7

Light chain CDR sequences of Fabs binding to mouse IL-4Rα

| Fab clone | CDR1 | SEQ ID NO. | CDR2 | SEQ ID NO. | CDR3 | SEQ ID NO. |
|---|---|---|---|---|---|---|
| m4RMP36A1 | QGGNFGRYYAS | 34 | GSSNSPS | 35 | QVWDSSGYK | 36 |
| m4RMP36B7 | AGTSSDIGGYNYVS | 37 | EVNKRAS | 38 | ASYRSNNNIV | 39 |
| m4RMP36E12 | QASQSIRPEIS | 40 | GASRLQT | 41 | LQDYSWPYS | 42 |

TABLE 8

VH and VL sequences of Fabs binding to mouse IL-4Rα

| Fab clone | VH | SEQ ID NO. | VL | SEQ ID NO. |
|---|---|---|---|---|
| m4RMP36A1 | EVQLVESGGGLVQPGGSLRLSCAAS GFTFDDYAMSWVRQAPGKGLEWVSII SWNGEITHYAESMKGRFTISRDNAKN TLYLQMNTLKSGDTAVYYCAKNHYTL TWGYDYWGQGTQVTVSS | 43 | NFMLTQPSAVSVSLGQTARITCQGGNFGRYY ASWYQQKPGQAPVQVIYGSSNSPSGIPERFS GSSSGDTATLTISGAQAEDEADYYCQVWDSS GYKFGGGTTLTVL | 44 |
| m4RMP36B7 | EVQLVESGGGLVQPGGSLRVSCAAS GFTFSSYYMAWVRQAPGKGLEWVSH IHAGGSLTQYADSVKGRFTISRDNAK STLYLQMNSLKPEDTALYYCVRIYGD ATSYDYWGQGTQVSVSS | 45 | HSAVTQPPSVSGSPGKTVTISCAGTSSDIGGY NYVSWYQQFPGTAPKLLIYEVNKRASGIPDRF SGSKSGNTASLSISGLQSEDEADYYCASYRSN NNIVFGGGTHLTVL | 46 |
| m4RMP36E12 | QVQLVESGGGLVQPGGSLRLSCAAS GFTFSSYAMNWVRQAPGKGLEWVSA ISGGGSTRYADSVKGRFTISRDNAKN TLYLQMNSLKPEDTAVYYCAKSGFYS DYERRYRYLEVWGQGTLVTVSS | 47 | DIQMTQSPSSLSASLGDRVTITCQASQSIRPEI SWYQQKPGQTPKLLIYGASRLQTGVPSRFSG GGSGTSFTLTISGLEAEDLATYYCLQDYSWPY SFGQGTKLEIK | 48 |

TABLE 9

Heavy chain CDR sequences of Fabs binding to human IL-5

| Fab clone | CDR1 | SEQ ID NO. | CDR2 | SEQ ID NO. | CDR3 | SEQ ID NO. |
|---|---|---|---|---|---|---|
| h5MP26H7 | SSFMS | 49 | TINGNGGTYYADSMKG | 50 | DWISGGYYFPALGY | 51 |
| h5MP90A9 | SSFMS | 49 | TINGNGGTYYADSMKG | 50 | DWISGGYYFPALGY | 51 |
| h5MP90D9 | SSFMS | 49 | TINGNGGTYYADSMKG | 50 | DWISGGYYFPALGY | 51 |
| h5MP90C8 | SSFMS | 49 | TINGNGGTYYADSMKG | 50 | DWISGGYYFPALGY | 51 |
| h5MP90E7 | SSFMS | 49 | TINGNGGTYYADSMKG | 50 | DWISGGYYFPALGY | 51 |
| h5MP90G7 | SSFMS | 49 | TINGNGGTYYADSMKG | 50 | DWISGGYYFPALGY | 51 |

TABLE 10

Light chain CDR sequences of Fabs binding to human IL-5

| Fab clone | CDR1 | SEQ ID NO. | CDR2 | SEQ ID NO. | CDR3 | SEQ ID NO. |
|---|---|---|---|---|---|---|
| h5MP26H7 | SYELTQSPSVSVAQTQTAKITC | 52 | WYQQKPGQAPVLAIY | 53 | GIPERFSGSNSGNTATLTITGAQAEDEADYYC | 54 |
| h5MP90A9 | SYELTQSPSLSVALRQTAKMTC | 55 | WYQQKPGQAPVLVIY | 56 | GIPERFAGSNAGNTATLTISGAQAEDEADYYC | 57 |
| h5MP90D9 | SYELTQSPSVSVALRQTAKITC | 58 | WYQQKPGQAPVLVIY | 56 | GIHERFSGSNSGNTATLTIGGAQAEDEADYYC | 59 |
| h5MP90C8 | SYELTQSPSVSVALRQTAKITC | 58 | WYQQSPGQAPVLVIY | 60 | GIPERFSGSNSGNTATLTISGARAEDEADYYC | 61 |
| h5MP90E7 | SYELTQSPSVSVALRQTAKITC | 58 | WYQQKPGQAPVLVIY | 56 | GIPERFSGSNSGNTATLTISGAQAEDEADYYC | 62 |
| h5MP90G7 | SYELTQSPSVSVALRQTAKITC | 58 | WYQQKPGQAPVLVIY | 56 | GIPERFSGSNSGNTATLTISGAQAEDEADYYC | 62 |

TABLE 11

VH and VL sequences of Fabs binding to human IL-5

| Fab clone | VH | SEQ ID NO. | VL | SEQ ID NO. |
|---|---|---|---|---|
| h5MP26H7 | EVQLVESGGGLVQPGGSLRLSCAASGFAFSSSFMSWVRQAPGKGLEWVSTINGNGGTYYADSMKGRFTISRDNVKSTVTLQMNSLKPEDTAVYYCADWISGGYYFPALGYWGQGTQVTVSS | 63 | SYELTQSPSVSVAQTQTAKITCGGDNIGSKSVQWYQQKPGQAPVLAIYADTRRPSGIPERFSGSNSGNTATLTITGAQAEDEADYYCQVWDTSTNVAVFGGGTRLTIL | 64 |
| h5MP90A9 | EVQLVESGGGLVQPGGSLRLSCAASGFAFSSSFMSWVRQAPGKGLEWVSTINGNGGTYYADSMKGRFTISRDNVKSTVTLQMNSLKPEDTAVYYCADWISGGYYFPALGYWGQGTQVTVSS | 63 | SYELTQSPSLSVALRQTAKMTCGGNKIGSKSAQWYQQKPGQAPVLVIYADSRRPSGIPERFAGSNAGNTATLTISGAQAEDEADYYCQVWDISANAAVFGGGTHLTVL | 65 |
| h5MP90D9 | EVQLVESGGGLVQPGGSLRLSCAASGFAFSSSFMSWVRQAPGKGLEWVSTINGNGGTYYADSMKGRFTISRDNVKSTVTLQMNSLKPEDTAVYYCADWISGGYYFPALGYWGQGTQVTVSS | 63 | SYELTQSPSVSVALRQTAKITCGGNNIGSLSTQWYQQKPGQAPVLVIYADNRRPSGIHERFSGSNSGNTATLTIGGAQAEDEADYYCQVWDNSANALVFGGGTHLTVL | 66 |
| h5MP90C8 | EVQLVESGGGLVQPGGSLRLSCAASGFAFSSSFMSWVRQAPGKGLEWVSTINGNGGTYYADSMKGRFTISRDNVKSTVTLQMNSLKPEDTAVYYCADWISGGYYFPALGYWGQGTQVTVSS | 63 | SYELTQSPSVSVALRQTAKITCGGDNIGSKSAQWYQQSPGQAPVLVIYADASRPSGIPERFSGSNSGNTATLTISGARAEDEADYYCQVWDTSTNAAVFGGGTHLTVL | 67 |
| h5MP90E7 | EVQLVESGGGLVQPGGSLRLSCAASGFAFSSSFMSWVRQAPGKGLEWVSTINGNGGTYYADSMKGRFTISRDNVKSTVTLQMNSLKPEDTAVYYCADWISGGYYFPALGYWGQGTQVTVSS | 63 | SYELTQSPSVSVALRQTAKITCGGNNIGSKSAQWYQQKPGQAPVLVIYADSRRPSGIPERFSGSNSGNTATLTISGAQAEDEADYYCQVWDVSTNAAVFGGGTHLSVL | 68 |

TABLE 11-continued

VH and VL sequences of Fabs binding to human IL-5

| Fab clone | VH | SEQ ID NO. | VL | SEQ ID NO. |
|---|---|---|---|---|
| h5MP90G7 | EVQLVESGGGLVQPGGSLRLSCAASGFAFSSS FMSWVRQAPGKGLEWVSTINGNGGTYYADSM KGRFTISRDNVKSTVTLQMNSLKPEDTAVYYCA ADWISGGYYFPALGYWGQGTQVTVSS | 63 | SYELTQSPSVSVALRQTAKITCGGNNIGRKSAQWYQQ KPGQAPVLVIYADSRRPSGIPERFSGSNSGNTATLTIS GAQAEDEADYYCQVWDSSANAAVFGGGTHLTVL | 69 |

TABLE 12

Heavy chain CDR sequences of Fabs binding to mouse IL-5

| Fab clone | CDR1 | SEQ ID NO. | CDR2 | SEQ ID NO. | CDR3 | SEQ ID NO. |
|---|---|---|---|---|---|---|
| m5MP31C2 | SYGMS | 70 | TISRGGDSTSYADSVKG | 71 | LGRLGFG | 72 |
| m5MP93C6 | SYGMS | 70 | TISRGGDSTSYADSVKG | 71 | LGRLGFG | 72 |
| m5MP95G7 | SYGMS | 70 | TISRGGDSTSYADSVKG | 71 | LGRLGFG | 72 |

TABLE 13

Light chain CDR sequences of Fabs binding to mouse IL-5

| Fab clone | CDR1 | SEQ ID NO. | CDR2 | SEQ ID NO. | CDR3 | SEQ ID NO. |
|---|---|---|---|---|---|---|
| m5MP31C2 | AGTSSDIGDWNYVS | 73 | EVNKRAS | 38 | TSYRSGNMAN | 74 |
| m5MP93C6 | AGTSSDIGDWNYVS | 73 | EVNKRAS | 38 | VSYRSGNMAN | 75 |
| m5MP95G7 | AGTSSDIGDWNYVS | 73 | EVNKRAS | 38 | TSYRSGNMAN | 74 |

TABLE 14

VH and VL sequences of Fabs binding to mouse IL-5

| Fab clone | VH | SEQ ID NO. | VL | SEQ ID NO. |
|---|---|---|---|---|
| m5MP31C2 | ELQVVESGGGLVQPGGSLRLSCAASG FTFSSYGMSWVRQAPGKGLEWVSTIS RGGDSTSYADSVKGRFTISKDNAKNTL YLQMNSLEPEDTAVYYCANLGRLGFG RGQGTQVTVSS | 76 | SSALTQPPSMSGTLGKTLTISCAGTSSDIGDW NYVSWFQQLPGTAPKLLISEVNKRASGIPDRF SGSKSGNTASLSISGLQSEDEADYYCTSYRSG NNWVFGGGTHLTVL | 77 |
| m5MP93C6 | ELQVVESGGGLVQPGGSLRLSCAASG FTFSSYGMSWVRQAPGKGLEWVSTIS RGGDSTSYADSVKGRFTISKDNAKNTL YLQMNSLEPEDTAVYYCANLGRLGFG RGQGTQVTVSS | 76 | QAGLTQPPSMSGTLGKTLTISCAGTSSDIGDW NYVSWYQQLPGTAPKLLIYEVNKRASGIPDRF SGSKSGNTASLSISGLQSEDEADYYCVSYRSG NNWVFGGGTHLTVL | 78 |
| m5MP95G7 | ELQVVESGGGLVQPGGSLRLSCAASG FTFSSYGMSWVRQAPGKGLEWVSTIS RGGDSTSYADSVKGRFTISKDNAKNTL YLQMNSLEPEDTAVYYCANLGRLGFG RGQGTQVTVSS | 76 | SYELTQPPSVSGSPGKTLTISCAGTSSDIGDW NYVSWFQQLPGTAPKLLISEVNKRASGIPDRF SGSKSGNTASLSISGLQSEDEADYYCTSYRSG NNWVFGGGTHLTVL | 79 |

Example 2: In Vitro Characterisation of IL-4Rα and IL-5 mAbs

The mouse IL-4Rα and IL-5 mAbs (m4RMP36B7 and m5MP95G7) were tested for their ability to bind to their respective targets in vitro and to inhibit cellular effects mediated by IL-4Rα and IL-5 signalling.

A. Inhibition of IL4- and IL5-Induced HT-2 and TF-1 Cell Proliferation:

The neutralizing activity of both IL-4Rα and IL-5 monospecific Abs was assessed in in vitro cellular assays, in which mouse IL-4 and mouse IL-5 induce the proliferation of HT-2 and TF-1 cells, respectively.

Human TF-1 cells (erythroblasts, ATCC® CRL-2003™) and mouse HT-2 clone A5E cells (IL-2 dependent T lymphocytes, ATCC® CRL-1841™) were cultured at 37° C. with κ% (v/v) $CO_2$ in growth medium containing RPMI 1640 (Sigma), 10% (v/v) heat-inactivated fetal bovine serum (Sigma), 1×gentamycin (Sigma), and 2 ng/mL human granulocyte-macrophage colony-stimulating factor (R&D Systems) or human IL-2 (R&D Systems), respectively. Assay medium was growth medium without human GM-CSF for the TF-1 cells or human IL-2 for the HT-2 cells. 0.5 ng/mL mouse IL-5 (R&D Systems) for the TF-1 cells or mouse IL-4 (R&D Systems) for the HT-2 cells was added to the assay medium. Abs were serially diluted 10-fold for the TF-1 cells or 5-fold for the HT-2 cells in assay medium containing 1 ng of mouse IL-5 for the TF-1 cells or 0.75 ng of mouse IL-4 for the HT-2 cells. Cells were incubated for 1 h at 37° C. before being washed and resuspended at a final volume of $1.1 \times 10^6$ cells/mL for the TF-1 cells or $0.2 \times 10^6$ cells/mL for the HT-2 cells. Cells were then added to each well before addition of the CellTiter 96® AQueous One Solution Reagent (Promega). After 3 h of incubation, the absorbance was measured.

As shown in FIG. 1, IL-4Rα (square) and IL-5 (triangle) monospecific Abs potently inhibited mouse IL-4- and IL-5-induced HT-2 and TF-1 cell proliferation, respectively. Specifically, IL-4Rα and IL-5 Abs could block the cellular proliferation induced by mouse IL-4 and IL-5 with an EC50 equal to 0.2 nM and 0.6 nM, respectively.

B. Binding of IL-4Rα and IL-5 mAbs to IL-4Rα and IL-5, Respectively:

FIG. 2 shows representative surface plasmon resonance (SPR) sensorgrams of the interactions between the mAbs (IL-4Rα Abs, IL-5 Abs or irrelevant IgG2a Abs) at varying concentrations (0-20 µg/mL) and the immobilized target (IL-4Rα or IL-5). Both mAbs bound to their targets, whereas the irrelevant IgG2a did not bind to either target. IL-4Rα and IL-5 monospecific Abs bound their target with an affinity of 8E-11 M and 2E-12 M, respectively.

Additionally, the ability of the monospecific Abs to compete with their targets was tested on SPR. FIG. 3 shows a representative SPR sensorgram of the competitive interactions between a mixture composed of a mAb (IL-4Rα, IL-5 or irrelevant IgG2a) and its target (IL-4Rα or IL-5), and the immobilized proteins (IL-4, IL-13Rα or IL-5Rα). A mixture composed of IL-4Rα mAb and IL-4Rα inhibited binding of IL-4Rα to the immobilized IL-4 ligand. A mixture composed of IL-4Rα mAb and IL-13 inhibited binding of IL-13 to the immobilized IL-13Rα. Similarly, a mixture composed of IL-5 mAb and IL-5 inhibited binding of IL-5 to the immobilized IL-5Rα.

C. Inhibition of IL-4 Induced MHC Class II Antigens of Purified B Cells Analysed by FACS:

FACS analysis was used to test whether IL-4Rα monospecific Ab could compete with mouse IL-4, which is known to induce the translocation of MHC class II to the surface of B cells.

For the FACS analysis, B cells were collected using magnetic-activated cell sorting mouse anti-CD19 microbeads (Miltenyi Biotec) following the manufacturer's protocol. Purified B cells ($5 \times 10^5$ cells/mL) were cultured for 16 h in 24-well plates (Costar) with or without IL-4 (0.1 ng/mL) in the presence of anti-IL-4Rα or an irrelevant IgG2a Ab at 500 ng/mL or medium control with or without inhibitors. Cells were washed and preincubated for 20 min on ice with the rat IgG2b anti-murine FcγR monospecific Ab 2.4G2 (Bioceros) to block IgG Fc receptors. Cells were then stained with Abs directed against MHC class II (M5/114.15.2, eBioscience) and CD19 (1D3, eBioscience) before being incubated for 30 min at 4° C. then washed. Dead cells were excluded from the analysis by using a fixable viability dye (eFluor506, eBioscience). Stained cells were analyzed on a LSR Fortessa flow cytometer (BD Biosciences). Final analysis and graphic output were performed with FlowJo v10.0.7 software (Tree Star).

As shown in FIG. 4, MHC class II antigen expression on B cells was significantly greater in the presence of IL-4 than without IL-4. The IL-4Rα mAb potently inhibited IL-4 induced-MHC class II antigen expression of purified B cells.

Example 3: In Vivo Characterisation of Anti-Mouse IL-4Rα and IL-5 mAbs in a Murine House Dust Mite (HDM) Model House dust mites (HDMs—*Dermatophagoides* sp.) are one of the most common allergens worldwide. 50-85% of asthmatics are HDM allergic. Prolonged exposures to HDM leads to remodelling of the airways with increased mucus cell density and airway hyperresponsiveness, which remains elevated after discontinuation of HDM exposure. The murine HDM model is an effective in vivo model for the study of asthma.

Figure 5A:
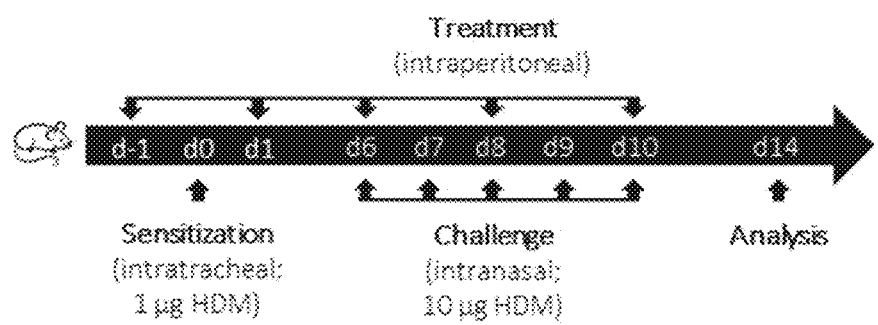
FIGS. 5A-5B show the results of an experiment to test the effects of IL-4Rα and IL-5 mAbs in an in vivo murine model of asthma.

Experimental Set-Up 1:

Female C57Bl/6J wild-type mice were obtained from The Jackson Laboratory. Experiments were approved by the ethical committee of the VIB-UGent Center for Inflammation Research. All mice were used between 6-8 weeks of age. Experiments were carried out using age-matched groups. The experimental design, as shown in FIG. 5A, involved Ab treatments administered during the entire sensitization and challenge period. On day 0, mice were lightly anesthetized with isofluorane (2.5% in air) and received 1 µg HDM (Greer Laboratories) intra-tracheally. On days 6-10, mice were lightly anesthetized with isofluorane (2.5% in air) and challenged daily with 10 µg HDM intranasally. On days −1, 1, 6, 8 and 10, mice received treatment with either: (i) IL-4Rα monospecific Ab (m4RMP36B7); (ii) IL-5 monospecific Ab (m5MP95G7); (iii) the combination of IL-4Rα and IL-5 monospecific Abs (m4RMP36B7 and m5MP95G7); or (iv) an irrelevant IgG2a Ab. Days −1 and 1 represented the sensitization phase and days 6, 8 and 10 represented the challenge phase. At least n=6 mice were treated per group.

A. Potent Neutralizing IL-4Rα and IL-5 mAbs Injected in Combination in a Murine HDM Model of Asthma Decrease Eosinophilia:

Collection and analysis of BAL fluid. On day 14, mice were euthanized. Bronchoalveolar lavage (BAL) was performed using 3×1 mL of EDTA-containing PBS into the cannulated trachea, and the cellular composition of the BAL fluid was determined by fluorescence-activated cell sorting (FACS) as previously described (Deckers et al. (2017) *Journal of Allergy and Clinical Immunology* 140(5), 1364-1377; Dullaers et al. (2017) *Journal of Allergy and Clinical Immunology*, 140:76-88; Schuijs et al. (2015)*Science,* 349: 1106-10).

Figure 5B:
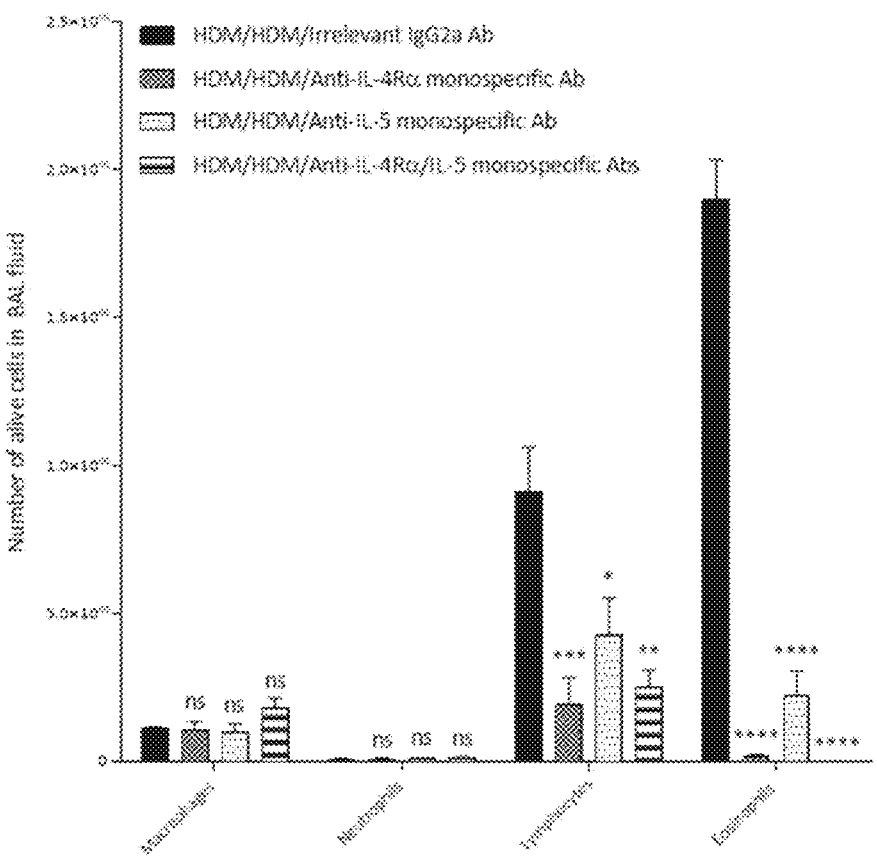
Figure 6:
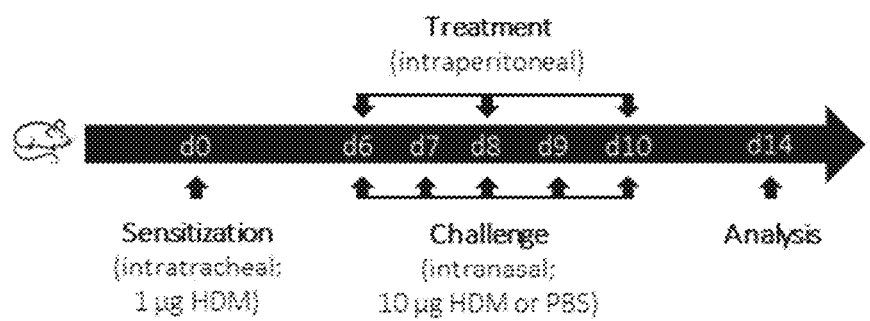
FIG. 6 is a diagrammatic representation of an experimental setup using a house dust mite (HDM) mouse model as an in vivo murine model of asthma. IL-4Rα and IL-5 antibody treatments were delivered by injection to HDM-treated C57BL/6J mice only during the challenge phase.

FIG. 5B shows the broncheoalveolar lavage fluid differential cell counts of mice that received IL-4Rα mAb, IL-5 mAb, a combination of an IL-4Rα mAb and an IL-5 mAb or an irrelevant IgG2a Ab. The cells were counted by FACS analysis. Eosinophil cell counts were increased by allergen challenge in IgG2a treated HDM-sensitized mice. A significant reduction in eosinophil cell counts was observed after treatment with the combination of the IL-4α/IL-5 monospecific Abs, as compared to treatment with a control IgG2a Ab. Experimental Set-Up 2:

A second experimental protocol was designed to further test the effects of the IL-4Rα and IL-5 antibodies in the murine HDM model in a clinically relevant therapeutic setting. The experimental design as shown in FIG. 6, differed from the experimental set-up in FIG. 5A, in that the procedure involved Ab treatments administered only during the challenge phase, and not during the sensitization phase. Thus, mice received their treatment (IL-4Rα monospecific Ab; IL-5 monospecific Ab; IL-4Rα/IL-5 monospecific Abs or an irrelevant IgG2a Ab) 4 hours before the challenge on days 6, 8 and 10 only. Mice received either 150 µg of each monospecific Ab, 150 µg of each monospecific injected in combination or 150 µg of irrelevant mouse IgG2a mAb. At least n=6 mice were treated per group.

Figure 10A:
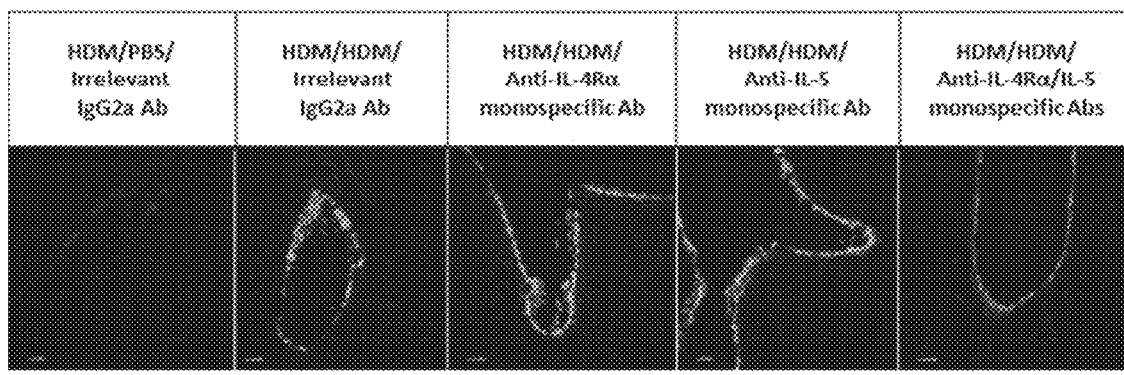
FIGS. 10A-10B show expression of the mucin, MucSAC, Agr2, and Spdef in the lungs of mice treated with IL-4Rα monospecific Ab, IL-5 monospecific Ab and a combination of IL-4Rα/IL-5 monospecific Abs.
Figure 10B:
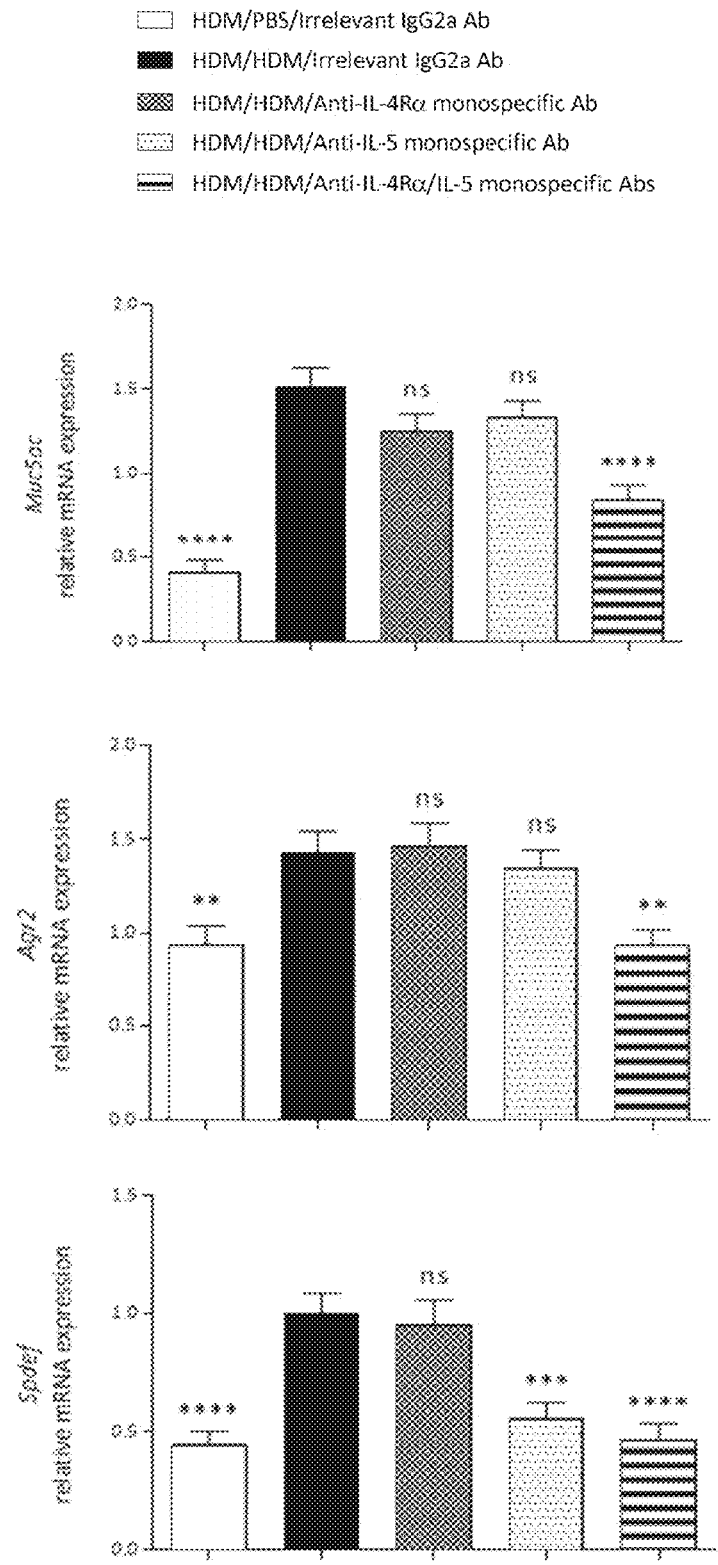
Figure 11:
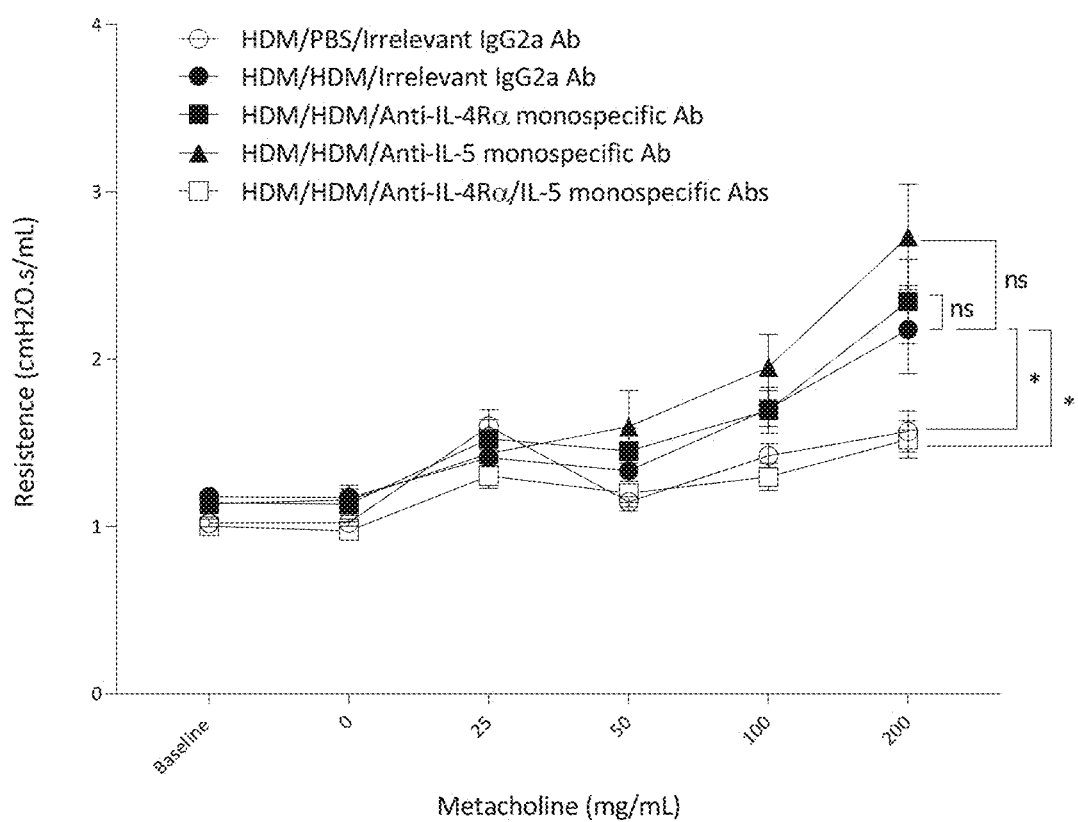
FIG. 11 shows bronchial hyperresponsiveness (BHR) measured after exposure to increasing doses of methacholine using flexiVent (SCIREQ®). Data are representative of three independent experiments, with at least n=6 mice per group. Bronchial hyperresponsiveness was significantly decreased after treatment with the combination of IL-4Rα/IL-5 monospecific Abs, as compared to treatment with a control IgG2a Ab, and resistance levels returned to the level as observed in unchallenged mice receiving only PBS. Results are expressed as mean±SEM. P values reflect the one-way ANOVA test, ns: not significant, *P≤0.05 versus an irrelevant IgG2 Ab.

Mice treated according to this protocol were subsequently assessed for: total count of inflammatory cells in the BAL fluid (FIG. 7); cytokine production in the mediastinal lymph nodes (FIG. 8); serum immunoglobulin production (FIG. 9); indications of goblet cell metaplasia (FIGS. 10A-10B); and bronchial hyperresponsiveness (FIG. 11).

A. Potent Neutralizing IL-4Rα and IL-5 mAbs Injected in Combination in a Murine HDM Model of Asthma Decrease Eosinophilia:

Collection and analysis of BAL fluid. On day 14, mice were euthanized. Bronchoalveolar lavage (BAL) was performed using 3×1 mL of EDTA-containing PBS into the cannulated trachea, and the cellular composition of the BAL fluid was determined by fluorescence-activated cell sorting (FACS) as previously described (Deckers et al. (2017) *Journal of Allergy and Clinical Immunology* 140(5), 1364-1377; Dullaers et al. (2017) *Journal of Allergy and Clinical Immunology*, 140:76-88; Schuijs et al. (2015) *Science*, 349: 1106-10).

Figure 7:
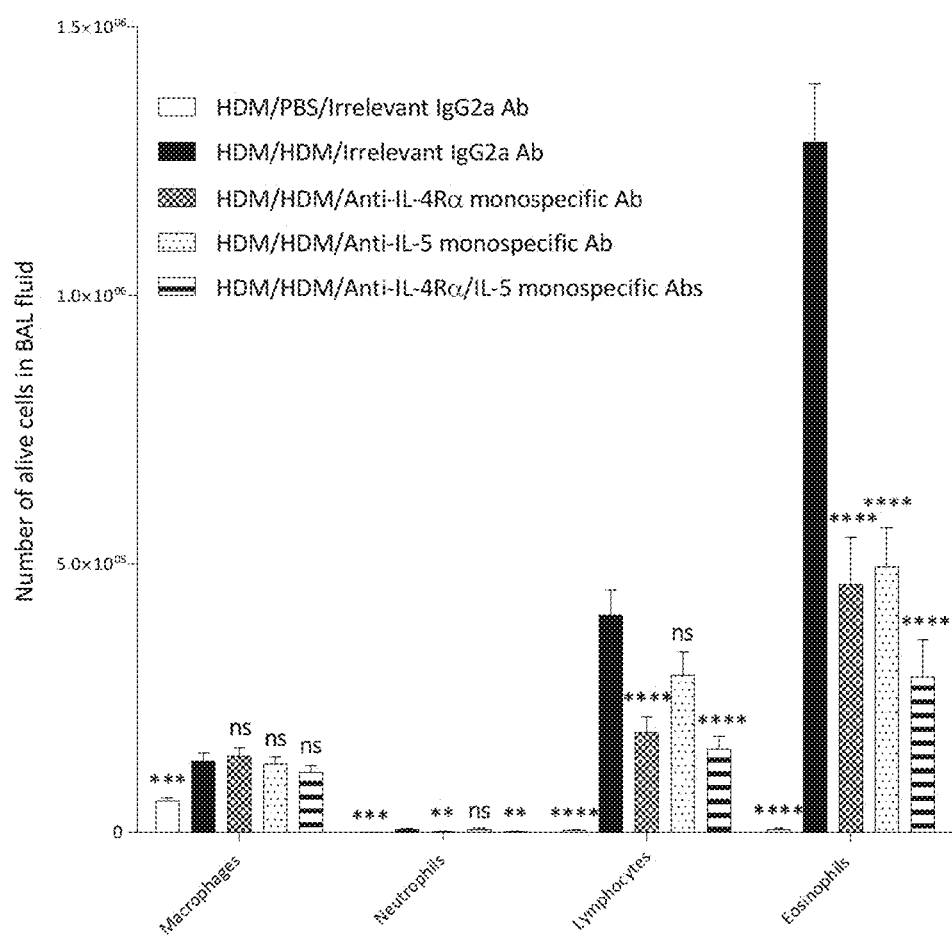
FIG. 7 shows BAL differential cell counts of mice that received IL-4Rα monospecific Ab, IL-5 monospecific Ab, a combination of the IL-4Rα/IL-5 monospecific Abs, or an irrelevant IgG2a Ab, as analysed by FACS. Eosinophil cell counts were increased by allergen challenge in IgG2a treated HDM-sensitized mice. A significant reduction in eosinophil cell counts was observed after treatment with IL-4Rα monospecific Abs or after treatment with IL-5 monospecific Abs, as compared to treatment with a control IgG2a Ab. A further reduction in eosinophil cell counts is observed after treatment with the combination of the IL-4α/IL-5 monospecific Abs. P values reflect the one-way ANOVA test, ns: not significant, P≤0.01, *P≤0.001, ****P≤0.0001 versus a control IgG2 Ab.

FIG. 7 shows BAL differential cell counts of HDM-treated mice that received IL-4Rα mAb, IL-5 mAb, IL-4Rα/IL-5 combined mAbs, or an irrelevant IgG2a Ab, as analysed by FACS. In irrelevant IgG2a Ab-treated mice, airway HDM exposures increased the total count of inflammatory cells in BAL fluid compared to PBS challenged mice. More specifically, it increased the numbers of eosinophils, lymphocytes and macrophages. Interestingly, the numbers of eosinophils were significantly decreased after treatment with the monotherapies, as compared to treatment with a control IgG2a Ab. The lowest numbers of eosinophils were seen in mice treated with the combination therapy.

B. IL-4Rα mAb and the IL-4Rα/IL-5 mAbs in Combination Reduce Cytokine Production:

The effect of the IL-4Rα and IL-5 mAbs on production of cytokines by allergen-restimulated mesenteric lymph node (MLN) cells was tested in vitro. Single cell suspensions (2×10⁶ cells/mL) were obtained from MLNs by homogenizing the organ through a 100 µm cell sieve. Cells were restimulated ex vivo with 15 µg/mL HDM for 3 days in 96 round-bottom plates and supernatants were collected to determine the cytokine production by using the Read-SET-Go!® ELISA sets (eBioscience).

As shown in FIG. 8, the in vitro production of effector cytokines IL-5 and IL-13 in allergen-re-stimulated cultures of MLN cells was boosted by allergen challenge in IgG2a treated HDM-sensitized mice. However, this response was significantly decreased after treatment with IL-4Rα monospecific Ab and the combination of IL-4Rα and IL-5 mAbs whereas IL-5 monospecific Ab had no significant effect.

C. IL-4Rα mAb and the IL-4Rα/IL-5 mAbs in Combination Reduce the Production of HDM-Specific IgE and IgG1:

Blood was obtained from the iliac vein, the serum was then prepared and the quantities of HDM-specific IgG1 and IgE were determined as previously described (Schuijs et al. (2015) *Science*, 349:1106-10).

Figure 9:
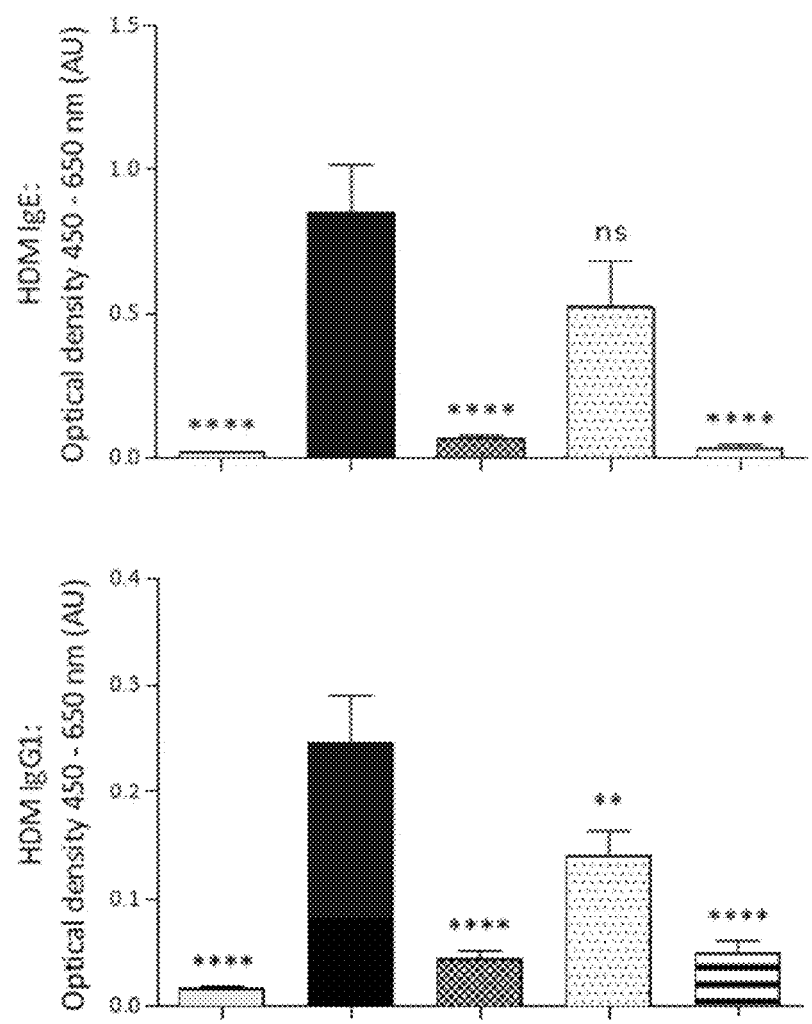
FIG. 9 shows serum levels of HDM-specific IgE and IgG1, after treatment with IL-4Rα monospecific Ab, IL-5 monospecific Ab, a combination of IL-4Rα/IL-5 monospecific Abs, or an irrelevant IgG2a Ab, determined by ELISA. The serum concentration of HDM-specific IgG1 and IgE was boosted by allergen challenge in IgG2a Ab treated mice. The IL-4Rα mAb and the IL-4Rα/IL-5 mAb combination were able to significantly reduce this increase in allergen-induced IgG1 and IgE. P values reflect the one-way ANOVA test, *P≤0.05, ns: not significant, P≤0.01, **P≤0.0001, versus an irrelevant IgG2 Ab.

As shown in FIG. 9, the serum concentration of HDM-specific IgG1 and IgE was boosted by allergen challenge in IgG2a Ab treated mice. The IL-4Rα mAb and the IL-4Rα/IL-5 mAb combination were able to significantly reduce this increase in allergen-induced IgG. The IL-4Rα mAb, the IL-5 mAb, and the IL-4Rα/IL-5 mAb combination were able to significantly reduce the increase in allergen-induced IgE.

D. IL-4Rα and IL-5 mAbs in Combination Reduce the Expression of Muc5AC and Agr2:

Mucin expression in the lungs was assessed by immunostaining. Lungs were injected with PBS/OCT (1:1) solution, snap-frozen in liquid nitrogen and kept at −80° C. until further processing for Muc5AC immunofluorescence staining as previously described (Deckers et al. (2017) *Journal of Allergy and Clinical Immunology* 140(5), 1364-1377).

Goblet cell metaplasia (GCM) is driven by IL-13 and characterized by increased production of Muc5AC, a gel-forming mucin present in the airways of asthmatic mice and humans. In IgG2a Ab-treated and HDM-sensitized mice, HDM challenge upregulated Muc5AC expression in the airway epithelium, as compared with PBS challenge (FIG. 10A). The increased staining for Muc5AC was not affected by IL-4Rα or IL-5 Ab monotherapies. Strikingly however, lungs from mice treated with the combination of IL-4Rα/IL-5 Abs had strongly reduced staining intensity for Muc5AC compared to the other HDM-sensitized and challenged groups.

To confirm and quantify the effects of the IL-4Rα and IL-5 mAbs on GCM, the mRNA expression level of MucSac, as well as another IL-13/STAT6 downstream target gene involved in GCM, Agr2, were then measured by qRT-PCR in lung tissues.

Lungs were snap-frozen in liquid nitrogen and kept at −80° C. until further processing for real-time quantitative reverse transcription polymerase chain reaction (qRT-PCR) as previously described (Dullaers et al. (2017) *Journal of Allergy and Clinical Immunology,* 140:76-88). Briefly, RNA was obtained by using the TriPure Isolation Reagent (Roche, Mannheim, Germany) and isolated according to the manufacturer's instructions. RNA was reverse transcribed with a Transcriptor High Fidelity cDNA Synthesis Kit (Roche), and samples were analyzed by using SYBR green-based qRT-PCR with a LightCycler 480 system (Roche) against reference genes (Rpl13a, Hprt and Sdha).

As shown in FIG. 10B, the mRNA expression levels of these two genes were induced by HDM challenge in mice. The IL-4Rα and IL-5 antibodies alone did not significantly reverse this increase in MucSac or Agr2 mRNA levels. However, the combination of an IL-4Rα mAb and an IL-5 mAb significantly reduced the HDM-mediated increase in MucSac or Agr2 mRNA levels.

E. IL-4Rα and IL-5 mAbs in Combination Reduce Lung Resistance:

Bronchial hyperresponsiveness (BHR) is the tendency of the airways to constrict in response to low amounts of bronchoconstrictor agents like the muscarinic receptor agonist methacholine. Lung function was performed using an invasive measurement of dynamic resistance (Flexivent, Scireq).

24 h after the last HDM challenge, nonspecific airway responsiveness was measured by exposing awake mice to aerosolized PBS to set a baseline value, followed by increasing concentrations of aerosolized metacholine (0-400 μg/kg-1) using ultrasonic nebulizers. For invasive measurement of dynamic resistance, mice were anesthetized with urethane, tracheotomized, and intubated with an 18-G catheter, followed by mechanical ventilation with a Flexivent apparatus (SCIREQ). Respiratory frequency was set at 120 breaths/min with a tidal volume of 0.2 mL, and a positive-end expiratory pressure of 2 mL $H_2O$ was applied. Dynamic resistance was recorded after a standardized inhalation manoeuvre given every 10 s for 2 min. Baseline resistance was restored before administering the subsequent doses of metacholine.

As shown in FIG. 11, in control IgG2a Ab-treated mice, HDM challenged and sensitized mice, methacholine caused increased airway resistance compared to PBS challenged HDM sensitized mice. Treatment with the IL-5 and IL-4Rα antibodies did not significantly reduce BHR. However, mice treated with the combination of IL-4Rα and IL-5 mAbs were completely protected from developing BHR. These results demonstrate the synergistic effects of the IL-4Rα/IL-5 antibody combination in treating a fundamental aspect of chronic airway disease.

Altogether these results showed that the combination of aIL-5 and aIL-4Rα monospecific Abs given during challenge in HDM-treated mice had synergistic effects on key aspects of asthma, including GCM and BHR.

Statistical analysis was performed by using GraphPad Prism software v7.01 and Genstat software v19. For all experiments, results were expressed as mean±standard error of the mean (SEM) and the difference between groups was calculated using the one-way ANOVA test. Differences between groups were considered significant when $*P \leq 0.05$, $P \leq 0.01$, $*P \leq 0.001$ and $****P \leq 0.0001$, versus the group of mice sensitized and challenged with HDM and treated with a control IgG2 Ab.

Example 4: Generation and In Vitro Characterisation of an IL-4Rα/IL-5 Bispecific Antibody An IL-4Rα/IL-5 bispecific antibody was generated using the sequences of the 4RMP36B7 IL-4Rα antibody and the 5MP95G7 IL-5 antibody. The Fc portions of the antibodies were modified so as to include the "Knob-into-hole"-like mutations which facilitate the correct chain pairing in the context of the bispecific antibody (Ridgway et al. (1996) *Protein Engineering, Design and Selection*, 9:617-21). In particular, the IL-4Rα antibody 4RMP36B7 was engineered in the CH3 domain of the murine Fc region to introduce the substitutions T366S, L368A and Y407V. The IL-5 antibody 5MP95G7 was engineered in the CH3 domain of the murine Fc region to introduce the substitution T366W.

Figure 12:
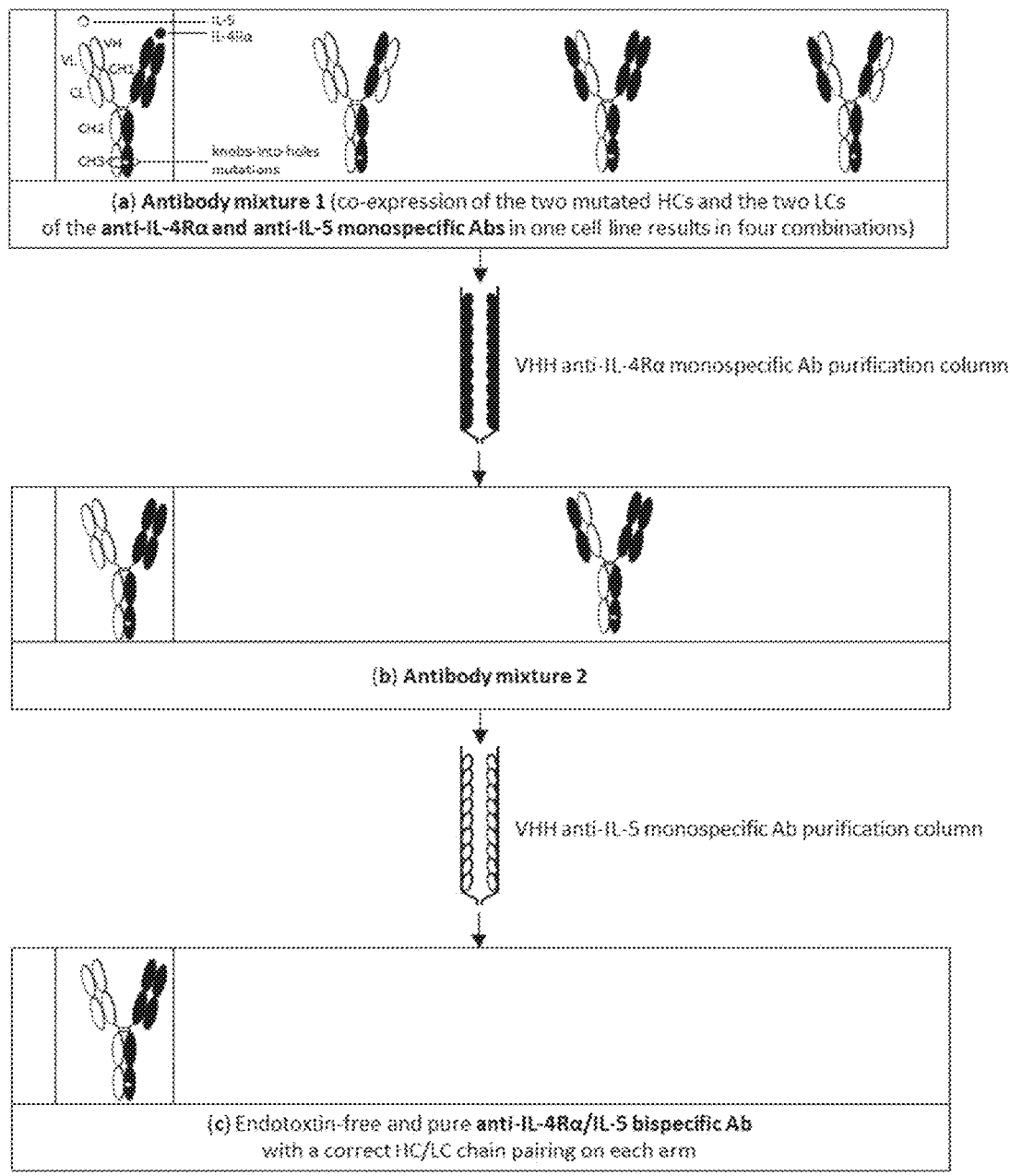
FIG. 12 is a schematic representation of the dual anti-idiotypic purification process to isolate a desired and properly paired bispecific IL-4Rα/IL-5 Ab (a) From a mixture of four possible combinations formed by different heavy chain and light chain pairings, an anti-idiotypic VHH recognizing only the correct HC/LC pairing of the IL-4Rα monospecific Ab was used to extract the Abs containing this pairing (b) A second anti-idiotypic column containing a VHH antibody recognizing only the correct HC/LC pairing of the IL-5 monospecific Ab was used to collect the bispecific Ab containing the properly paired HC/LC of alL-5 monospecific Ab. (c) This led to the isolation of the desired IL-4Rα/IL-5 bispecific Ab with correct HC/LC pairings.

The two mutated heavy chains and two light chains of the IL-4Rα and IL-5 antibodies were co-expressed and bispecific antibodies comprising the correct heavy chain-light chain pairing were purified using anti-idiotypic VHH antibodies, as described in Godar et al. (2016, Scientific Reports, 6:31621). This purification process is represented schematically in FIG. 12.

The purity of the IL-4Rα/IL-5 bispecific antibody was confirmed using high resolution spectrometry and the dual targeting properties of this antibody were confirmed by BIAcore.

Figure 13A:
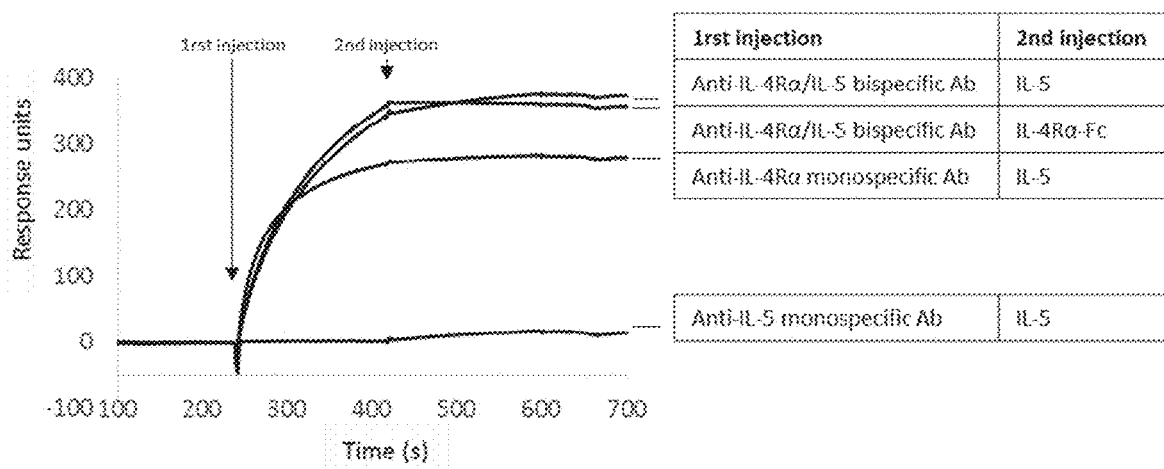
FIGS. 13A-13B validate the dual targeting properties of the IL-4Rα/IL-5 bispecific antibodies.
Figure 13B:
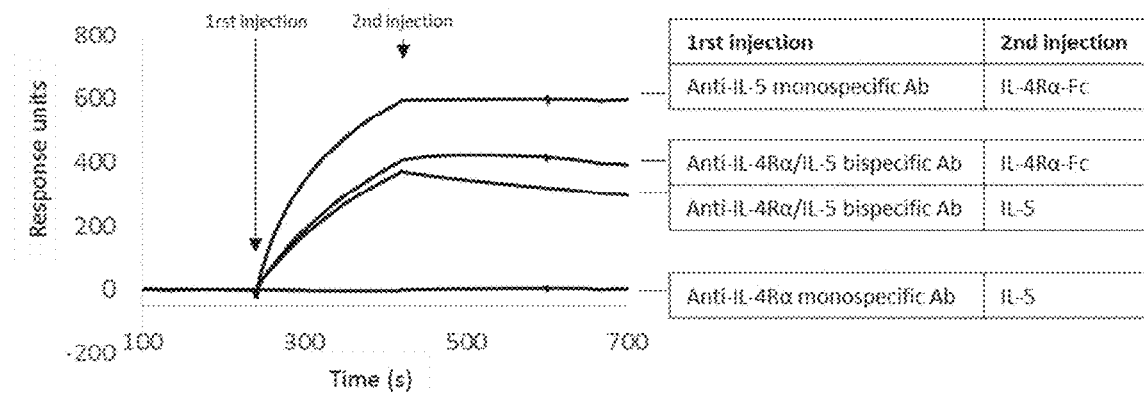

A. Binding of the IL-4Rα/IL-5 Bispecific Ab to IL-4Rα and IL-5:

The bispecific properties of the IL-4Rα/IL-5 Ab was confirmed using SPR, as shown in FIGS. 13A-13B. The bispecific Ab bound specifically to chip-immobilized IL-4Rα-Fc, and an increased signal was observed when IL-5 was then added, indicating that the bispecific Ab was able to simultaneously bind to coated IL-4Rα and to IL-5 in solution (FIG. 13A). The experiment was also performed in reverse order and confirmed the bispecific nature of the molecule as depicted in FIG. 13B.

Taken together, these results show that the dual anti-idiotypic approach allowed the isolation of a pure and functional IL-4Rα/IL-5 bispecific Ab.

Example 5: In Vivo Characterisation of Anti-Mouse IL-4Rα/IL-5 Bispecific Antibody in a Murine HDM Model The IL-4Rα/IL-5 bispecific antibody generated in Example 4 was tested in the murine HDM model described in Example 3 above. The experimental protocol is as shown in FIG. 14. Mice were subjected to the HDM sensitization and challenge protocol and treated with the Abs during the challenge phase only.

The in vivo activity of the IL-4Rα/IL-5 bispecific Ab was compared with the monotherapies (IL-4Rα or IL-5 monospecific Ab) and the combination (αIL-4Rα/αIL-5 monospecific Abs). To compare equimolar inhibition of targets, and to eliminate differences in the total amount of Ab, the antibodies were dosed as follows: 75 μg of each monospecific Ab combined with 75 μg of an irrelevant IgG2a Ab for the testing of individual Abs; 75 μg of each monospecific Ab injected in combination; and 150 μg of the bispecific Ab.

Figure 18:
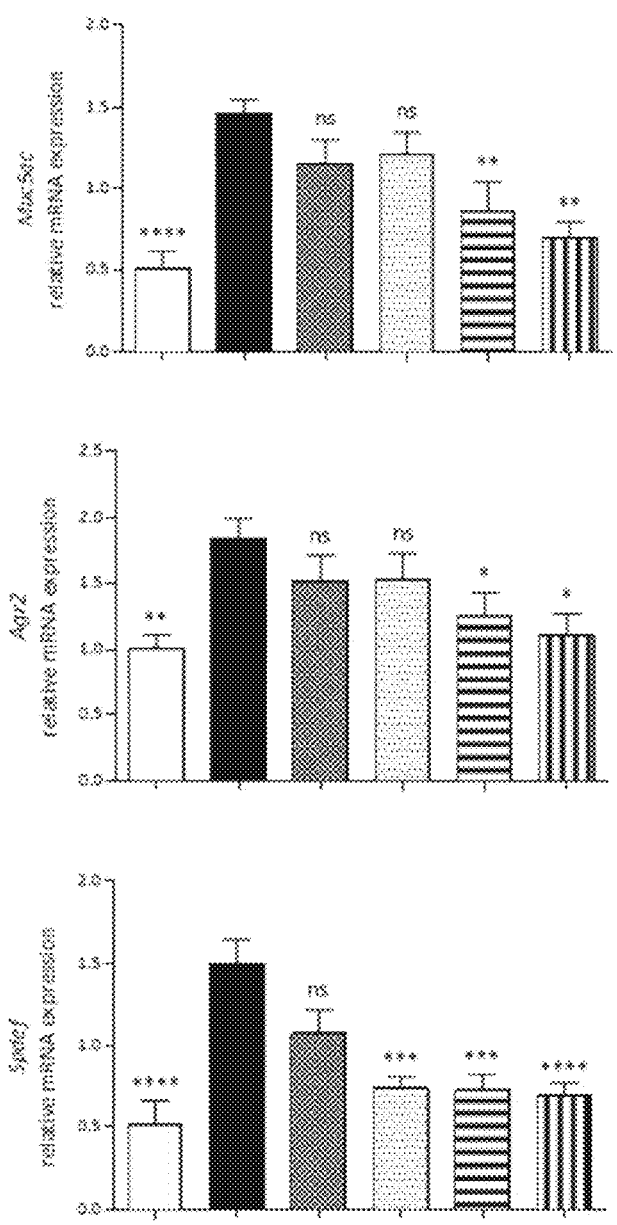
FIG. 18 shows lung mRNA expression levels of MucSac, Agr2, and Spdef determined by qRT-PCR. The mRNA expression levels of these two genes were induced by HDM challenge in mice compared to PBS challenge. The IL-4Rα and IL-5 antibodies alone did not significantly reverse this increase in MucSac or Agr2 mRNA levels. However, the combination of both monospecific IL-4Rα mAb and an IL-5 mAb, and the IL-4Rα/IL-5 bispecific Ab, significantly reduced the HDM-mediated increase in MucSac or Agr2 mRNA levels. P values reflect the one-way ANOVA test, ns: not significant, *P≤0.05, P≤0.01, **P≤0.0001 versus an irrelevant IgG2 Ab.
Figure 19:
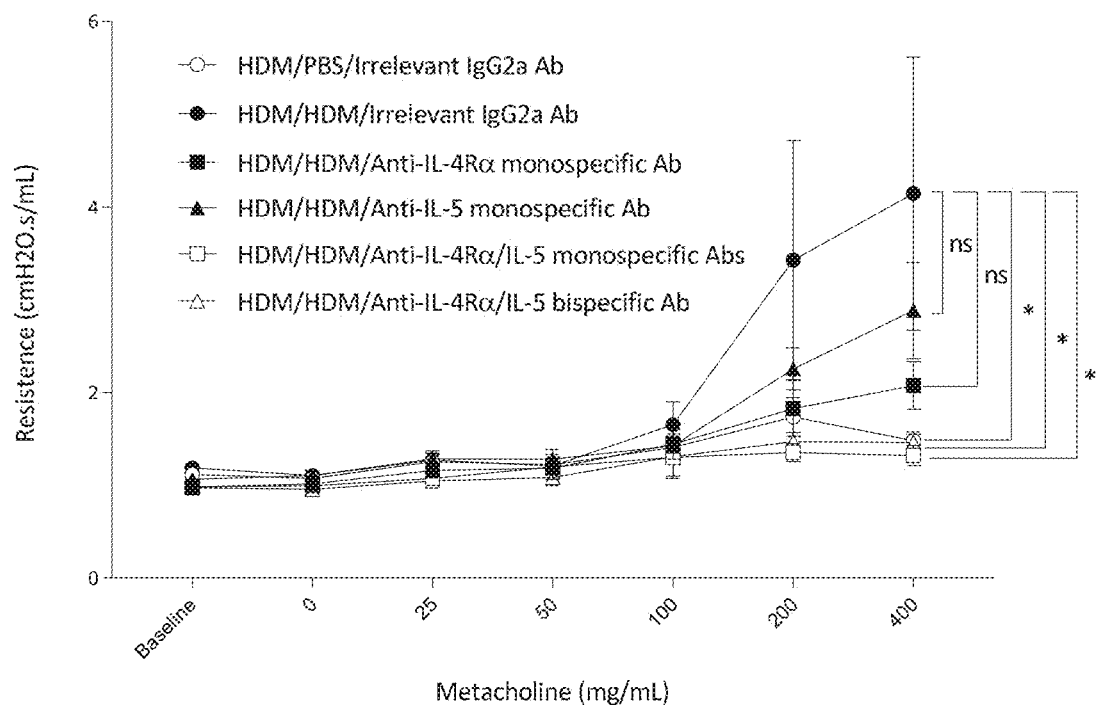
FIG. 19 shows BHR measured after exposure to increasing doses of methacholine using flexiVent (SCIREQ®). Data are representative of two independent experiments, with n=6 mice per group. Bronchial hyperresponsiveness was significantly decreased after treatment with the combination of IL-4Rα/IL-5 monospecific Abs, and after treatment with the IL-4Rα/IL-5 bispecific Ab, as compared to treatment with a control IgG2a Ab. Resistance levels after treatment with the combination of monospecific Abs or after treatment with the bispecific Abs returned to the level as observed in unchallenged mice receiving only PBS. Results are expressed as mean±SEM. P values reflect the one-way ANOVA test, ns: not significant, *P≤0.05 versus irrelevant IgG2a Ab.

Mice treated according to this protocol were subsequently assessed for: total inflammatory cell count in the BAL fluid (FIG. 15); cytokine production in the mediastinal lymph nodes (FIG. 16); serum immunoglobulin production (FIG. 17); indicators of goblet cell metaplasia (FIG. 18); and bronchial hyperresponsiveness (FIG. 19). Experimental protocols were performed as described in Example 3 above.

Figure 15:
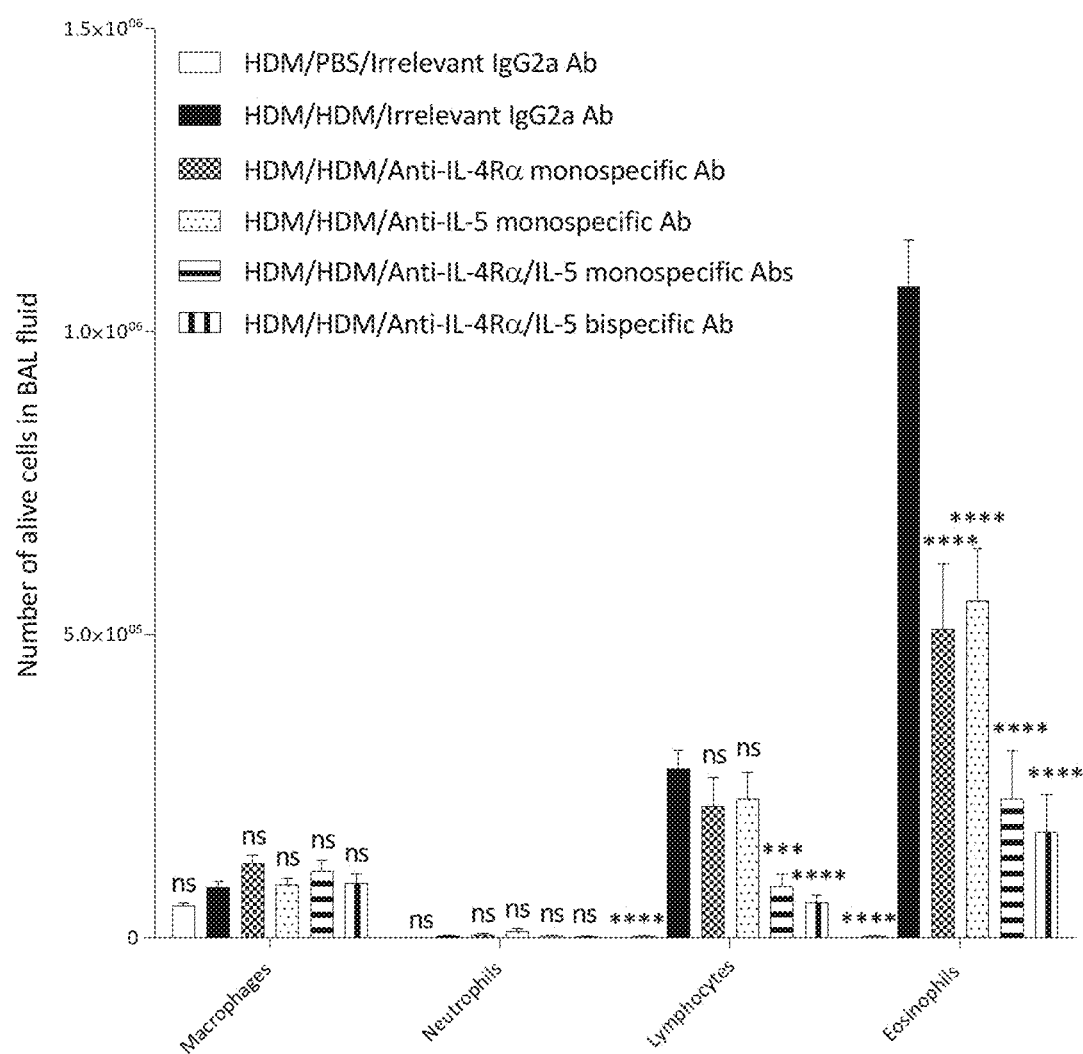
FIG. 15 shows BAL differential cell counts of HDM-treated mice that received the IL-4Rα monospecific Ab, IL-5 monospecific Ab, combined IL-4Rα/IL-5 monospecific Abs, IL-4Rα/IL-5 bispecific Ab, or an irrelevant IgG2a Ab, as analysed by FACS. HDM challenge in sensitized mice increased the number of eosinophils in the BAL fluid. This increase in eosinophil number was significantly decreased after the injections in mice receiving the combination of both monospecific IL-4Rα and IL-5 Abs (75 μg+75 μg), and in mice receiving the IL-4Rα/IL-5 bispecific Abs. The combination of both monospecific Abs and the bispecific antibody result in a significant decrease in the number of eosinophils as compared to the HDM-treated mice that received the control IgG2a Ab. P values reflect the one-way ANOVA test, ns: not significant, *P≤0.001, **P≤0.0001 versus an irrelevant IgG2 Ab.

A. IL-4Rα/IL-5 Bispecific Ab Injected in a Murine HDM Model of Asthma, Decreases Eosinophilia:

As shown in FIG. 15, HDM challenge in sensitized mice increased the number of eosinophils in the BAL fluid. This increase in eosinophil number was significantly decreased in mice receiving the combination of IL-4Rα and IL-5 Abs (75 μg+75 μg). Notably, the bispecific IL-4Rα/IL-5 Ab (150 μg) was as effective as the combination of both IL-4Rα and IL-5 mAbs in reducing airway eosinophilia and lymphocytosis induced by allergen challenge.

B. IL-4Rα/IL-5 Bispecific Ab Reduces Cytokine Production:

As shown in FIG. 16, the HDM-induced MLN type 2 cytokine (IL-5 and IL-13) levels were significantly decreased after treatment with the combination of IL-4Rα and IL-5 Abs and the bispecific Ab.

Figure 17:
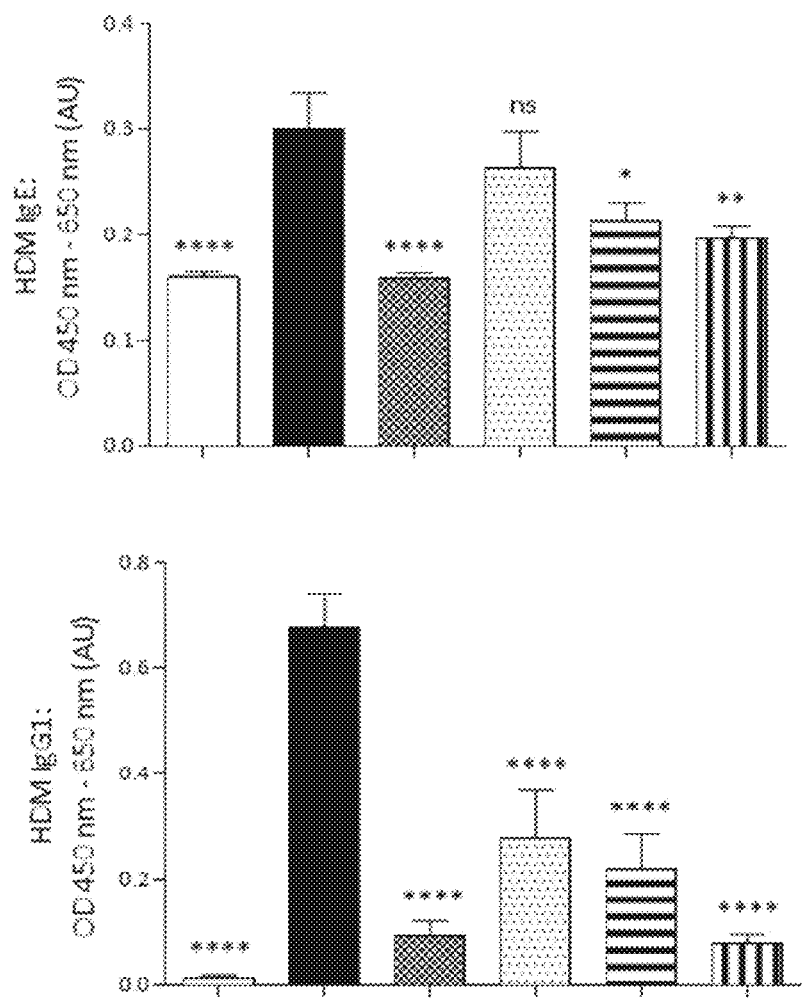
FIG. 17 shows serum levels of HDM-specific IgE and IgG1, after treatment with IL-4Rα monospecific Ab, IL-5 monospecific Ab, combined IL-4Rα/IL-5 monospecific Abs, IL-4Rα/IL-5 bispecific Ab, or an irrelevant IgG2a Ab, determined by ELISA. P values reflect the one-way ANOVA test, ns: not significant, *P≤0.05, P≤0.01, *P≤0.001 versus an irrelevant IgG2 Ab.

C. IL-4Rα/IL-5 Bispecific Ab Reduces the Production of HDM-Specific IgE and IgG1:

As shown in FIG. 17, the HDM-specific IgE and IgG1 were also significantly decreased after treatment with the combination of IL-4Rα and IL-5 Abs and the bispecific Ab.

D. IL-4Rα/IL-5 Bispecific Ab Reduces the Expression of Muc5AC and Agr2:

To test and to compare the effects of the bispecific Ab on goblet cell metaplasia (GCM), the mRNA expression levels of Muc5ac and Agr2 were measured in lung tissue. The increased expression of Muc5ac and Agr2 observed in HDM sensitized and challenged mice was significantly reduced by the combination of IL-4Rα and IL-5 Abs and the bispecific Ab (FIG. 18), whereas the individual IL-4Rα and IL-5 Ab treatments had no significant effect.

E. IL-4Rα/IL-5 Bispecific Ab Reduces Lung Resistance:

Treatment with the combination of IL-4Rα and IL-5 Abs and treatment with the bispecific Ab protected the lungs equally well from HDM-induced BHR, as assessed by methacholine-induced bronchoconstriction. As shown in FIG. 19, mice treated with the combination of IL-4Rα and IL-5 mAbs and the bispecific Ab were completely protected from developing BHR. In contrast, the resistance observed in HDM sensitized and challenged mice treated with the individual IL-4Rα and IL-5 antibodies was not reduced significantly. This evidences the synergistic effect of the combination therapy (either in the format of co-administration of individual IL-4Rα and IL-5 antibodies or as a bispecific antibody) in treating a fundamental aspect of chronic airway disease, particularly asthma.

Altogether these results showed that a bispecific Ab targeting simultaneously IL-4Rα and IL-5 is effective in reducing all salient asthma features when administered during the challenge phase in a HDM driven model of asthma.

Example 6: In Vitro Characterisation of IL-4Rα and IL-5 mAbs

The human IL-4Rα and IL-5 mAbs (h4RMP5D1, h4RMP3B2, 4RMP3D6 and h5MP90A9, h5MP90D9, h5MP92B4, h5MP90C8, h5MP90E7, h5MP90G7) were tested for their ability to bind to their respective targets in vitro and to inhibit cellular effects mediated by IL-4Rα and IL-5 signalling as described in Example 2. The proliferation assay was modified so as to use hIL-4 and hIL-5 at concentrations giving suboptimal proliferation of the cells. The results are shown in the tables below.

TABLE 15

| Target | Clone | Affinity against human IL-5 KD (M) | IC50 (pM) hIL-5 (0.25 ng/mL) |
|---|---|---|---|
| Human IL-5 | 5MP90A9 | 8.35E−11 | 4.99 |
| | 5MP90D9 | 2.64E−11 | 6.84 |
| | 5MP90C8 | 1.33E−10 | 6.93 |
| | 5MP90E7 | 1.29E−10 | 8.84 |
| | 5MP90G7 | 1.13E−10 | 1.61 |
| | 5MP26H7 | 7.49E−11 | 37.52 |

TABLE 16

| Target | Clone | Affinity against human IL-4Rα KD (M) | IC50 (nM) hIL-4 (1.5 ng/mL) |
|---|---|---|---|
| Human IL-4Rα | 4RMP5D1 | 4.42E−11 | 0.2 |
| | 4RMP3B2 | 8.18E−11 | 0.4 |
| | 4RMP3D6 | 5.51E−11 | 0.6 |

Figure 20:
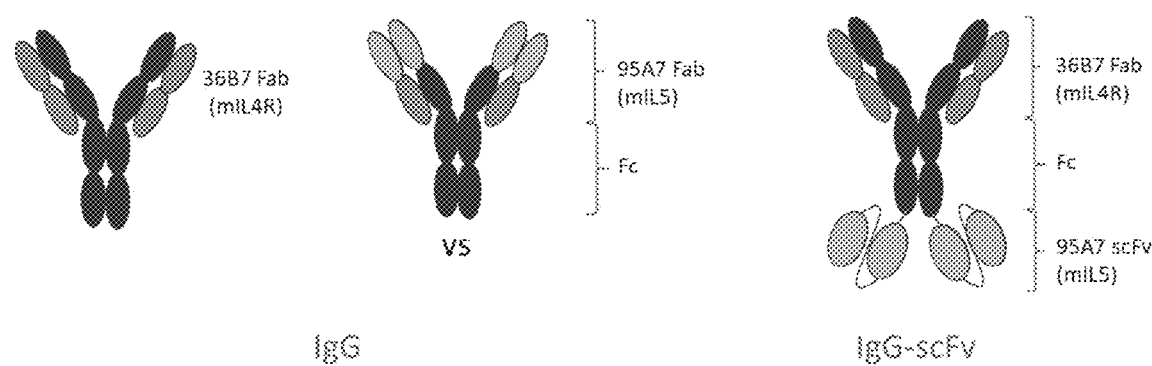
FIG. 20 shows the structure of a IL-4Rα/IL-5 bispecific antibody having an IL-4Rα IgG linked to two IL-5 scFv fragments. The Fab arms of the IL-4Rα IgG have the VH and VL domain sequences of antibody 3667 (see SEQ ID NOs: 45 and 46, respectively). The VH and VL domains of the IL-5 scFv fragments derive from antibody 95G7 and have the sequences represented by SEQ ID NOs: 76 and 79, respectively.

Example 7: Generation and In Vitro Characterisation of a Second IL-4Rα/IL-5 Bispecific Antibody A second IL-4Rα/IL-5 bispecific antibody was generated using the sequences of the 4RMP36B7 IL-4Rα antibody and the 5MP95G7 IL-5 antibody. The VH-VL domains of the 5MP95G7 antibody were produced as single chain Fv (scFv) fragments with either a 15 or 20 amino acid linker (15GS= $(GGGS)_3$ or 20GS=$(GGGS)_4$) and two of these scFv fragments were attached to the C-terminus of the Fc domain of the 4RMP36B7 IgG antibody via a $(GGGS)_3$ connector (15GS). Furthermore, to stabilize the scFv, two mutations were introduced, one in the VH95G7 (G44C) and one in the VL97G7 (G100C). A schematic of this second IL-4Rα/IL-5 bispecific antibody is shown in FIG. 20.

This second IL-4Rα/IL-5 bispecific antibody was tested for its ability to inhibit IL-5-induced proliferation of TF-1 cells. The bispecific antibody was tested alongside the IL-4Rα antibody 36B7hIgG1 and the IL-5 antibodies 95G7hIgG1 and 95G7mIgG2a.

The assay was performed essentially as described above in Example 2. Briefly, a fixed concentration of mIL-5 (R&D Systems) was pre-incubated with a 5-fold serial dilution of antibodies (starting from 100 nM) and was added to 500.000 human TF-1 cells (erythroblasts, ATCC® CRL-2003™; final concentration of mouse IL-5 (R&D Systems) 0.25 ng/mL) and the cells were incubated for 48 h at 37° C. in 5% $CO_2$. 20 µl of CellTiter 96® AQueous One Solution Reagent (Promega) was added and the cells were incubated for 3 hours at 37° C. The absorbance was measured at A490 vs A655.

Figure 21:
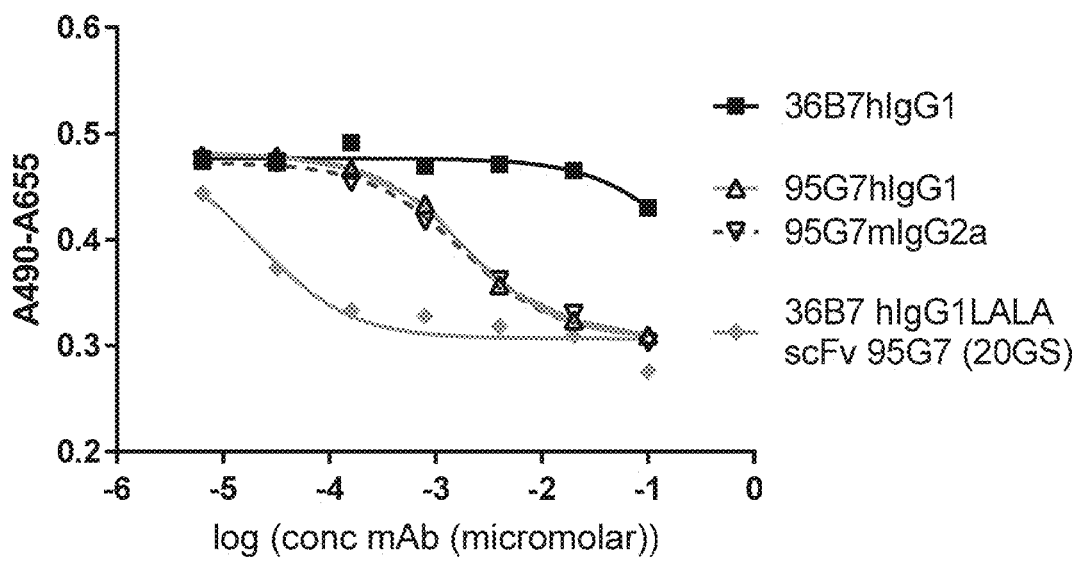
FIG. 21 shows the neutralizing activity of the IL-4Rα/IL-5 bispecific antibody as assessed in an in vitro cellular assay of IL-5 induced proliferation of TF-1 cells. The bispecific antibody of FIG. 20 was tested alongside an IL-4Rα mAb (3667) and two IL-5 mAbs (95G7hIgG1 and 95A7mIgG2a).

The results are shown in FIG. 21 and Table 17 below.

TABLE 17

| mAb or bsAb | EC50 (nM) |
|---|---|
| 36B7hIgG1 | no effect |
| 95G7hIgG1 | 1.86 |
| 95G7mIgG2a-N297A | 1.75 |
| 36B7 hIgG1LALA scFv 95G7 (20GS) | 0.02 |

As expected, the IL-4Rα antibody had no effect on the proliferation of the TF-1 cells whereas the 95A7 antibody configured either as a human IgG1 or a murine IgG2a antibody was able to inhibit the IL-5 induced proliferation of the cells. Interestingly, the IL-4Rα/IL-5 bispecific antibody was able to inhibit the IL-5 induced proliferation of the cells with much higher potency than the 95A7 IgG antibodies—a 100-fold improvement in potency. In other words, the VH-VL domains of the 95A7 antibody configured as scFv fragments at the C-terminus of the Fc region of the IL-4Rα IgG antibody were much more potent than when configured as Fab arms in native IgG structures.

Example 8: In Vivo Characterisation of the Anti-Mouse IL-4Rα/IL-5 IgG-scFv Bispecific Antibody in a Murine HDM Model The IL-4Rα/IL-5 bispecific antibody described in Example 7 above was tested in the murine HDM model described in Examples 3 and 5 above. The experimental protocol is as shown in FIG. 22. Mice were subjected to the HDM sensitization and challenge protocol and treated with the Abs during the challenge phase only.

The in vivo activity of the IL-4Rα/IL-5 bispecific Ab (4Rsc5) was compared with a combination of the anti-mIL-4Rα (36B7) and anti-mIL5 (95G7). Each injection was either 150 µg or 75 µg of the bispecific (4Rsc5) or of the combination (in that case 75 µg of each antibody to reach 150 µg total or 36.75 µg of each antibody to reach the dose per injection of 75 µg).

Figure 24:
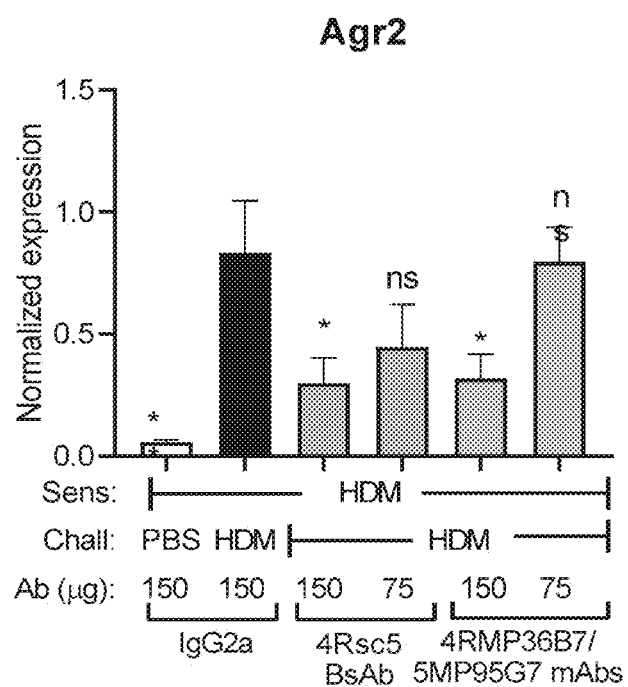
FIG. 24 shows lung mRNA expression levels of MucSac, Agr2, and Spdef determined by qRT-PCR. The mRNA expression levels of these two genes were induced by HDM challenge in mice as compared with PBS challenge.

Mice treated according to this protocol were subsequently assessed for: total eosinophils and lymphocytes cell count in the BAL fluid (FIG. 23) and expression of muc5a, spdef and agr2 (FIG. 24). Experimental protocols were performed as described in Example 3 above.

Example 9: Engineering Human IL-4Rα Antibodies

The human IL-4Rα mAb—4RMP3D6—was engineered so as be cross-reactive with Cyno/Rhesus IL-4Rα. Variants of 4RMP3D6 were generated by random mutatagenesis using the error prone PCR approach. For this, the GeneMorphII EZClone domain mutagenesis kit (Agilent) was used. In accordance with the supplier's recommendation, mutations were introduced into the VH and VK of 4RMP3D6. The mutated VH (VHm*) and VK (VKm*) were further cloned into a phagemid vector (PCB13) containing the CH1 and CK constant domains to generate mutated Fab libraries.

Sequencing demonstrated that the procedure led to around 3 to 5 amino acid substitutions in each V domain (VH and VK). Several libraries (VHmWKwt, VHwt/V/Km* and VHm*/V/Km*) were made and used for several rounds of phage display selections on cynomolgus recombinant IL-4Rα (agroBioscience cat#ILR-052H8). After 3 rounds of selection, clones were selected (from round 2 and 3), and Fab was produced from the periplasmic extracts and tested by SPR. For the SPR, a Biacore 3000 was used in combination with CM5 chip coated with either human IL-4Rα or cyno IL-4Rα. The binding (R0) and dissociation (kd, s$^{-1}$) were recorded as shown in Table 18 below.

TABLE 18

|  | cyno/rhesus IL-4Rα | | human IL-4Rα | |
| --- | --- | --- | --- | --- |
|  | kd (s$^{-1}$) | R0 | kd (s$^{-1}$) | R0 |
| 152A07 | 1.7E−03 | 94 | 6.9E−04 | 58 |
| 152B10 | 2.6E−03 | 170 | 1.2E−03 | 110 |
| 153A11 | 3.3E−04 | 146 | 2.0E−03 | 68 |
| 153E11 | 1.4E−03 | 78 | 4.3E−04 | 56 |
| 150A09 | 2.0E−03 | 80 | 8.4E−04 | 53 |
| 151A03 | 2.8E−03 | 246 | 3.0E−03 | 129 |
| 3D6wt | 1.7E−03 | 26 | 5.3E−04 | 204 |

The CDR, VH and VL sequences of the selected antibodies are shown in Tables 19-21 below.

TABLE 19

Heavy chain CDR sequences of human IL-4Rα mAbs with cross-reactivity to Cyno/Rhesus IL-4Rα

| Ab | CDR1 | SEQ ID NO: | CDR2 | SEQ ID NO: | CDR3 | SEQ ID NO: |
| --- | --- | --- | --- | --- | --- | --- |
| h4R3D6 | SYSLT | 7 | TIKARGGTTLYADSVKD | 8 | PLYNNFAGDFGS | 9 |
| VH152A07 | SYSLT | 7 | TIKARGGTTLYADSVKD | 8 | PLYSNLAGDLGS | 91 |
| VH153A11 | SYSLT | 7 | TIKARGGTTLYADSVKD | 8 | PLYSNLAGDFGS | 92 |
| VH152B10 | SYSLT | 7 | TIKARGGTTLYADSVKD | 8 | PLYNNLAGDFGS | 93 |
| VH150A09 | SYSLT | 7 | TIKARGGTTLYADSVKD | 8 | PLYSNFAGDFGS | 94 |
| VH153E11 | SYSLT | 7 | TIKARGGTTLYADSVKD | 8 | PLYNNFAGHFGS | 95 |

TABLE 20

Light chain CDR sequences of human IL-4Rα mAbs with cross-reactivity to Cyno/Rhesus IL-4Rα

| Ab | CDR1 | SEQ ID NO: | CDR2 | SEQ ID NO: | CDR3 | SEQ ID NO: |
| --- | --- | --- | --- | --- | --- | --- |
| h4R3D6 | QASQSISSYLA | 16 | GGSRLQT | 17 | LQDYSWPLT | 18 |
| VH152A07 | QASQSISSYLA | 16 | GGSRLQT | 17 | LQDYSWPLT | 18 |
| VH153A11 | QASQSISSYLA | 16 | GGSRLQT | 17 | LQVYSWPLT | 97 |
| VH152B10 | QASQSISSYLA | 16 | GGSRLQA | 96 | QQDYSWPLT | 98 |
| VH150A09 | QASQSISSYLA | 16 | GGSRLQT | 17 | QQDYSWPLT | 98 |
| VH153E11 | QASQSISSYLA | 16 | GGSRLQT | 17 | QQDYSWPLT | 98 |

TABLE 21

VH and VL sequences of human IL-4Rα mAbs with cross-reactivity to Cyno/Rhesus IL-4Rα

| Fab clone | VH | SEQ ID NO. | VL | SEQ ID NO. |
|---|---|---|---|---|
| h4R3D6 | QVQLQESGGGLVQPGGSLRLSCAASGFTFS SYSLTWVRQAPGKGLEWVSTIKARGGTTLY ADSVKDRFTISRDNAKNTLYLLMNSLKPEDT AVYYCAKPLYNNFAGDFGSWGQGTTVTVSS | 23 | DIQMTQSPSSLSASLGDRVTITCQASQSISSYLAWYQQ KPGQAPKLLIYGGSRLQTGVPSRFSGSGSGTSFTLTIS GLETEDLATYYCLQDYSWPLTFGQGTKVELK | 24 |
| VH152A07 | QVQLQESGGGLVQPGGSLRLSCAASGFTFS SYSLTWVRQAPGKGLEWVSTIKARGGTTLY ADSVKDRFTISRDNAKNTLYLLMNSLKPEDT AVYYCAKPLYSNLAGDLGSWGQGTTVTVSS | 99 | DIQMTQSPSSLSASLGDRVTITCQASQSISSYLAWYQQ KPGQAPKLLIYGGSRLQTGVPSRFSGSGSGTSFTLTIS GLETEDLATYYCLQDYSWPLTFGQGTKLEIK | 100 |
| VH153A11 | QVQLQESGGGLVQPGGSLRLSCAASGFTFS SYSLTWVRQAPGKGLEWVSTIKARGGTTLY ADSVKDRFTISRDNAKNTLYLQMNSLKPEDT AVYYCAKPLYSNLAGDFGSWGQGTTVTVSS | 101 | DIQMTQSPSSLSASLGDRVTITCQASQSISSYLAWYQQ KSGQAPKLLIYGGSRLQTGVPSRFSGSGSGTSFTLTIS GLETEDLATYYCLQVYSWPLTFGQGTKLEIK | 102 |
| VH152B10 | QVQLQESGGGLVQPGGSLRLSCAASGFTFS SYSLTWVRQAPGKGLEWVSTIKARGGTTLY ADSVKDRFTISRDNAKNTLYLLVNSLKPEDTA VYYCAKPLYNNLAGDFGSWGQGTTVTVSS | 103 | DIQMTQSPSSLSASLGDRVTITCQASQSISSYLAWYQQ KPGQAPKWYGGSRLQAGVPSRFSGSGSGTSFILTIG GLETEDLATYYCQQDYSWPLTFGQGTKLEIK | 104 |
| VH150A09 | QVQLQESGGGLVQPGGSLRLSCAASGFTFS SYSLTWVRQAPGKGLEWVSTIKARGGTTLY ADSVKDRFTISRDNAKNTLYLLMNSLKPEDT AVYYCVKPLYSNFAGDFGSWGQGTTVTVSS | 105 | DIQMTQSPSSLSASLGDRVTITCQASQSISSYLAWYQQ KPGQAPRLLIYGGSRLQTGVPSRFSGSGSGTSFTLTIS GLETEDLATYYCQQDYSWPLTFGQGTKLEIK | 106 |
| VH153E11 | QVQLQESGGGLVQPGGSLRLSCAASGFTFS SYSLTWVRQAPGKGLEWVSTIKARGGTTLY ADSVKDRFTISRDNAKNTLYLLMNSLKPEDT AVYYCAKPLYNNFAGHFGSWGQGTTVTVSS | 107 | DIQMTQSPSSLSASLGDRVTITCQASQSISSYLAWYQQ KPGQAPKLLIYGGSRLQTGVPSRFSGSGSGTSFTLTIS GLETEDLATYYCQQDYSWPLTFGQGTKLEIK | 108 |

The invention claimed is:

1. A multispecific antibody comprising:
  (i) an antagonist antibody to human IL-5 comprising a heavy chain variable region (VH) comprising the HC-CDR1, HC-CDR2, and HC-CDR3 amino acid sequences of the VH of SEQ ID NO: 63; and a light chain variable region (VL) comprising the LC-CDR1, LC-CDR2 and LC-CDR3 amino acid sequences of the VL of SEQ ID NO: 65; and
  (ii) an antagonist antibody to human IL-4R comprising a VH comprising the HC-CDR1, HC-CDR2, and HC-CDR3 amino acid sequences of the VH of SEQ ID NO:

23 or 107; and a VL comprising the LC-CDR1, LC-CDR2 and LC-CDR3 amino acid sequences of the VL of SEQ ID NO: 24 or 108.

2. The multispecific antibody of claim 1, wherein the antibody to human IL-4R comprises the HC-CDR1, HC-CDR2, and HC-CDR3 amino acid sequences of the VH of SEQ ID NO: 107; and the LC-CDR1, LC-CDR2 and LC-CDR3 amino acid sequences of the VL of SEQ ID NO: 108.

3. The multispecific antibody of claim 1, wherein the HC-CDR1, HC-CDR2, HC-CDR3, LC-CDR1, LC-CDR2, and LC-CDR3 of the antibody to human IL-4R comprise the amino acid sequences of SEQ ID NOs: 7, 8, 9, 16, 17, and 18, respectively; or SEQ ID NOs: 7, 8, 95, 16, 17, and 98, respectively.

4. The multispecific antibody of claim 1, wherein the HC-CDR1, HC-CDR2, HC-CDR3, LC-CDR1, LC-CDR2, and LC-CDR3 of the antibody to human IL-4R comprise the amino acid sequences of SEQ ID NOs: 7, 8, 95, 16, 17, and 98, respectively.

5. The multispecific antibody of claim 1, wherein the VH and VL of the antibody to human IL-4R comprise amino acid sequences at least 90% identical to the amino acid sequences of SEQ ID NOs: 23 and 24, respectively; or SEQ ID NOs: 107 and 108, respectively.

6. The multispecific antibody of claim 5, wherein the VH and VL of the antibody to human IL-4R comprise the amino acid sequences of SEQ ID NOs: 23 and 24, respectively; or SEQ ID NOs: 107 and 108, respectively.

7. The multispecific antibody of claim 1, wherein the VH and VL of the antibody to human IL-4R comprise amino acid sequences at least 90% identical to the amino acid sequences of SEQ ID NOs: 107 and 108, respectively.

8. The multispecific antibody of claim 1, wherein the VH and VL of the antibody to human IL-4R comprise the amino acid sequences of SEQ ID NOs: 107 and 108, respectively.

9. The multispecific antibody of claim 1, wherein the HC-CDR1, HC-CDR2, HC-CDR3, LC-CDR1, LC-CDR2, and LC-CDR3 of the antibody to human IL-5 comprise the amino acid sequences of SEQ ID NOs: 49, 50, 51, 55, 56, and 57, respectively.

10. The multispecific antibody of claim 9, wherein the HC-CDR1, HC-CDR2, HC-CDR3, LC-CDR1, LC-CDR2, and LC-CDR3 of the antibody to human IL-4R comprise the amino acid sequences of SEQ ID NOs: 7, 8, 95, 16, 17, and 98, respectively.

11. The multispecific antibody of claim 1, wherein the VH and VL of the antibody to human IL-5 comprise amino acid sequences at least 90% identical to the amino acid sequences of SEQ ID NOs: 63 and 65, respectively.

12. The multispecific antibody of claim 11, wherein the VH and VL of the antibody to human IL-4R comprise amino acid sequences at least 90% identical to the amino acid sequences of SEQ ID NOs: 107 and 108, respectively.

13. The multispecific antibody of claim 11, wherein the VH and VL of the antibody to human IL-5 comprise the amino acid sequences of SEQ ID NOs: 63 and 65, respectively.

14. The multispecific antibody of claim 13, wherein the VH and VL of the antibody to human IL-4R comprise the amino acid sequences of SEQ ID NOs: 107 and 108, respectively.

15. The multispecific antibody of claim 1, wherein the HC-CDR1, HC-CDR2, HC-CDR3, LC-CDR1, LC-CDR2, and LC-CDR3 of the antibody to human IL-5 comprise the amino acid sequences of SEQ ID NOs: 49, 50, 51, 55, 56, and 57, respectively; and wherein the HC-CDR1, HC-CDR2, HC-CDR3, LC-CDR1, LC-CDR2, and LC-CDR3 of the antibody to human IL-4R comprise the amino acid sequences of SEQ ID NOs: 7, 8, 9, 16, 17, and 18, respectively; or SEQ ID NOs: 7, 8, 95, 16, 17, and 98, respectively.

16. The multispecific antibody of claim 1, wherein the VH and VL of the antibody to human IL-5 comprise amino acid sequences at least 90% identical to the amino acid sequences of SEQ ID NOs: 63 and 65, respectively; and wherein the VH and VL of the antibody to human IL-4R comprise amino acid sequences at least 90% identical to the amino acid sequences of SEQ ID NOs: 23 and 24, respectively; or SEQ ID NOs: 107 and 108, respectively.

17. The multispecific antibody of claim 1, wherein the VH and VL of the antibody to human IL-5 comprise the amino acid sequences of SEQ ID NOs: 63 and 65, respectively, and wherein the VH and VL of the antibody to human IL-4R comprise the amino acid sequences of SEQ ID NOs: 23 and 24, respectively; or SEQ ID NOs: 107 and 108, respectively.

18. The multispecific antibody of claim 1, wherein the multispecific antibody exhibits lower antigen-binding activity at acidic pH than at neutral pH.

19. The multispecific antibody of claim 18, wherein the ratio of antigen-binding activity at acidic pH and at neutral pH is at least 2 as measured by KD(at acidic pH)/KD(at neutral pH).

20. The multispecific antibody of claim 1, wherein the multispecific antibody is a bispecific antibody.

* * * * *

SEQUENCE LISTING

<160> NUMBER OF SEQ ID NOS: 108

<210> SEQ ID NO 1
<211> LENGTH: 5
<212> TYPE: PRT
<213> ORGANISM: Artificial sequence
<220> FEATURE:
<223> OTHER INFORMATION: Synthetic peptide

<400> SEQUENCE: 1

Ser Tyr Ile Met Ser
1               5

<210> SEQ ID NO 2
<211> LENGTH: 17
<212> TYPE: PRT
<213> ORGANISM: Artificial sequence
<220> FEATURE:
<223> OTHER INFORMATION: Synthetic peptide

<400> SEQUENCE: 2

Gly Ile Ser Ser Gly Gly Gly Ile Thr Ala Tyr Ala Asp Ser Val Lys
1               5                   10                  15

Gly

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 3

Gly Leu Leu Arg Val Glu Gly Tyr
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Ser Tyr Asp Met Thr
1               5

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Ala Ile Asn Ser Gly Gly Gly Ser Thr Asn Tyr Ala Asp Ser Val Lys
1               5                   10                  15

Gly

<210> SEQ ID NO 6
<211> LENGTH: 16
<212> TYPE: PRT
<213> ORGANISM: Artificial sequence
<220> FEATURE:
<223> OTHER INFORMATION: Synthetic peptide

<400> SEQUENCE: 6

Ala Leu Arg Thr Val Val His Asp Arg Arg Leu Phe Tyr Ile Asp Ser
1               5                   10                  15

<210> SEQ ID NO 7
<211> LENGTH: 5
<212> TYPE: PRT
<213> ORGANISM: Artificial sequence
<220> FEATURE:
<223> OTHER INFORMATION: Synthetic peptide

<400> SEQUENCE: 7

Ser Tyr Ser Leu Thr
1               5

<210> SEQ ID NO 8
<211> LENGTH: 17
<212> TYPE: PRT
<213> ORGANISM: Artificial sequence
<220> FEATURE:
<223> OTHER INFORMATION: Synthetic peptide

<400> SEQUENCE: 8

Thr Ile Lys Ala Arg Gly Gly Thr Thr Leu Tyr Ala Asp Ser Val Lys
1               5                   10                  15

Asp

<210> SEQ ID NO 9
<211> LENGTH: 12
<212> TYPE: PRT
<213> ORGANISM: Artificial sequence
```

<220> FEATURE:
<223> OTHER INFORMATION: Synthetic peptide

<400> SEQUENCE: 9

Pro Leu Tyr Asn Asn Phe Ala Gly Asp Phe Gly Ser
1               5                   10

<210> SEQ ID NO 10
<211> LENGTH: 14
<212> TYPE: PRT
<213> ORGANISM: Artificial sequence
<220> FEATURE:
<223> OTHER INFORMATION: Synthetic peptide

<400> SEQUENCE: 10

Gly Leu Ser Ser Gly Ser Val Thr Ser Ser Asn Tyr Pro Gly
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic peptide

<400> SEQUENCE: 11

Ala Thr Ala Ser Arg His Ser
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic peptide

<400> SEQUENCE: 12

Ala Leu His Lys Gly Thr Tyr Val
1               5

<210> SEQ ID NO 13
<211> LENGTH: 11
<212> TYPE: PRT
<213> ORGANISM: Artificial sequence
<220> FEATURE:
<223> OTHER INFORMATION: Synthetic peptide

<400> SEQUENCE: 13

Gly Gly Asn Asn Ile Gly Ser Lys Ser Ala Gln
1               5                   10

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Ala Asp Ser Arg Arg Pro Ser
1               5

<210> SEQ ID NO 15
<211> LENGTH: 9
<212> TYPE: PRT
<213> ORGANISM: Artificial sequence
<220> FEATURE:

```
<223> OTHER INFORMATION: Synthetic peptide

<400> SEQUENCE: 15

Gln Val Trp Asp Thr Ser Ala Val Val
1               5

<210> SEQ ID NO 16
<211> LENGTH: 11
<212> TYPE: PRT
<213> ORGANISM: Artificial sequence
<220> FEATURE:
<223> OTHER INFORMATION: Synthetic peptide

<400> SEQUENCE: 16

Gln Ala Ser Gln Ser Ile Ser Ser Tyr Leu Ala
1               5                   10

<210> SEQ ID NO 17
<211> LENGTH: 7
<212> TYPE: PRT
<213> ORGANISM: Artificial sequence
<220> FEATURE:
<223> OTHER INFORMATION: Synthetic peptide

<400> SEQUENCE: 17

Gly Gly Ser Arg Leu Gln Thr
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Leu Gln Asp Tyr Ser Trp Pro Leu Thr
1               5

<210> SEQ ID NO 19
<211> LENGTH: 117
<212> TYPE: PRT
<213> ORGANISM: Artificial sequence
<220> FEATURE:
<223> OTHER INFORMATION: Synthetic peptide

<400> SEQUENCE: 19

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Ser Trp Val Arg Gln Ala Pro Gly Lys Gly Leu Glu Trp Val
        35                  40                  45

Ser Gly Ile Ser Ser Gly Gly Gly Ile Thr Ala Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Asp Asp Thr Ala Val Tyr Tyr Cys
                85                  90                  95

Val Ala Gly Leu Leu Arg Val Glu Gly Tyr Trp Gly Gln Gly Thr Gln
            100                 105                 110

Val Thr Val Ser Ser
            115
```

<210> SEQ ID NO 20
<211> LENGTH: 108
<212> TYPE: PRT
<213> ORGANISM: Artificial sequence
<220> FEATURE:
<223> OTHER INFORMATION: Synthetic peptide

<400> SEQUENCE: 20

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Thr Pro Gly Gln Ala Pro Arg Ser
        35                  40                  45

Leu Ile Tyr Ala Thr Ala Ser Arg His Ser Gly Val Pro Ser Arg Tyr
    50                  55                  60

Ser Gly Ser Ile Ser Gly Asn Lys Ala Thr Leu Thr Ile Thr Gly Ala
65                  70                  75                  80

Glu Pro Glu Asp Glu Ala Asp Tyr Tyr Cys Ala Leu His Lys Gly Thr
                85                  90                  95

Tyr Val Phe Gly Gly Gly Thr Lys Leu Thr Val Leu
            100                 105

<210> SEQ ID NO 21
<211> LENGTH: 125
<212> TYPE: PRT
<213> ORGANISM: Artificial sequence
<220> FEATURE:
<223> OTHER INFORMATION: Synthetic peptide

<400> SEQUENCE: 21

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Thr Trp Val Arg Gln Ala Pro Gly Lys Gly Leu Glu Trp Val
        35                  40                  45

Ser Ala Ile Asn Ser Gly Gly Gly Ser Thr Asn Tyr Ala Asp Ser Val
    50                  55                  60

Lys Gly Arg Val Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Phe Cys
                85                  90                  95

Ala Arg Ala Leu Arg Thr Val Val His Asp Arg Arg Leu Phe Tyr Ile
            100                 105                 110

Asp Ser Trp Gly Gln Gly Thr Gln Val Thr Val Ser Ser
        115                 120                 125

<210> SEQ ID NO 22
<211> LENGTH: 106
<212> TYPE: PRT
<213> ORGANISM: Artificial sequence
<220> FEATURE:
<223> OTHER INFORMATION: Synthetic peptide

<400> SEQUENCE: 22

Ser Tyr Glu Leu Thr Gln Ser Pro Ser Val Ser Val Ala Leu Arg Gln
1               5                   10                  15

```
Thr Ala Lys Ile Thr Cys Gly Gly Asn Asn Ile Gly Ser Lys Ser Ala
            20                  25                  30

Gln Trp Tyr Gln Gln Lys Pro Gly Gln Ala Pro Val Leu Val Ile Tyr
            35                  40                  45

Ala Asp Ser Arg Arg Pro Ser Gly Ile Pro Glu Arg Phe Ser Gly Ser
50                      55                  60

Asn Ser Gly Asn Thr Ala Thr Leu Thr Val Ser Gly Ala Gln Ala Glu
65                  70                  75                  80

Asp Glu Ala Asp Tyr Tyr Cys Gln Val Trp Asp Thr Ser Ala Val Val
                85                  90                  95

Phe Gly Gly Gly Thr Arg Leu Thr Val Leu
            100                 105
```

<210> SEQ ID NO 23
<211> LENGTH: 121
<212> TYPE: PRT
<213> ORGANISM: Artificial sequence
<220> FEATURE:
<223> OTHER INFORMATION: Synthetic peptide

<400> SEQUENCE: 23

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Leu Thr Trp Val Arg Gln Ala Pro Gly Lys Gly Leu Glu Trp Val
        35                  40                  45

Ser Thr Ile Lys Ala Arg Gly Gly Thr Thr Leu Tyr Ala Asp Ser Val
50                  55                  60

Lys Asp Arg Phe Thr Ile Ser Arg Asp Asn Ala Lys Asn Thr Leu Tyr
65                  70                  75                  80

Leu Leu Met Asn Ser Leu Lys Pro Glu Asp Thr Ala Val Tyr Tyr Cys
                85                  90                  95

Ala Lys Pro Leu Tyr Asn Asn Phe Ala Gly Asp Phe Gly Ser Trp Gly
            100                 105                 110

Gln Gly Thr Thr Val Thr Val Ser Ser
        115                 120
```

<210> SEQ ID NO 24
<211> LENGTH: 107
<212> TYPE: PRT
<213> ORGANISM: Artificial sequence
<220> FEATURE:
<223> OTHER INFORMATION: Synthetic peptide

<400> SEQUENCE: 24

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Gly Gly Ser Arg Leu Gln Ser Gly Val Pro Ser Arg Phe Ser Gly
50                  55                  60

Ser Gly Ser Gly Thr Ser Phe Thr Leu Thr Ile Ser Gly Leu Glu Thr
65                  70                  75                  80

Glu Asp Leu Ala Thr Tyr Tyr Cys Leu Gln Asp Tyr Ser Trp Pro Leu
                85                  90                  95
```

Thr Phe Gly Gln Gly Thr Lys Val Glu Leu Lys
            100                 105

<210> SEQ ID NO 25
<211> LENGTH: 5
<212> TYPE: PRT
<213> ORGANISM: Artificial sequence
<220> FEATURE:
<223> OTHER INFORMATION: Synthetic peptide

<400> SEQUENCE: 25

Asp Tyr Ala Met Ser
1               5

<210> SEQ ID NO 26
<211> LENGTH: 17
<212> TYPE: PRT
<213> ORGANISM: Artificial sequence
<220> FEATURE:
<223> OTHER INFORMATION: Synthetic peptide

<400> SEQUENCE: 26

Ile Ile Ser Trp Asn Gly Glu Ile Thr His Tyr Ala Glu Ser Met Lys
1               5                   10                  15

Gly

<210> SEQ ID NO 27
<211> LENGTH: 11
<212> TYPE: PRT
<213> ORGANISM: Artificial sequence
<220> FEATURE:
<223> OTHER INFORMATION: Synthetic peptide

<400> SEQUENCE: 27

Asn His Tyr Thr Leu Thr Trp Gly Tyr Asp Tyr
1               5                   10

<210> SEQ ID NO 28
<211> LENGTH: 5
<212> TYPE: PRT
<213> ORGANISM: Artificial sequence
<220> FEATURE:
<223> OTHER INFORMATION: Synthetic peptide

<400> SEQUENCE: 28

Ser Tyr Tyr Met Ala
1               5

<210> SEQ ID NO 29
<211> LENGTH: 17
<212> TYPE: PRT
<213> ORGANISM: Artificial sequence
<220> FEATURE:
<223> OTHER INFORMATION: Synthetic peptide

<400> SEQUENCE: 29

His Ile His Ala Gly Gly Ser Leu Thr Gln Tyr Ala Asp Ser Val Lys
1               5                   10                  15

Gly

<210> SEQ ID NO 30
<211> LENGTH: 10
<212> TYPE: PRT
<213> ORGANISM: Artificial sequence
<220> FEATURE:

<223> OTHER INFORMATION: Synthetic peptide

<400> SEQUENCE: 30

Ile Tyr Gly Asp Ala Thr Ser Tyr Asp Tyr
1               5                   10

<210> SEQ ID NO 31
<211> LENGTH: 5
<212> TYPE: PRT
<213> ORGANISM: Artificial sequence
<220> FEATURE:
<223> OTHER INFORMATION: Synthetic peptide

<400> SEQUENCE: 31

Ser Tyr Ala Met Asn
1               5

<210> SEQ ID NO 32
<211> LENGTH: 16
<212> TYPE: PRT
<213> ORGANISM: Artificial sequence
<220> FEATURE:
<223> OTHER INFORMATION: Synthetic peptide

<400> SEQUENCE: 32

Ala Ile Ser Gly Gly Gly Ser Thr Arg Tyr Ala Asp Ser Val Lys Gly
1               5                   10                  15

<210> SEQ ID NO 33
<211> LENGTH: 16
<212> TYPE: PRT
<213> ORGANISM: Artificial sequence
<220> FEATURE:
<223> OTHER INFORMATION: Synthetic peptide

<400> SEQUENCE: 33

Ser Gly Phe Tyr Ser Asp Tyr Glu Arg Arg Tyr Arg Tyr Leu Glu Val
1               5                   10                  15

<210> SEQ ID NO 34
<211> LENGTH: 11
<212> TYPE: PRT
<213> ORGANISM: Artificial sequence
<220> FEATURE:
<223> OTHER INFORMATION: Synthetic peptide

<400> SEQUENCE: 34

Gln Gly Gly Asn Phe Gly Arg Tyr Tyr Ala Ser
1               5                   10

<210> SEQ ID NO 35
<211> LENGTH: 7
<212> TYPE: PRT
<213> ORGANISM: Artificial sequence
<220> FEATURE:
<223> OTHER INFORMATION: Synthetic peptide

<400> SEQUENCE: 35

Gly Ser Ser Asn Ser Pro Ser
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic peptide

```
<400> SEQUENCE: 36

Gln Val Trp Asp Ser Ser Gly Tyr Lys
1               5

<210> SEQ ID NO 37
<211> LENGTH: 14
<212> TYPE: PRT
<213> ORGANISM: Artificial sequence
<220> FEATURE:
<223> OTHER INFORMATION: Synthetic peptide

<400> SEQUENCE: 37

Ala Gly Thr Ser Ser Asp Ile Gly Gly Tyr Asn Tyr Val Ser
1               5                   10

<210> SEQ ID NO 38
<211> LENGTH: 7
<212> TYPE: PRT
<213> ORGANISM: Artificial sequence
<220> FEATURE:
<223> OTHER INFORMATION: Synthetic peptide

<400> SEQUENCE: 38

Glu Val Asn Lys Arg Ala Ser
1               5

<210> SEQ ID NO 39
<211> LENGTH: 10
<212> TYPE: PRT
<213> ORGANISM: Artificial sequence
<220> FEATURE:
<223> OTHER INFORMATION: Synthetic peptide

<400> SEQUENCE: 39

Ala Ser Tyr Arg Ser Asn Asn Asn Ile Val
1               5                   10

<210> SEQ ID NO 40
<211> LENGTH: 11
<212> TYPE: PRT
<213> ORGANISM: Artificial sequence
<220> FEATURE:
<223> OTHER INFORMATION: Synthetic peptide

<400> SEQUENCE: 40

Gln Ala Ser Gln Ser Ile Arg Pro Glu Ile Ser
1               5                   10

<210> SEQ ID NO 41
<211> LENGTH: 7
<212> TYPE: PRT
<213> ORGANISM: Artificial sequence
<220> FEATURE:
<223> OTHER INFORMATION: Synthetic peptide

<400> SEQUENCE: 41

Gly Ala Ser Arg Leu Gln Thr
1               5

<210> SEQ ID NO 42
<211> LENGTH: 9
<212> TYPE: PRT
<213> ORGANISM: Artificial sequence
<220> FEATURE:
<223> OTHER INFORMATION: Synthetic peptide
```

<400> SEQUENCE: 42

Leu Gln Asp Tyr Ser Trp Pro Tyr Ser
1               5

<210> SEQ ID NO 43
<211> LENGTH: 120
<212> TYPE: PRT
<213> ORGANISM: Artificial sequence
<220> FEATURE:
<223> OTHER INFORMATION: Synthetic peptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Ile Ile Ser Trp Asn Gly Glu Ile Thr His Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Thr Leu Lys Ser Gly Asp Thr Ala Val Tyr Tyr Cys
                85                  90                  95

Ala Lys Asn His Tyr Thr Leu Thr Trp Gly Tyr Asp Tyr Trp Gly Gln
            100                 105                 110

Gly Thr Gln Val Thr Val Ser Ser
        115                 120

<210> SEQ ID NO 44
<211> LENGTH: 106
<212> TYPE: PRT
<213> ORGANISM: Artificial sequence
<220> FEATURE:
<223> OTHER INFORMATION: Synthetic peptide

<400> SEQUENCE: 44

Asn Phe Met Leu Thr Gln Pro Ser Ala Val Ser Val Ser Leu Gly Gln
1               5                   10                  15

Thr Ala Arg Ile Thr Cys Gln Gly Gly Asn Phe Gly Arg Tyr Tyr Ala
            20                  25                  30

Ser Trp Tyr Gln Gln Lys Pro Gly Gln Ala Pro Val Gln Val Ile Tyr
        35                  40                  45

Gly Ser Ser Asn Ser Pro Ser Gly Ile Pro Glu Arg Phe Ser Gly Ser
    50                  55                  60

Ser Ser Gly Asp Thr Ala Thr Leu Thr Ile Ser Gly Ala Gln Ala Glu
65                  70                  75                  80

Asp Glu Ala Asp Tyr Tyr Cys Gln Val Trp Asp Ser Ser Gly Tyr Lys
                85                  90                  95

Phe Gly Gly Gly Thr Thr Leu Thr Val Leu
            100                 105

<210> SEQ ID NO 45
<211> LENGTH: 119
<212> TYPE: PRT
<213> ORGANISM: Artificial sequence
<220> FEATURE:
<223> OTHER INFORMATION: Synthetic peptide

<400> SEQUENCE: 45

```
Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Tyr Met Ala Trp Val Arg Gln Ala Pro Gly Lys Gly Leu Glu Trp Val
        35                  40                  45

Ser His Ile His Ala Gly Gly Ser Leu Thr Gln Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Lys Pro Glu Asp Thr Ala Leu Tyr Tyr Cys
            85                  90                  95

Val Arg Ile Tyr Gly Asp Ala Thr Ser Tyr Asp Tyr Trp Gly Gln Gly
            100                 105                 110

Thr Gln Val Ser Val Ser Ser
            115
```

```
<210> SEQ ID NO 46
<211> LENGTH: 110
<212> TYPE: PRT
<213> ORGANISM: Artificial sequence
<220> FEATURE:
<223> OTHER INFORMATION: Synthetic peptide

<400> SEQUENCE: 46

His Ser Ala Val Thr Gln Pro Pro Ser Val Ser Gly Ser Pro Gly Lys
1               5                   10                  15

Thr Val Thr Ile Ser Cys Ala Gly Thr Ser Ser Asp Ile Gly Gly Tyr
            20                  25                  30

Asn Tyr Val Ser Trp Tyr Gln Gln Phe Pro Gly Thr Ala Pro Lys Leu
        35                  40                  45

Leu Ile Tyr Glu Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Ala Ser Tyr Arg Ser Asn
            85                  90                  95

Asn Asn Ile Val Phe Gly Gly Gly Thr His Leu Thr Val Leu
            100                 105                 110
```

```
<210> SEQ ID NO 47
<211> LENGTH: 124
<212> TYPE: PRT
<213> ORGANISM: Artificial sequence
<220> FEATURE:
<223> OTHER INFORMATION: Synthetic peptide

<400> SEQUENCE: 47

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Gly Gly Ser Thr Arg Tyr Ala Asp Ser Val Lys
    50                  55                  60

Gly Arg Phe Thr Ile Ser Arg Asp Asn Ala Lys Asn Thr Leu Tyr Leu
```

```
                65                  70                  75                  80
Gln Met Asn Ser Leu Lys Pro Glu Asp Thr Ala Val Tyr Tyr Cys Ala
                    85                  90                  95

Lys Ser Gly Phe Tyr Ser Asp Tyr Glu Arg Arg Tyr Arg Tyr Leu Glu
                100                 105                 110

Val Trp Gly Gln Gly Thr Leu Val Thr Val Ser Ser
            115                 120
```

<210> SEQ ID NO 48
<211> LENGTH: 107
<212> TYPE: PRT
<213> ORGANISM: Artificial sequence
<220> FEATURE:
<223> OTHER INFORMATION: Synthetic peptide

<400> SEQUENCE: 48

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Arg Pro Glu
                20                  25                  30

Ile Ser Trp Tyr Gln Gln Lys Pro Gly Gln Thr Pro Lys Leu Leu Ile
            35                  40                  45

Tyr Gly Ala Ser Arg Leu Gln Thr Gly Val Pro Ser Arg Phe Ser Gly
        50                  55                  60

Gly Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Asp Tyr Ser Trp Pro Tyr
                85                  90                  95

Ser Phe Gly Gln Gly Thr Lys Leu Glu Ile Lys
                100                 105
```

<210> SEQ ID NO 49
<211> LENGTH: 5
<212> TYPE: PRT
<213> ORGANISM: Artificial sequence
<220> FEATURE:
<223> OTHER INFORMATION: Synthetic peptide

<400> SEQUENCE: 49

```
Ser Ser Phe Met Ser
1               5
```

<210> SEQ ID NO 50
<211> LENGTH: 16
<212> TYPE: PRT
<213> ORGANISM: Artificial sequence
<220> FEATURE:
<223> OTHER INFORMATION: Synthetic peptide

<400> SEQUENCE: 50

```
Thr Ile Asn Gly Asn Gly Gly Thr Tyr Tyr Ala Asp Ser Met Lys Gly
1               5                   10                  15
```

<210> SEQ ID NO 51
<211> LENGTH: 14
<212> TYPE: PRT
<213> ORGANISM: Artificial sequence
<220> FEATURE:
<223> OTHER INFORMATION: Synthetic peptide

<400> SEQUENCE: 51

Asp Trp Ile Ser Gly Gly Tyr Tyr Phe Pro Ala Leu Gly Tyr

-continued

```
1               5                   10
```

<210> SEQ ID NO 52
<211> LENGTH: 22
<212> TYPE: PRT
<213> ORGANISM: Artificial sequence
<220> FEATURE:
<223> OTHER INFORMATION: Synthetic peptide

<400> SEQUENCE: 52

```
Ser Tyr Glu Leu Thr Gln Ser Pro Ser Val Ser Val Ala Gln Thr Gln
1               5                   10                  15

Thr Ala Lys Ile Thr Cys
            20
```

<210> SEQ ID NO 53
<211> LENGTH: 15
<212> TYPE: PRT
<213> ORGANISM: Artificial sequence
<220> FEATURE:
<223> OTHER INFORMATION: Synthetic peptide

<400> SEQUENCE: 53

```
Trp Tyr Gln Gln Lys Pro Gly Gln Ala Pro Val Leu Ala Ile Tyr
1               5                   10                  15
```

<210> SEQ ID NO 54
<211> LENGTH: 32
<212> TYPE: PRT
<213> ORGANISM: Artificial sequence
<220> FEATURE:
<223> OTHER INFORMATION: Synthetic peptide

<400> SEQUENCE: 54

```
Gly Ile Pro Glu Arg Phe Ser Gly Ser Asn Ser Gly Asn Thr Ala Thr
1               5                   10                  15

Leu Thr Ile Thr Gly Ala Gln Ala Glu Asp Glu Ala Asp Tyr Tyr Cys
            20                  25                  30
```

<210> SEQ ID NO 55
<211> LENGTH: 22
<212> TYPE: PRT
<213> ORGANISM: Artificial sequence
<220> FEATURE:
<223> OTHER INFORMATION: Synthetic peptide

<400> SEQUENCE: 55

```
Ser Tyr Glu Leu Thr Gln Ser Pro Ser Leu Ser Val Ala Leu Arg Gln
1               5                   10                  15

Thr Ala Lys Met Thr Cys
            20
```

<210> SEQ ID NO 56
<211> LENGTH: 15
<212> TYPE: PRT
<213> ORGANISM: Artificial sequence
<220> FEATURE:
<223> OTHER INFORMATION: Synthetic peptide

<400> SEQUENCE: 56

```
Trp Tyr Gln Gln Lys Pro Gly Gln Ala Pro Val Leu Val Ile Tyr
1               5                   10                  15
```

<210> SEQ ID NO 57
<211> LENGTH: 32

```
<212> TYPE: PRT
<213> ORGANISM: Artificial sequence
<220> FEATURE:
<223> OTHER INFORMATION: Synthetic peptide

<400> SEQUENCE: 57

Gly Ile Pro Glu Arg Phe Ala Gly Ser Asn Ala Gly Asn Thr Ala Thr
1               5                   10                  15

Leu Thr Ile Ser Gly Ala Gln Ala Glu Asp Glu Ala Asp Tyr Tyr Cys
            20                  25                  30

<210> SEQ ID NO 58
<211> LENGTH: 22
<212> TYPE: PRT
<213> ORGANISM: Artificial sequence
<220> FEATURE:
<223> OTHER INFORMATION: Synthetic peptide

<400> SEQUENCE: 58

Ser Tyr Glu Leu Thr Gln Ser Pro Ser Val Ser Val Ala Leu Arg Gln
1               5                   10                  15

Thr Ala Lys Ile Thr Cys
            20

<210> SEQ ID NO 59
<211> LENGTH: 32
<212> TYPE: PRT
<213> ORGANISM: Artificial sequence
<220> FEATURE:
<223> OTHER INFORMATION: Synthetic peptide

<400> SEQUENCE: 59

Gly Ile His Glu Arg Phe Ser Gly Ser Asn Ser Gly Asn Thr Ala Thr
1               5                   10                  15

Leu Thr Ile Gly Gly Ala Gln Ala Glu Asp Glu Ala Asp Tyr Tyr Cys
            20                  25                  30

<210> SEQ ID NO 60
<211> LENGTH: 15
<212> TYPE: PRT
<213> ORGANISM: Artificial sequence
<220> FEATURE:
<223> OTHER INFORMATION: Synthetic peptide

<400> SEQUENCE: 60

Trp Tyr Gln Gln Ser Pro Gly Gln Ala Pro Val Leu Val Ile Tyr
1               5                   10                  15

<210> SEQ ID NO 61
<211> LENGTH: 32
<212> TYPE: PRT
<213> ORGANISM: Artificial sequence
<220> FEATURE:
<223> OTHER INFORMATION: Synthetic peptide

<400> SEQUENCE: 61

Gly Ile Pro Glu Arg Phe Ser Gly Ser Asn Ser Gly Asn Thr Ala Thr
1               5                   10                  15

Leu Thr Ile Ser Gly Ala Arg Ala Glu Asp Glu Ala Asp Tyr Tyr Cys
            20                  25                  30

<210> SEQ ID NO 62
<211> LENGTH: 32
<212> TYPE: PRT
<213> ORGANISM: Artificial sequence
```

```
<220> FEATURE:
<223> OTHER INFORMATION: Synthetic peptide

<400> SEQUENCE: 62

Gly Ile Pro Glu Arg Phe Ser Gly Ser Asn Ser Gly Asn Thr Ala Thr
 1               5                  10                  15

Leu Thr Ile Ser Gly Ala Gln Ala Glu Asp Glu Ala Asp Tyr Tyr Cys
                20                  25                  30

<210> SEQ ID NO 63
<211> LENGTH: 122
<212> TYPE: PRT
<213> ORGANISM: Artificial sequence
<220> FEATURE:
<223> OTHER INFORMATION: Synthetic peptide

<400> SEQUENCE: 63

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Ser Ser Ser
                20                  25                  30

Phe Met Ser Trp Val Arg Gln Ala Pro Gly Lys Gly Leu Glu Trp Val
            35                  40                  45

Ser Thr Ile Asn Gly Asn Gly Gly Thr Tyr Tyr Ala Asp Ser Met Lys
        50                  55                  60

Gly Arg Phe Thr Ile Ser Arg Asp Asn Val Lys Ser Thr Val Thr Leu
65                  70                  75                  80

Gln Met Asn Ser Leu Lys Pro Glu Asp Thr Ala Val Tyr Tyr Cys Ala
                85                  90                  95

Ala Asp Trp Ile Ser Gly Gly Tyr Tyr Phe Pro Ala Leu Gly Tyr Trp
            100                 105                 110

Gly Gln Gly Thr Gln Val Thr Val Ser Ser
        115                 120

<210> SEQ ID NO 64
<211> LENGTH: 108
<212> TYPE: PRT
<213> ORGANISM: Artificial sequence
<220> FEATURE:
<223> OTHER INFORMATION: Synthetic peptide

<400> SEQUENCE: 64

Ser Tyr Glu Leu Thr Gln Ser Pro Ser Val Ser Val Ala Gln Thr Gln
 1               5                  10                  15

Thr Ala Lys Ile Thr Cys Gly Gly Asp Asn Ile Gly Ser Lys Ser Val
                20                  25                  30

Gln Trp Tyr Gln Gln Lys Pro Gly Gln Ala Pro Val Leu Ala Ile Tyr
            35                  40                  45

Ala Asp Thr Arg Arg Pro Ser Gly Ile Pro Glu Arg Phe Ser Gly Ser
        50                  55                  60

Asn Ser Gly Asn Thr Ala Thr Leu Thr Ile Thr Gly Ala Gln Ala Glu
65                  70                  75                  80

Asp Glu Ala Asp Tyr Tyr Cys Gln Val Trp Asp Thr Ser Thr Asn Val
                85                  90                  95

Ala Val Phe Gly Gly Gly Thr Arg Leu Thr Ile Leu
            100                 105

<210> SEQ ID NO 65
<211> LENGTH: 108
```

```
<212> TYPE: PRT
<213> ORGANISM: Artificial sequence
<220> FEATURE:
<223> OTHER INFORMATION: Synthetic peptide

<400> SEQUENCE: 65

Ser Tyr Glu Leu Thr Gln Ser Pro Ser Leu Ser Val Ala Leu Arg Gln
1               5                   10                  15

Thr Ala Lys Met Thr Cys Gly Gly Asn Lys Ile Gly Ser Lys Ser Ala
            20                  25                  30

Gln Trp Tyr Gln Gln Lys Pro Gly Gln Ala Pro Val Leu Val Ile Tyr
        35                  40                  45

Ala Asp Ser Arg Arg Pro Ser Gly Ile Pro Glu Arg Phe Ala Gly Ser
    50                  55                  60

Asn Ala Gly Asn Thr Ala Thr Leu Thr Ile Ser Gly Ala Gln Ala Glu
65                  70                  75                  80

Asp Glu Ala Asp Tyr Tyr Cys Gln Val Trp Asp Ile Ser Ala Asn Ala
                85                  90                  95

Ala Val Phe Gly Gly Gly Thr His Leu Thr Val Leu
            100                 105

<210> SEQ ID NO 66
<211> LENGTH: 108
<212> TYPE: PRT
<213> ORGANISM: Artificial sequence
<220> FEATURE:
<223> OTHER INFORMATION: Synthetic peptide

<400> SEQUENCE: 66

Ser Tyr Glu Leu Thr Gln Ser Pro Ser Val Ser Val Ala Leu Arg Gln
1               5                   10                  15

Thr Ala Lys Ile Thr Cys Gly Gly Asn Asn Ile Gly Ser Leu Ser Thr
            20                  25                  30

Gln Trp Tyr Gln Gln Lys Pro Gly Gln Ala Pro Val Leu Val Ile Tyr
        35                  40                  45

Ala Asp Asn Arg Arg Pro Ser Gly Ile His Glu Arg Phe Ser Gly Ser
    50                  55                  60

Asn Ser Gly Asn Thr Ala Thr Leu Thr Ile Gly Ala Gln Ala Glu
65                  70                  75                  80

Asp Glu Ala Asp Tyr Tyr Cys Gln Val Trp Asp Asn Ser Ala Asn Ala
                85                  90                  95

Leu Val Phe Gly Gly Gly Thr His Leu Thr Val Leu
            100                 105

<210> SEQ ID NO 67
<211> LENGTH: 108
<212> TYPE: PRT
<213> ORGANISM: Artificial sequence
<220> FEATURE:
<223> OTHER INFORMATION: Synthetic peptide

<400> SEQUENCE: 67

Ser Tyr Glu Leu Thr Gln Ser Pro Ser Val Ser Val Ala Leu Arg Gln
1               5                   10                  15

Thr Ala Lys Ile Thr Cys Gly Gly Asp Asn Ile Gly Ser Lys Ser Ala
            20                  25                  30

Gln Trp Tyr Gln Gln Ser Pro Gly Gln Ala Pro Val Leu Val Ile Tyr
        35                  40                  45

Ala Asp Ala Ser Arg Pro Ser Gly Ile Pro Glu Arg Phe Ser Gly Ser
```

```
                 50                  55                  60
Asn Ser Gly Asn Thr Ala Thr Leu Thr Ile Ser Gly Ala Arg Ala Glu
 65                  70                  75                  80

Asp Glu Ala Asp Tyr Tyr Cys Gln Val Trp Asp Thr Ser Thr Asn Ala
                 85                  90                  95

Ala Val Phe Gly Gly Gly Thr His Leu Thr Val Leu
                100                 105
```

<210> SEQ ID NO 68
<211> LENGTH: 108
<212> TYPE: PRT
<213> ORGANISM: Artificial sequence
<220> FEATURE:
<223> OTHER INFORMATION: Synthetic peptide

<400> SEQUENCE: 68

```
Ser Tyr Glu Leu Thr Gln Ser Pro Ser Val Ser Val Ala Leu Arg Gln
  1               5                  10                  15

Thr Ala Lys Ile Thr Cys Gly Gly Asn Asn Ile Gly Ser Lys Ser Ala
                 20                  25                  30

Gln Trp Tyr Gln Gln Lys Pro Gly Gln Ala Pro Val Leu Val Ile Tyr
                 35                  40                  45

Ala Asp Ser Arg Arg Pro Ser Gly Ile Pro Glu Arg Phe Ser Gly Ser
             50                  55                  60

Asn Ser Gly Asn Thr Ala Thr Leu Thr Ile Ser Gly Ala Gln Ala Glu
 65                  70                  75                  80

Asp Glu Ala Asp Tyr Tyr Cys Gln Val Trp Asp Val Ser Thr Asn Ala
                 85                  90                  95

Ala Val Phe Gly Gly Gly Thr His Leu Ser Val Leu
                100                 105
```

<210> SEQ ID NO 69
<211> LENGTH: 108
<212> TYPE: PRT
<213> ORGANISM: Artificial sequence
<220> FEATURE:
<223> OTHER INFORMATION: Synthetic peptide

<400> SEQUENCE: 69

```
Ser Tyr Glu Leu Thr Gln Ser Pro Ser Val Ser Val Ala Leu Arg Gln
  1               5                  10                  15

Thr Ala Lys Ile Thr Cys Gly Gly Asn Asn Ile Gly Arg Lys Ser Ala
                 20                  25                  30

Gln Trp Tyr Gln Gln Lys Pro Gly Gln Ala Pro Val Leu Val Ile Tyr
                 35                  40                  45

Ala Asp Ser Arg Arg Pro Ser Gly Ile Pro Glu Arg Phe Ser Gly Ser
             50                  55                  60

Asn Ser Gly Asn Thr Ala Thr Leu Thr Ile Ser Gly Ala Gln Ala Glu
 65                  70                  75                  80

Asp Glu Ala Asp Tyr Tyr Cys Gln Val Trp Asp Ser Ser Ala Asn Ala
                 85                  90                  95

Ala Val Phe Gly Gly Gly Thr His Leu Thr Val Leu
                100                 105
```

<210> SEQ ID NO 70
<211> LENGTH: 5
<212> TYPE: PRT
<213> ORGANISM: Artificial sequence
<220> FEATURE:

<223> OTHER INFORMATION: Synthetic peptide

<400> SEQUENCE: 70

Ser Tyr Gly Met Ser
1               5

<210> SEQ ID NO 71
<211> LENGTH: 17
<212> TYPE: PRT
<213> ORGANISM: Artificial sequence
<220> FEATURE:
<223> OTHER INFORMATION: Synthetic peptide

<400> SEQUENCE: 71

Thr Ile Ser Arg Gly Gly Asp Ser Thr Ser Tyr Ala Asp Ser Val Lys
1               5                   10                  15

Gly

<210> SEQ ID NO 72
<211> LENGTH: 7
<212> TYPE: PRT
<213> ORGANISM: Artificial sequence
<220> FEATURE:
<223> OTHER INFORMATION: Synthetic peptide

<400> SEQUENCE: 72

Leu Gly Arg Leu Gly Phe Gly
1               5

<210> SEQ ID NO 73
<211> LENGTH: 14
<212> TYPE: PRT
<213> ORGANISM: Artificial sequence
<220> FEATURE:
<223> OTHER INFORMATION: Synthetic peptide

<400> SEQUENCE: 73

Ala Gly Thr Ser Ser Asp Ile Gly Asp Trp Asn Tyr Val Ser
1               5                   10

<210> SEQ ID NO 74
<211> LENGTH: 10
<212> TYPE: PRT
<213> ORGANISM: Artificial sequence
<220> FEATURE:
<223> OTHER INFORMATION: Synthetic peptide

<400> SEQUENCE: 74

Thr Ser Tyr Arg Ser Gly Asn Asn Trp Val
1               5                   10

<210> SEQ ID NO 75
<211> LENGTH: 10
<212> TYPE: PRT
<213> ORGANISM: Artificial sequence
<220> FEATURE:
<223> OTHER INFORMATION: Synthetic peptide

<400> SEQUENCE: 75

Val Ser Tyr Arg Ser Gly Asn Asn Trp Val
1               5                   10

<210> SEQ ID NO 76
<211> LENGTH: 116
<212> TYPE: PRT
<213> ORGANISM: Artificial sequence

```
<220> FEATURE:
<223> OTHER INFORMATION: Synthetic peptide

<400> SEQUENCE: 76

Glu Leu Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Thr Ile Ser Arg Gly Gly Asp Ser Thr Ser Tyr Ala Asp Ser Val
    50                  55                  60

Lys Gly Arg Phe Thr Ile Ser Lys Asp Asn Ala Lys Asn Thr Leu Tyr
65                  70                  75                  80

Leu Gln Met Asn Ser Leu Glu Pro Glu Asp Thr Ala Val Tyr Tyr Cys
                85                  90                  95

Ala Asn Leu Gly Arg Leu Gly Phe Gly Arg Gly Gln Gly Thr Gln Val
            100                 105                 110

Thr Val Ser Ser
            115

<210> SEQ ID NO 77
<211> LENGTH: 110
<212> TYPE: PRT
<213> ORGANISM: Artificial sequence
<220> FEATURE:
<223> OTHER INFORMATION: Synthetic peptide

<400> SEQUENCE: 77

Ser Ser Ala Leu Thr Gln Pro Pro Ser Met Ser Gly Thr Leu Gly Lys
1               5                   10                  15

Thr Leu Thr Ile Ser Cys Ala Gly Thr Ser Ser Asp Ile Gly Asp Trp
            20                  25                  30

Asn Tyr Val Ser Trp Phe Gln Gln Leu Pro Gly Thr Ala Pro Lys Leu
        35                  40                  45

Leu Ile Ser Glu Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Thr Ser Tyr Arg Ser Gly
                85                  90                  95

Asn Asn Trp Val Phe Gly Gly Gly Thr His Leu Thr Val Leu
            100                 105                 110

<210> SEQ ID NO 78
<211> LENGTH: 110
<212> TYPE: PRT
<213> ORGANISM: Artificial sequence
<220> FEATURE:
<223> OTHER INFORMATION: Synthetic peptide

<400> SEQUENCE: 78

Gln Ala Gly Leu Thr Gln Pro Pro Ser Met Ser Gly Thr Leu Gly Lys
1               5                   10                  15

Thr Leu Thr Ile Ser Cys Ala Gly Thr Ser Ser Asp Ile Gly Asp Trp
            20                  25                  30

Asn Tyr Val Ser Trp Tyr Gln Gln Leu Pro Gly Thr Ala Pro Lys Leu
        35                  40                  45
```

```
Leu Ile Tyr Glu Val Asn Lys Arg Ala Ser Gly Ile Pro Asp Arg Phe
 50                  55                  60

Ser Gly Ser Lys Ser Gly Asn Thr Ala Ser Leu Ser Ile Ser Gly Leu
 65                  70                  75                  80

Gln Ser Glu Asp Glu Ala Asp Tyr Tyr Cys Val Ser Tyr Arg Ser Gly
                 85                  90                  95

Asn Asn Trp Val Phe Gly Gly Gly Thr His Leu Thr Val Leu
            100                 105                 110

<210> SEQ ID NO 79
<211> LENGTH: 110
<212> TYPE: PRT
<213> ORGANISM: Artificial sequence
<220> FEATURE:
<223> OTHER INFORMATION: Synthetic peptide

<400> SEQUENCE: 79

Ser Tyr Glu Leu Thr Gln Pro Pro Ser Val Ser Gly Ser Pro Gly Lys
 1               5                  10                  15

Thr Leu Thr Ile Ser Cys Ala Gly Thr Ser Ser Asp Ile Gly Asp Trp
                 20                  25                  30

Asn Tyr Val Ser Trp Phe Gln Gln Leu Pro Gly Thr Ala Pro Lys Leu
             35                  40                  45

Leu Ile Ser Glu Val Asn Lys Arg Ala Ser Gly Ile Pro Asp Arg Phe
 50                  55                  60

Ser Gly Ser Lys Ser Gly Asn Thr Ala Ser Leu Ser Ile Ser Gly Leu
 65                  70                  75                  80

Gln Ser Glu Asp Glu Ala Asp Tyr Tyr Cys Thr Ser Tyr Arg Ser Gly
                 85                  90                  95

Asn Asn Trp Val Phe Gly Gly Gly Thr His Leu Thr Val Leu
            100                 105                 110

<210> SEQ ID NO 80
<211> LENGTH: 10
<212> TYPE: PRT
<213> ORGANISM: Artificial sequence
<220> FEATURE:
<223> OTHER INFORMATION: Synthetic peptide

<400> SEQUENCE: 80

Glu Pro Lys Ser Cys Asp Lys Thr His Thr
 1               5                  10

<210> SEQ ID NO 81
<211> LENGTH: 5
<212> TYPE: PRT
<213> ORGANISM: Artificial sequence
<220> FEATURE:
<223> OTHER INFORMATION: Synthetic peptide

<400> SEQUENCE: 81

Cys Pro Pro Cys Pro
 1               5

<210> SEQ ID NO 82
<211> LENGTH: 8
<212> TYPE: PRT
<213> ORGANISM: Artificial sequence
<220> FEATURE:
<223> OTHER INFORMATION: Synthetic peptide

<400> SEQUENCE: 82
```

```
Ala Pro Glu Leu Leu Gly Gly Pro
1               5
```

<210> SEQ ID NO 83
<211> LENGTH: 12
<212> TYPE: PRT
<213> ORGANISM: Artificial sequence
<220> FEATURE:
<223> OTHER INFORMATION: Synthetic peptide

<400> SEQUENCE: 83

```
Glu Leu Lys Thr Pro Leu Gly Asp Thr Thr His Thr
1               5                   10
```

<210> SEQ ID NO 84
<211> LENGTH: 50
<212> TYPE: PRT
<213> ORGANISM: Artificial sequence
<220> FEATURE:
<223> OTHER INFORMATION: Synthetic peptide

<400> SEQUENCE: 84

```
Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro
    50
```

<210> SEQ ID NO 85
<211> LENGTH: 7
<212> TYPE: PRT
<213> ORGANISM: Artificial sequence
<220> FEATURE:
<223> OTHER INFORMATION: Synthetic peptide

<400> SEQUENCE: 85

```
Glu Ser Lys Tyr Gly Pro Pro
1               5
```

<210> SEQ ID NO 86
<211> LENGTH: 5
<212> TYPE: PRT
<213> ORGANISM: Artificial sequence
<220> FEATURE:
<223> OTHER INFORMATION: Synthetic peptide

<400> SEQUENCE: 86

```
Cys Pro Ser Cys Pro
1               5
```

<210> SEQ ID NO 87
<211> LENGTH: 8
<212> TYPE: PRT
<213> ORGANISM: Artificial sequence
<220> FEATURE:
<223> OTHER INFORMATION: Synthetic peptide

<400> SEQUENCE: 87

```
Ala Pro Glu Phe Leu Gly Gly Pro
1               5
```

<210> SEQ ID NO 88

```
<211> LENGTH: 3
<212> TYPE: PRT
<213> ORGANISM: Artificial sequence
<220> FEATURE:
<223> OTHER INFORMATION: Synthetic peptide

<400> SEQUENCE: 88

Glu Arg Lys
1

<210> SEQ ID NO 89
<211> LENGTH: 10
<212> TYPE: PRT
<213> ORGANISM: Artificial sequence
<220> FEATURE:
<223> OTHER INFORMATION: Synthetic peptide

<400> SEQUENCE: 89

Cys Cys Val Glu Cys Pro Pro Pro Cys Pro
1               5                   10

<210> SEQ ID NO 90
<211> LENGTH: 7
<212> TYPE: PRT
<213> ORGANISM: Artificial sequence
<220> FEATURE:
<223> OTHER INFORMATION: Synthetic peptide

<400> SEQUENCE: 90

Ala Pro Pro Val Ala Gly Pro
1               5

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Pro Leu Tyr Ser Asn Leu Ala Gly Asp Leu Gly Ser
1               5                   10

<210> SEQ ID NO 92
<211> LENGTH: 12
<212> TYPE: PRT
<213> ORGANISM: Artificial sequence
<220> FEATURE:
<223> OTHER INFORMATION: Synthetic peptide

<400> SEQUENCE: 92

Pro Leu Tyr Ser Asn Leu Ala Gly Asp Phe Gly Ser
1               5                   10

<210> SEQ ID NO 93
<211> LENGTH: 12
<212> TYPE: PRT
<213> ORGANISM: Artificial sequence
<220> FEATURE:
<223> OTHER INFORMATION: Synthetic peptide

<400> SEQUENCE: 93

Pro Leu Tyr Asn Asn Leu Ala Gly Asp Phe Gly Ser
1               5                   10

<210> SEQ ID NO 94
<211> LENGTH: 12
```

```
<212> TYPE: PRT
<213> ORGANISM: Artificial sequence
<220> FEATURE:
<223> OTHER INFORMATION: Synthetic peptide

<400> SEQUENCE: 94

Pro Leu Tyr Ser Asn Phe Ala Gly Asp Phe Gly Ser
1               5                   10

<210> SEQ ID NO 95
<211> LENGTH: 12
<212> TYPE: PRT
<213> ORGANISM: Artificial sequence
<220> FEATURE:
<223> OTHER INFORMATION: Synthetic peptide

<400> SEQUENCE: 95

Pro Leu Tyr Asn Asn Phe Ala Gly His Phe Gly Ser
1               5                   10

<210> SEQ ID NO 96
<211> LENGTH: 7
<212> TYPE: PRT
<213> ORGANISM: Artificial sequence
<220> FEATURE:
<223> OTHER INFORMATION: Synthetic peptide

<400> SEQUENCE: 96

Gly Gly Ser Arg Leu Gln Ala
1               5

<210> SEQ ID NO 97
<211> LENGTH: 9
<212> TYPE: PRT
<213> ORGANISM: Artificial sequence
<220> FEATURE:
<223> OTHER INFORMATION: Synthetic peptide

<400> SEQUENCE: 97

Leu Gln Val Tyr Ser Trp Pro Leu Thr
1               5

<210> SEQ ID NO 98
<211> LENGTH: 9
<212> TYPE: PRT
<213> ORGANISM: Artificial sequence
<220> FEATURE:
<223> OTHER INFORMATION: Synthetic peptide

<400> SEQUENCE: 98

Gln Gln Asp Tyr Ser Trp Pro Leu Thr
1               5

<210> SEQ ID NO 99
<211> LENGTH: 121
<212> TYPE: PRT
<213> ORGANISM: Artificial sequence
<220> FEATURE:
<223> OTHER INFORMATION: Synthetic peptide

<400> SEQUENCE: 99

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Leu Thr Trp Val Arg Gln Ala Pro Gly Lys Gly Leu Glu Trp Val
```

```
                35                  40                  45
Ser Thr Ile Lys Ala Arg Gly Gly Thr Thr Leu Tyr Ala Asp Ser Val
         50                  55                  60
Lys Asp Arg Phe Thr Ile Ser Arg Asp Asn Ala Lys Asn Thr Leu Tyr
 65                  70                  75                  80
Leu Leu Met Asn Ser Leu Lys Pro Glu Asp Thr Ala Val Tyr Tyr Cys
                 85                  90                  95
Ala Lys Pro Leu Tyr Ser Asn Leu Ala Gly Asp Leu Gly Ser Trp Gly
            100                 105                 110
Gln Gly Thr Thr Val Thr Val Ser Ser
        115                 120

<210> SEQ ID NO 100
<211> LENGTH: 107
<212> TYPE: PRT
<213> ORGANISM: Artificial sequence
<220> FEATURE:
<223> OTHER INFORMATION: Synthetic peptide

<400> SEQUENCE: 100

Asp Ile Gln Met Thr Gln Ser Pro Ser Ser Leu Ser Ala Ser Leu Gly
 1               5                  10                  15
Asp Arg Val Thr Ile Thr Cys Gln Ala Ser Gln Ser Ile Ser Ser Tyr
            20                  25                  30
Leu Ala Trp Tyr Gln Gln Lys Pro Gly Gln Ala Pro Lys Leu Leu Ile
         35                  40                  45
Tyr Gly Gly Ser Arg Leu Gln Thr Gly Val Pro Ser Arg Phe Ser Gly
 50                  55                  60
Ser Gly Ser Gly Thr Ser Phe Thr Leu Thr Ile Ser Gly Leu Glu Thr
 65                  70                  75                  80
Glu Asp Leu Ala Thr Tyr Tyr Cys Leu Gln Asp Tyr Ser Trp Pro Leu
                 85                  90                  95
Thr Phe Gly Gln Gly Thr Lys Leu Glu Ile Lys
            100                 105

<210> SEQ ID NO 101
<211> LENGTH: 121
<212> TYPE: PRT
<213> ORGANISM: Artificial sequence
<220> FEATURE:
<223> OTHER INFORMATION: Synthetic peptide

<400> SEQUENCE: 101

Gln Val Gln Leu Gln Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ser Leu Thr Trp Val Arg Gln Ala Pro Gly Lys Gly Leu Glu Trp Val
         35                  40                  45
Ser Thr Ile Lys Ala Arg Gly Gly Thr Thr Leu Tyr Ala Asp Ser Val
         50                  55                  60
Lys Asp Arg Phe Thr Ile Ser Arg Asp Asn Ala Lys Asn Thr Leu Tyr
 65                  70                  75                  80
Leu Gln Met Asn Ser Leu Lys Pro Glu Asp Thr Ala Val Tyr Tyr Cys
                 85                  90                  95
Ala Lys Pro Leu Tyr Ser Asn Leu Ala Gly Asp Phe Gly Ser Trp Gly
            100                 105                 110
```

Gln Gly Thr Thr Val Thr Val Ser Ser
        115                 120

<210> SEQ ID NO 102
<211> LENGTH: 107
<212> TYPE: PRT
<213> ORGANISM: Artificial sequence
<220> FEATURE:
<223> OTHER INFORMATION: Synthetic peptide

<400> SEQUENCE: 102

Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Ser Gly Gln Ala Pro Lys Leu Leu Ile
        35                  40                  45

Tyr Gly Gly Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Thr
65                  70                  75                  80

Glu Asp Leu Ala Thr Tyr Tyr Cys Leu Gln Val Tyr Ser Trp Pro Leu
                85                  90                  95

Thr Phe Gly Gln Gly Thr Lys Leu Glu Ile Lys
            100                 105

<210> SEQ ID NO 103
<211> LENGTH: 121
<212> TYPE: PRT
<213> ORGANISM: Artificial sequence
<220> FEATURE:
<223> OTHER INFORMATION: Synthetic peptide

<400> SEQUENCE: 103

Gln Val Gln Leu Gln Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Leu Thr Trp Val Arg Gln Ala Pro Gly Lys Gly Leu Glu Trp Val
        35                  40                  45

Ser Thr Ile Lys Ala Arg Gly Gly Thr Thr Leu Tyr Ala Asp Ser Val
    50                  55                  60

Lys Asp Arg Phe Thr Ile Ser Arg Asp Asn Ala Lys Asn Thr Leu Tyr
65                  70                  75                  80

Leu Leu Val Asn Ser Leu Lys Pro Glu Asp Thr Ala Val Tyr Tyr Cys
                85                  90                  95

Ala Lys Pro Leu Tyr Asn Asn Leu Ala Gly Asp Phe Gly Ser Trp Gly
            100                 105                 110

Gln Gly Thr Thr Val Thr Val Ser Ser
        115                 120

<210> SEQ ID NO 104
<211> LENGTH: 107
<212> TYPE: PRT
<213> ORGANISM: Artificial sequence
<220> FEATURE:
<223> OTHER INFORMATION: Synthetic peptide

<400> SEQUENCE: 104

Asp Ile Gln Met Thr Gln Ser Pro Ser Ser Leu Ser Ala Ser Leu Gly

```
                1               5                  10                 15
Asp Arg Val Thr Ile Thr Cys Gln Ala Ser Gln Ser Ile Ser Ser Tyr
            20                  25                 30

Leu Ala Trp Tyr Gln Gln Lys Pro Gly Gln Ala Pro Lys Leu Leu Ile
            35                  40                 45

Tyr Gly Gly Ser Arg Leu Gln Ala Gly Val Pro Ser Arg Phe Ser Gly
            50                  55                 60

Ser Gly Ser Gly Thr Ser Phe Thr Leu Thr Ile Gly Gly Leu Glu Thr
65                  70                  75                     80

Glu Asp Leu Ala Thr Tyr Tyr Cys Gln Gln Asp Tyr Ser Trp Pro Leu
            85                  90                 95

Thr Phe Gly Gln Gly Thr Lys Leu Glu Ile Lys
            100                 105
```

<210> SEQ ID NO 105
<211> LENGTH: 121
<212> TYPE: PRT
<213> ORGANISM: Artificial sequence
<220> FEATURE:
<223> OTHER INFORMATION: Synthetic peptide

<400> SEQUENCE: 105

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Leu Thr Trp Val Arg Gln Ala Pro Gly Lys Gly Leu Glu Trp Val
            35                  40                  45

Ser Thr Ile Lys Ala Arg Gly Gly Thr Thr Leu Tyr Ala Asp Ser Val
            50                  55                  60

Lys Asp Arg Phe Thr Ile Ser Arg Asp Asn Ala Lys Asn Thr Leu Tyr
65                  70                  75                      80

Leu Leu Met Asn Ser Leu Lys Pro Glu Asp Thr Ala Val Tyr Tyr Cys
            85                  90                  95

Val Lys Pro Leu Tyr Ser Asn Phe Ala Gly Asp Phe Gly Ser Trp Gly
            100                 105                 110

Gln Gly Thr Thr Val Thr Val Ser Ser
            115                 120
```

<210> SEQ ID NO 106
<211> LENGTH: 107
<212> TYPE: PRT
<213> ORGANISM: Artificial sequence
<220> FEATURE:
<223> OTHER INFORMATION: Synthetic peptide

<400> SEQUENCE: 106

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Arg Leu Leu Ile
            35                  40                  45

Tyr Gly Gly Ser Arg Leu Gln Thr Gly Val Pro Ser Arg Phe Ser Gly
            50                  55                  60

Ser Gly Ser Gly Thr Ser Phe Thr Leu Thr Ile Ser Gly Leu Glu Thr
65                  70                  75                      80
```

<210> SEQ ID NO 107
<211> LENGTH: 121
<212> TYPE: PRT
<213> ORGANISM: Artificial sequence
<220> FEATURE:
<223> OTHER INFORMATION: Synthetic peptide

<400> SEQUENCE: 107

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Leu Thr Trp Val Arg Gln Ala Pro Gly Lys Gly Leu Glu Trp Val
        35                  40                  45

Ser Thr Ile Lys Ala Arg Gly Gly Thr Thr Leu Tyr Ala Asp Ser Val
    50                  55                  60

Lys Asp Arg Phe Thr Ile Ser Arg Asp Asn Ala Lys Asn Thr Leu Tyr
65                  70                  75                  80

Leu Leu Met Asn Ser Leu Lys Pro Glu Asp Thr Ala Val Tyr Tyr Cys
                85                  90                  95

Ala Lys Pro Leu Tyr Asn Asn Phe Ala Gly His Phe Gly Ser Trp Gly
            100                 105                 110

Gln Gly Thr Thr Val Thr Val Ser Ser
            115                 120
```

<210> SEQ ID NO 108
<211> LENGTH: 107
<212> TYPE: PRT
<213> ORGANISM: Artificial sequence
<220> FEATURE:
<223> OTHER INFORMATION: Synthetic peptide

<400> SEQUENCE: 108

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Gly Gly Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Thr
65                  70                  75                  80

Glu Asp Leu Ala Thr Tyr Tyr Cys Gln Gln Asp Tyr Ser Trp Pro Leu
                85                  90                  95

Thr Phe Gly Gln Gly Thr Lys Leu Glu Ile Lys
            100                 105
```